United States Patent
Kenmoku et al.

(10) Patent No.: US 6,908,720 B2
(45) Date of Patent: Jun. 21, 2005

(54) POLYHYDROXYALKANOATE, ITS PRODUCTION METHOD, CHARGE CONTROL AGENT CONTAINING THE POLYHYDROXYALKANOATE, TONER BINDER AND TONER, AND IMAGE FORMING METHOD AND IMAGE FORMING APPARATUS USING THE TONER

(75) Inventors: Takashi Kenmoku, Kanagawa (JP); Toyoko Kobayashi, Kanagawa (JP); Etsuko Sugawa, Kanagawa (JP); Tetsuya Yano, Kanagawa (JP); Shin Kobayashi, Kanagawa (JP); Takeshi Imamura, Kanagawa (JP); Tsutomu Honma, Kanagawa (JP)

(73) Assignee: Canon Kabushiki Kaisha, Toyko (JP)

( * ) Notice: Subject to any disclaimer, the term of this patent is extended or adjusted under 35 U.S.C. 154(b) by 339 days.

(21) Appl. No.: 10/133,576

(22) Filed: Apr. 29, 2002

(65) Prior Publication Data

US 2003/0104300 A1 Jun. 5, 2003

(30) Foreign Application Priority Data

Apr. 27, 2001 (JP) ........................................ 2001-133651
Apr. 27, 2001 (JP) ........................................ 2001-133667

(51) Int. Cl.[7] ........................... C08G 13/06; C08F 20/00
(52) U.S. Cl. ........................ 430/97; 528/361; 528/364; 525/437; 525/444; 430/105; 430/109; 430/110; 430/311; 430/644
(58) Field of Search ................................. 528/361, 364; 525/437, 444, 450; 430/97, 105, 109, 110, 311, 644

(56) References Cited

U.S. PATENT DOCUMENTS

| | | | |
|---|---|---|---|
| 4,393,167 A | 7/1983 | Holmes et al. | ................ 525/64 |
| 4,442,189 A | 4/1984 | Lu et al. | ........................ 430/45 |
| 4,480,021 A | 10/1984 | Lu et al. | ................... 430/106.6 |
| 4,795,690 A | 1/1989 | Shindo et al. | ............... 430/109 |
| 4,876,331 A | 10/1989 | Doi | ............................ 528/361 |
| 4,925,765 A | 5/1990 | Madeleine | ................... 430/110 |
| 5,004,664 A | 4/1991 | Fuller et al. | |
| 5,135,859 A | 8/1992 | Witholt et al. | ............... 435/135 |
| 5,200,332 A | 4/1993 | Yamane et al. | .............. 435/135 |
| 5,292,860 A | 3/1994 | Shiotani et al. | ............. 528/361 |
| 5,612,161 A | 3/1997 | Watanabe et al. | ........... 430/110 |
| 5,667,927 A | 9/1997 | Kubota et al. | .............. 430/109 |

FOREIGN PATENT DOCUMENTS

| | | |
|---|---|---|
| JP | 60-108861 | 6/1985 |
| JP | 61-3149 | 1/1986 |
| JP | 63-38958 | 2/1986 |

(Continued)

OTHER PUBLICATIONS

Aróstegui, et al.; "Bacterial Polyesters Produced by *Pseudomonas oleovorans* Containing Nitrophenyl Groups"; Macromolecules 32, 9, (1999) 2889–2895.

Curley, et al.; "Production of Poly(3–hydroxyalkanoates) Containing Aromatic Substituents by *Pseudomonas oleovorans*"; Macromolecules 1996, 29, 1762–1766.

Fritzsche, et al.; "An unusual bacterial polyester with a phenyl pendant group"; Makromal. Chem., 191, 1957–1965 (1990).

(Continued)

*Primary Examiner*—Samuel A. Acquah
(74) *Attorney, Agent, or Firm*—Fitzpatrick, Cella, Harper and Scinto

(57) ABSTRACT

The present invention provides a novel PHA comprising a unit containing thioether with high reactivity, and its production method. The present invention also provides polyhydroxyalkanoate (PHA) comprising units having defined chemical formulas (1) and (2), and at least one of four units having defined chemical formulas (3), (4), (5) and (6); its production method; a charge control agent containing the PHA; a toner binder containing the charge control agent; an electrostatic latent image developing toner; and an image forming method and an image forming apparatus using the electrostatic latent image developing toner.

32 Claims, 8 Drawing Sheets

FOREIGN PATENT DOCUMENTS

| | | |
|---|---|---|
| JP | 63-88564 | 4/1988 |
| JP | 5-7492 | 1/1993 |
| JP | 5-93049 | 4/1993 |
| JP | 6-15604 | 3/1994 |
| JP | 6-289644 | 10/1994 |
| JP | 7-14352 | 2/1995 |
| JP | 7-72658 | 3/1995 |
| JP | 7-120975 | 5/1995 |
| JP | 7-265065 | 10/1995 |
| JP | 8-179564 | 7/1996 |
| JP | 8-262796 | 10/1996 |
| JP | 8-19227 | 12/1996 |
| JP | 2623684 | 6/1997 |
| JP | 9-191893 | 7/1997 |
| JP | 2642937 | 8/1997 |
| JP | 9-281746 | 10/1997 |
| JP | 2807795 | 10/1998 |
| JP | 2989175 | 12/1999 |

OTHER PUBLICATIONS

Gross, et al., "Cyanophenoxy–containing Microbial Polyesters . . . Bioegradable"; Polmer International. 39(1996) 205–213.

Grund, et al., "Regulation of Alkane Oxidation in *Pseudomonas putida*"; J. Bact. 123, 546–556 (1975).

Kim, et al.; "Preparation and Characterization of Poly(β–hydroxyalkanoates) Obtained from *Pseudomonas oleovorans* Grown with Mixtures of 5–Phenylvaleric Acid and n–Alkanoic Acids"; Macromolecules 1991, 24, 5256–5260.

Lytle, et al.; "Filtration Sizes of Human Immunodeficiency Virus Type 1 and Surrogate Viruses Used to Test Barrier Materials"; Appl. & Environm. Microbiol., 1992, 58, 2, 747–749.

Park, et al.; "Epoxidation of Bacterial Polyesters with Unsaturated Side Chains. I. Production and Epoxidation of Polyesters from 10–Undecenoic Acid"; Macromolecules 31, 5, 1480–1486 (1998).

Takagi, et al., "Biosynthesis of Polyhydroxyalkanate with a Thiophenoxy Side Group Obtained from *Pseudomonas putida*"; *Macromolecules* 1999, 32, 8315–8318.

Park, et al.; "Epoxidation of Bacterial Polyesters with Unsaturated Side Chains. II. Rate of Epoxidation and Polymer Properties"; J. Polyn. Sci., Part A, Polymer Chemistry, 36 2381–2387 (1998).

Ramsey, et al., "Effects of Nitrogen Limitation on Long–Side–Chain Poly–β–Hydroxyalkanoate Synthesis by *Pseudomonas resinovarons*"; Applied Environ. Microb., 58, 2 744–746 (1992).

Ritter, et al.; "Bacterial production of polyesters bearing phenoxy groups in the side chains, 1"; Macromol. Chem. Phys. 195, 1665–1672 (1994).

POLYHYDROXYALKANOATE, ITS PRODUCTION METHOD, CHARGE CONTROL AGENT CONTAINING THE POLYHYDROXYALKANOATE, TONER BINDER AND TONER, AND IMAGE FORMING METHOD AND IMAGE FORMING APPARATUS USING THE TONER

BACKGROUND OF THE INVENTION

1. Field of the Invention

The present invention relates to a novel polyhydroxyalkanoate (PHA) and its production method. Further, the present invention relates to a charge control agent, a toner binder, an electrostatic latent image developing toner, and an image forming method and an image forming apparatus using the toner which are employed for a recording method utilizing electrophotograph, electrostatic recording, magnetic recording and the like. Particularly, the present invention relates to a charge control agent, a toner binder, an electrostatic latent image developing toner, an image forming method and an image forming apparatus which are employed for electrophotography, electrostatic recording, electrostatic printing of such as a copying apparatus, a printer, a facsimile and the like for forming an image by previously forming a toner image on an electrostatic latent image carrier (hereinafter, referred to simply as "image carrier") and then transferring the image to a transfer material. More particularly, the present invention relates to a negatively charged charge control agent, a toner binder using the agent, an electrostatic latent image developing toner, and an image forming method and an image forming apparatus using the toner.

2. Related Background Art

So far, many types of microorganism have been reported to produce poly-3-hydroxybutyric acid (PHB) or other PHA and internally accumulate it (Biodegradable Plastic Handbook, Biodegradable Plastic Research Associate, N.T.S. Co., Ltd., p. 178–197 (1995)). Similarly to conventional plastics, these polymers are usable for production of a variety of products by melting and processing. Further, owing to the biodegradability, they have an advantage that they can be completely decomposed by microorganism in the nature and do not have a problem many synthetic polymer compounds of remaining in the natural environments and causing pollution. Also, they are excellent in bio-compatibility and highly expected to be applied to soft members or the like for medical use.

It is known that such microorganism-producing PHA may have various compositions and structures depending on the type of the microorganism to be employed for the production, the culture medium composition, and the culture conditions, and researches regarding mainly control of such compositions and structures have been performed in terms of improvements of the physical properties of PHA.

[1] At first, the biosynthesis of PHA, which is a polymer obtained by polymerizing a monomer unit with a relatively simple structure such as 3-hydroxybutyric acid (hereinafter abbreviated as 3HB) and the like, can be exemplified as follows:

(a) those containing 3HB and 3-hydroxyvaleric acid (hereinafter abbreviated as 3HV); Japanese Patent Publication No. 6-15604, Japanese Patent Publication No. 7-14352, Japanese Patent Publication No. 8-19227, Japanese Patent Application Laid-Open No. 5-7492;

(b) those containing 3HB and 3-hydroxyhexanoic acid (hereinafter abbreviated as 3HHx); Japanese Patent Application Laid-Open No. 5-93049, Japanese Patent Application Laid-Open No. 7-265065;

(c) those containing 3HB and 4-hydroxybutyric acid (hereinafter abbreviated as 4HB); Japanese Patent Application Laid-Open No. 9-191893;

(d) those containing 3-hydroxyalkanoate of 6 to 12 carbons; Japanese Patent Publication No. 2,642,937; and (e) those produced by biosynthesis from a single aliphatic acid as a carbon source (the products are approximately the same as those of (d), Appl. Environ. Microbiol., 58 (2), 746 (1992)). They are all PHA composed of monomer units having alkyl groups in the side chains and synthesized by β-oxidation of hydrocarbons or fatty acid synthesis from saccharides by microorganism, in other words, "usual PHA".

[2] However, taking into account of a wide range application of such microorganism producing PHA ("unusual PHA"), for example, application as functional polymers, PHA into which substituent groups other than alkyl groups are introduced for the side chain is supposed to be extremely advantageous. Examples of the substituent groups are those containing aromatic ring (phenyl, phenoxy, benzoyl and the like), unsaturated hydrocarbons, ester groups, allyl, cyano, halogenated hydrocarbons, epoxide and the like. Among them, PHA having an aromatic ring has actively been investigated.

(a) Those containing phenyl or its partially substituted groups

Makromol. Chem., 191, 1957–1965 (1990) and Macromolecules, 24, 5256–5260 (1991) report production of PHA containing 3-hydroxy-5-phenylvaleric acid as a unit from 5-phenylvaleric acid as a substrate by *Pseudomonas oleovorans*.

Macromolecules, 29, 1762–1766 (1996) reports production of PHA containing 3-hydroxy-5-(4'-tolyl)valeric acid as a unit from 5-(4'-tolyl)valeric acid as a substrate by *Pseudomonas oleovorans*.

Macromolecules, 32, 2889–2895 (1999) reports production of PHA containing 3-hydroxy-5-(2',4'-dinitrophenyl) valeric acid and 3-hydroxy-5-(4'-nitrophenyl)valeric acid as a unit from 5-(2',4'-dinitrophenyl)valeric acid as a substrate by *Pseudomonas oleovorans*.

(b) Those containing phenoxy group or its partially substituted groups

Macromol. Chem. Phys., 195, 1665–1672 (1994) reports production of PHA copolymer of 3-hydroxy-5-phenoxyvaleric acid and 3-hydroxy-9-phenoxynonanoic acid from 11-pheoxyundecanoic acid as a substrate by *Pseudomonas oleovorans*.

Japanese Patent Publication No. 2,989,175 discloses the invention relating to homopolymers of 3-hydroxy-5-(monofluorophenoxy)pentanoate (3H5(MFP)P) unit or 3-hydroxy-5-(difluorophenoxyl)pentanoate (3H5(DFP)P) unit; copolymers containing at least (3H5(MFP)P) unit or (3H5(DFP)P) unit; *Pseudomonas putida* for synthesizing these polymers; and a production method of the polymers using the *Pseudomonas* species and describes the effects that a polymer having phenoxy group substituted with 1 or 2 fluorine atoms in the side chain terminal can be synthesized by metabolizing a long chain aliphatic acid having substituent groups and that the polymer is provided with a high melting point and excellent processibility as well as stereostructure regularlity and water repelling property.

Investigations of cyano- or nitro-substituted substances other than such fluorine-substituted substances have been performed.

Can. J. Microbiol., 41, 32–43 (1995) and Polymer International, 39, 205–213 (1996) report the production of PHA containing 3-hydroxy-p-cyanophenoxyhexanoic acid or 3-hydroxy-p-nitrophenoxyhexanoic acid as a monomer unit from octanoic acid together with p-cyanophenoxyhexanoic acid or p-nitrophenoxyhexanoic acid as substrates using *Pseudomonas oleovorans* ATCC 29347 strain and *Pseudomonas putida* KT 2442 strain.

These reports are useful for obtaining polymers which all contain PHA having aromatic ring in the side chain, dissimilar to general PHA having alkyl groups in the side chain, and are provided with physical properties derived from such PHA.

(3) Also, in a new category, not within an extent to simple alteration of physical properties, productions of PHA having reactive functional groups in the side chains have been investigated to provide new functions based on the functional groups.

For example, Macromolecules, 31, 1480–1486 (1996) and Journal of Polymer Science: Part A: Polymer Chemistry, 36, 2381–2387 (1998) report that PHA containing highly reactive epoxy group in the side chain terminals can be synthesized by synthesizing PHA containing a unit having a vinyl group in the terminal of the side chain and then epoxylating the PHA by an oxidizing agent.

Also, as a synthesis example of PHA containing a unit having thioether expected to have a high reactivity, other than vinyl group, Macromolecules, 32, 8315–8318 (1999) reports production of PHA copolymer of 3-hydroxy-5-(phenylsulfanyl)valeric acid and 3-hydroxy-7-(phenylsulfanyl)valeric acid from 11-(phenylsulfanyl) valeric acid as a substrate by *Pseudomonas putida* 27 N 01 strain.

So far, many methods have been proposed as the electrophotography in the present invention and generally, a typical method is carried out by forming an electric latent image on an image carrier (photosensitive member) by a variety of means using a photoconductive substance, developing the latent image by a toner to obtain a visible image, transferring the toner image to a transfer material such as paper based on the necessity, and then fixing the toner image to a transfer material by heat and/or pressure to obtain a copy. As a method for visualizing the electric latent image, a cascade development method, a magnetic brush development method, a pressurizing development method and the like have been known. Further, a method using a magnetic toner and a rotary development sleeve having a magnetic pole in the center for flying the magnetic toner from the development sleeve to the photosensitive member in a magnetic field has also been employed.

The development systems to be employed for the development of an electrostatic latent image include a two-component development system using a two-component type developer containing a toner and a carrier and a monocomponent type development system using a monocomponent type developer containing only a toner without using a carrier.

A coloring fine particle generally called as a toner contains a binder resin and a coloring material as essential components and a magnetic powder as other components based on the necessity. For providing electric charge to the toner, it is possible to use the charging property of the binder resin itself without using a charge control agent, however in such a case, the stability of the electric charge with the lapse of time and the moisture resistance are inferior to make it impossible to obtain images with excellent quality. Accordingly, normally for the purpose of electric charge retention and charge control of a toner, a charge control agent is added.

Today, charge control agents known in this technical field are, for example, as negative friction charging agents, azo dye-metal complexes, aromatic dicarboxylic acid-metal complexes, salicylic acid derivative-metal complexes and the like. As positive friction charging agents, nigrosine type dyes, triphenylmethane type dyes, a variety of quaternary ammonium salts, and organic tin compounds such as dibutyl tin oxide are well known.

Recently, from a viewpoint of environment preservation, it is globally desired to further decrease wastes and prevent environmental pollution suppression. Such requirements are similarly required in electrophotography and along with the wide spread of imaging apparatuses, printing papers, used waste toner, wastes of copying papers have been increased year by year and in terms of global environment preservation, further decrease of wastes and substance consumption with consideration of environments have been required.

As means for solving the above-described problems, possibility of use of colorless compounds free from heavy metals and polymer type charge control agent has been studied. Examples of such compounds are exemplified in U.S. Pat. No. 4,480,021, U.S. Pat. No. 4,442,189, U.S. Pat. No. 4,925,765, Japanese Patent Application Laid-Open No. 60-108861, Japanese Patent Application Laid-Open No. 61-3149, Japanese Patent Application Laid-Open No. 63-38958, Japanese Patent Application Laid-Open No. 63-88564 and the like and these compounds do not have a sufficient function as the charge control agent and insufficient in the charging capability, the charge rising characteristics, the stability with the lapse of time and environmental stability. Generally, as a polymer charge control agent in the case of providing negative charging property to a toner, copolymers of styrene and/or α-methylstyrene with sulfonic acid group-containing alkyl (meth)acrylate ester or alkyl (meth)acrylamide (Japanese Patent Application Laid-Open No. 7-72658, Japanese Patent Application Laid-Open No. 8-179564, Japanese Patent No. 2,114,410, Japanese Patent No. 2,623,684, and Japanese Patent No. 2,807,795) are employed in many cases. Such materials are advantageous in a point that they are colorless, however a large amount of the materials is required to be added in order to obtain an aimed electric charge and also the sulfonic acid group is an anionic functional group and obviously has moisture absorptivity and thus the materials are supposed to have problems in terms of the moisture resistance. Further, the compatibility of these materials with a binder resin (binder) which is basically nonionic is supposed to become a problem.

From a viewpoint of the environment preservation, decomposable resin with the lapse of time by function of microorganism or the like, that is, biodegradable resin, has been developed and, for example, as described above, there is reported that a variety of microorganism produces biodegradable resin (PHA) having polyester structure and internally accumulates the resin. Such PHA is known to have various compositions and structures depending on the types of microorganism, the culture medium compositions, the culture conditions and the like and so far, researches regarding mainly control of such compositions and structures have been performed in terms of improvements of the physical properties of PHA.

In a field of electrophotography, application of biodegradable resin to binder resin especially in toner production has been proposed. For example, toners of compositions containing biodegradable resin, particularly, polyhydroxybutyric acid, polyhydroxyvaleric acid and their copolymers or blends are disclosed in U.S. Pat. No. 5,004,664. Also, Japanese Patent Application Laid-Open No. 6-289644 discloses electrophotographic toners especially for thermal roll fixation which are characterized in that at least the binder resin contains plant-derived wax and biodegradable resin (e.g., biologically produced polyesters, plant- or animal-derived natural polymer materials) and the plant-derived wax is added in an amount of 5 to 50% by weight in the binder resin. Also, Japanese Patent Application Laid-Open No. 7-120975 discloses electrophotographic toners containing lactic acid-based resin as the binder resin. Further, Japanese Patent Application Laid-Open No. 9-274335 discloses electrostatic latent image developing toners containing polyester resin obtained by dehydration condensation polymerization of compositions containing lactic acid and tri- or higher-functional oxycarboxylic acids and a coloring agent. Also, Japanese Patent Application Laid-Open No. 8-262796 discloses electrophotographic toners containing a binder resin and a coloring agent and characterized in that the binder resin is biodegradable resin (e.g., aliphatic polyester resin and the like) and the coloring agent is a non-aqueous coloring material. Also, Japanese Patent Application Laid-Open No. 9-281746 discloses electrostatic latent image developing toners containing urethane-modified polyester resin obtained by cross-linking polylactic acid with tri- or higher-functional isocyanate and a coloring agent. Any one of the above-described electrophotographic toners contains biodegradable resin and is regarded to be effective to contribute preservation of the environments.

Regarding any one of the above-described electrophotographic toners using biodegradable resin, the charge control agent contains a heavy metal such as chromium, cobalt, nickel, copper, zinc, iron and the like. On the other hand, so far, there has been no report of the case of using biodegradable resin for the charge control agent and development of a material with further consideration of the environments is thus desired.

SUMMARY OF THE INVENTION

Above all, in the case of focusing on PHA containing 3-hydroxy-(phenylsulfanyl)alkanoic acid unit, it is supposed that enthusiastic investigations will be performed enthusiastically in the future to develop functional PHA because of the high reactivity of the sulfanyl group (—S—). However, such a kind of PHA is reported in only one among the above-described examples. Further, the above-described method has a problem that the polymer structure is difficult to be controlled since a carboxylic acid having a long carbon chain is used as a raw material and 3-hydroxyalkanoic acid with a shorter carbon chain than that of the raw material is taken in as a unit by using a β oxidation in which the chain is shortened by two carbons in microorganism.

To solve such a problem, inventors already novel innovative polyhydroxyalkanoates themselves containing a unit having sulfanyl structure (—S—) in the side chains and a production method of the polyhydroxyalkanoates.

The structure of these polyhydroxyalkanoates has sulfur atom in form of sulfanyl (—S—) in the polyhydroxyalkanoate molecule. An object of the present invention is to provide a new structure possible to further improve the physical and chemical properties of a polyhydroxyalkanoate and its production method in order to make the polyhydroxyalkanoate applicable to many uses in a further wide range.

Also, in order to solve the above-described problem, the present invention is to provide a negatively charging charge control agent which, from a functional aspect, is colorless, contains no metal, and has excellent properties (at least any one of high charging capacity, quick charge rising time, excellent stability with the lapse of time, and/or environmental stability) and improved dispersibility; a toner binder containing such a charge control agent; an electrostatic latent image developing toner containing the charge control agent; and an image forming method using such an electrostatic latent image developing toner.

The inventors of the present invention have enthusiastically developed a polyhydroxyalkanoate for the above-described object and consequently achieved the present invention as follows.

That is, a first aspect of the present invention is a polyhydroxyalkanoate itself containing units having the following chemical formulas (1) and (2) and at least one unit selected among four units having chemical formulas (3), (4), (5) and (6), in a molecule.

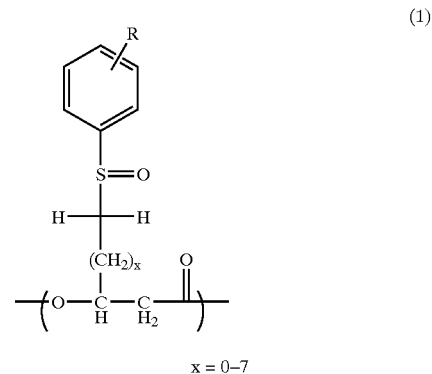

In the above chemical formula, R denotes a substituent optionally selected from H, a halogen atom, CN, $NO_2$, COOR', $SO_2R''$, $CH_3$, $C_2H_5$, $CH_3CH_2CH_2$, $(CH_3)_2CH$ and $(CH_3)_3C$ (R' is H, Na, K, $CH_3$, or $C_2H_5$; and R" is OH, ONa, OK, a halogen atom, $OCH_3$, or $OC_2H_5$); and x denotes at least one optional integer value within the range shown in the chemical formula.

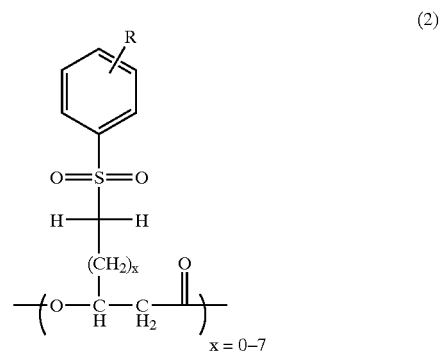

In the above chemical formula, R denotes a substituent optionally selected from H, a halogen atom, CN, $NO_2$, COOR', $SO_2R''$, $CH_3$, $C_2H_5$, $CH_3CH_2CH_2$, $(CH_3)_2CH$ and $(CH_3)_3C$ (R' is H, Na, K, $CH_3$, or $C_2H_5$; and R" is OH, ONa, OK, a halogen atom, $OCH_3$, or $OC_2H_5$); and x denotes at least one optional integer value within the range shown in the chemical formula.

(3)

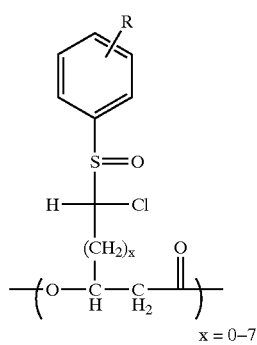

x = 0–7

In the above chemical formula, R denotes a substituent optionally selected from H, a halogen atom, CN, NO$_2$, COOR', SO$_2$R", CH$_3$, C$_2$H$_5$, CH$_3$CH$_2$CH$_2$, (CH$_3$)$_2$CH and (CH$_3$)$_3$C (R' is H, Na, K, CH$_3$, or C$_2$H$_5$; and R" is OH, ONa, OK, a halogen atom, OCH$_3$, or OC$_2$H$_5$); and x denotes at least one optional integer value within the range shown in the chemical formula.

(4)

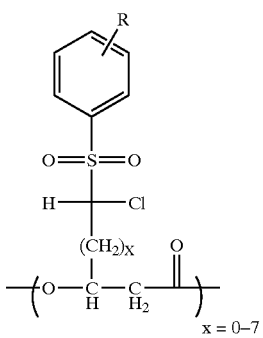

x = 0–7

In the above chemical formula, R denotes a substituent optionally selected from H, a halogen atom, CN, NO$_2$, COOR', SO$_2$R", CH$_3$, C$_2$H$_5$, CH$_3$CH$_2$CH$_2$, (CH$_3$)$_2$CH and (CH$_3$)$_3$C (R' is H, Na, K, CH$_3$, or C$_2$H$_5$; and R" is OH, ONa, OK, a halogen atom, OCH$_3$, or OC$_2$H$_5$); and x denotes at least one optional integer value within the range shown in the chemical formula.

(5)

Cl—S=O structure with Cl, (CH$_2$)$_x$, O...

x = 0–7

In the above chemical formula, R denotes a substituent optionally selected from H, a halogen atom, CN, NO$_2$, COOR', SO$_2$R", CH$_3$, C$_2$H$_5$, CH$_3$CH$_2$CH$_2$, (CH$_3$)$_2$CH and (CH$_3$)$_3$C (R' is H, Na, K, CH$_3$, or C$_2$H$_5$; and R" is OH, ONa, OK, a halogen atom, OCH$_3$, or OC$_2$H$_5$); and x denotes at least one optional integer value within the range shown in the chemical formula.

(6)

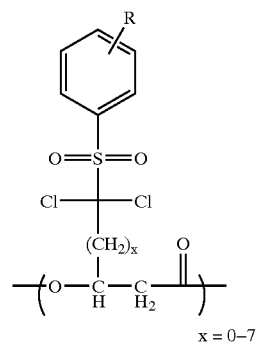

x = 0–7

In the above chemical formula, R denotes a substituent optionally selected from H, a halogen atom, CN, NO$_2$, COOR', SO$_2$R", CH$_3$, C$_2$H$_5$, CH$_3$CH$_2$CH$_2$, (CH$_3$)$_2$CH and (CH$_3$)$_3$C (R' is H, Na, K, CH$_3$, or C$_2$H$_5$; and R" is OH, ONa, OK, a halogen atom, OCH$_3$, or OC$_2$H$_5$); and x denotes at least one optional integer value within the range shown in the chemical formula.

Among novel polyhydroxyalkanoates of the present invention, the following three kinds of polyhydroxyalkanoates can particularly be exemplified.

A first example of polyhydroxyalkanoates of the present invention is a polyhydroxyalkanoate containing, in a molecule, units having the following chemical formulas (9) and (10) and at least one selected from four kinds of units having the following chemical formulas (11), (12), (13), and (14), among 3-hydroxy-5-(phenylsulfinyl)valeric acid unit defined as chemical formula (9), 3-hydroxy-5-(phenylsulfonyl)valeric acid unit defined as chemical formula (10), 5-chloro-3-hydroxy-5-(phenylsulfinyl)valeric acid unit defined as chemical formula (11), 5-chloro-3-hydroxy-5-(phenylsulfonyl)valeric acid unit defined as chemical formula (12), 5,5-dichloro-3-hydroxy-5-(phenylsulfinyl)valeric acid unit defined as chemical formula (13), and 5,5-dichloro-3-hydroxy-5-(phenylsulfonyl)valeric acid unit defined as chemical formula (14).

(9)

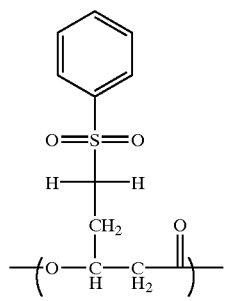
(10)

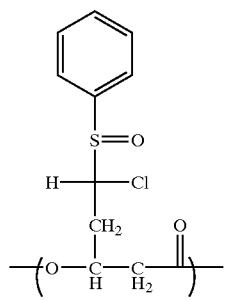
(11)

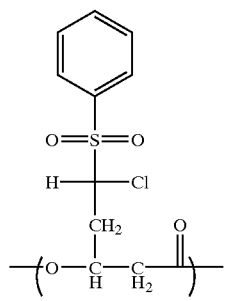
(12)

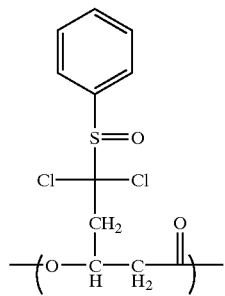
(13)

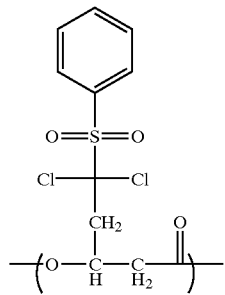
(14)

A second example of polyhydroxyalkanoates of the present invention is a polyhydroxyalkanoate containing, in a molecule, units having the following chemical formulas (15) and (16) and at least one selected from four kinds of units having the following chemical formulas (17), (18), (19), and (20) among 3-hydroxy-4-(phenylsulfinyl)butyric acid unit defined as chemical formula (15), 3-hydroxy-4-(phenylsulfonyl)butyric acid unit defined as chemical formula (16), 4-chloro-3-hydroxy-4-(phenylsulfinyl)butyric acid unit defined as chemical formula (17), 4-chloro-3-hydroxy-4-(phenylsulfonyl)butyric acid unit defined as chemical formula (18), 4,4-dichloro-3-hydroxy-4-(phenylsulfinyl)butyric acid unit defined as chemical formula (19), and 4,4-dichloro-3-hydroxy-4-(phenylsulfonyl)butyric acid unit defined as chemical formula (20).

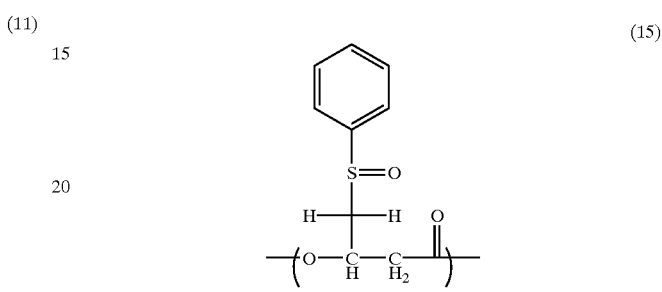
(15)

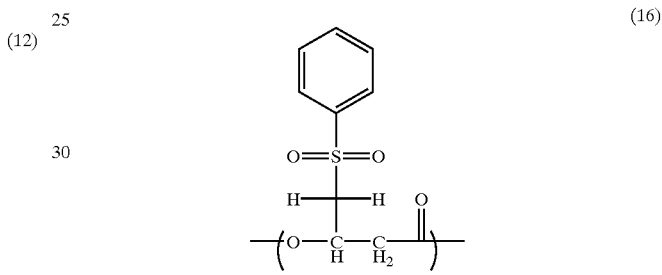
(16)

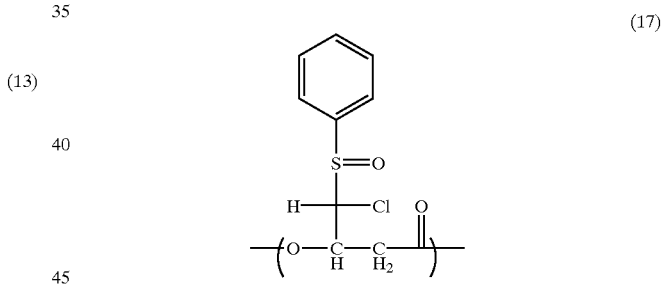
(17)

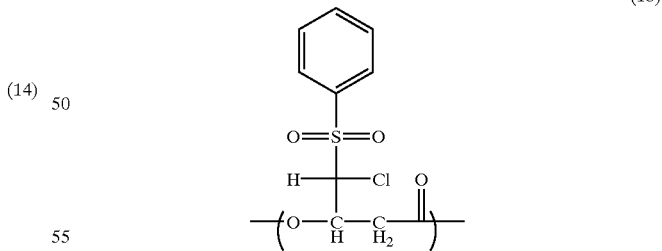
(18)

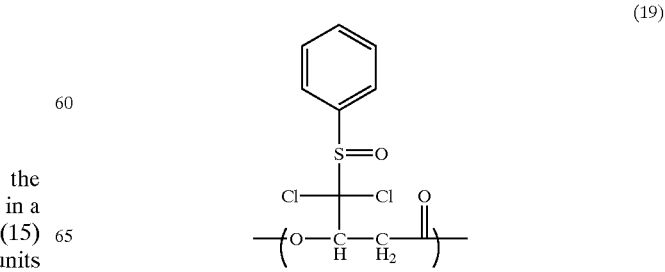
(19)

(20)

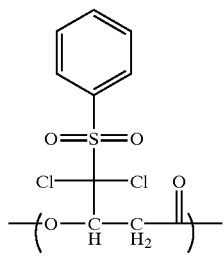

A third example of polyhydroxyalkanoates of the invention is a polyhydroxyalkanoate containing, in a molecule, units having the following chemical formulas (21) and (22) and at least one selected from four kinds of units having the following chemical formulas (23), (24), (25), and (26), among 3-hydroxy-5-[(4-fluorophenyl)sulfinyl]valeric acid unit defined as chemical formula (21), 3-hydroxy-5-[(4-fluorophenyl)sulfonyl]valeric acid unit defined as chemical formula (22), 5-chloro-3-hydroxy-5-[(4-fluorophenyl)sulfinyl]valeric acid unit defined as chemical formula (23), 5-chloro-3-hydroxy-5-[(4-fluorophenyl)sulfonyl]valeric acid unit defined as chemical formula (24), 5,5-dichloro-3-hydroxy-5-[(4-fluorophenyl)sulfinyl]valeric acid unit defined as chemical formula (25), 5,5-dichloro-3-hydroxy-5-[(4-fluorophenyl)sulfonyl]valeric acid unit defined as chemical formula (26).

(21)

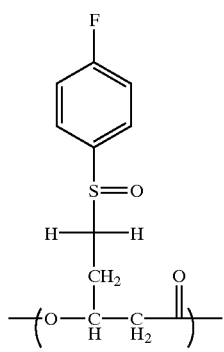

(22)

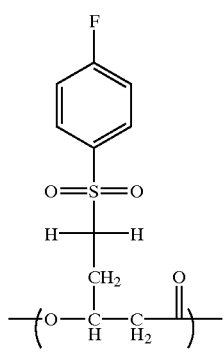

(23)

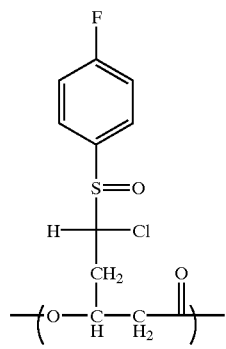

(24)

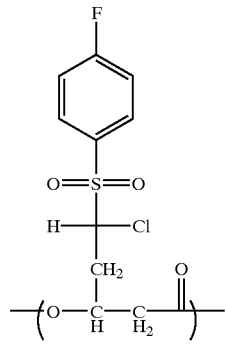

(25)

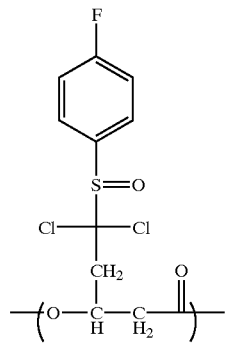

(26)

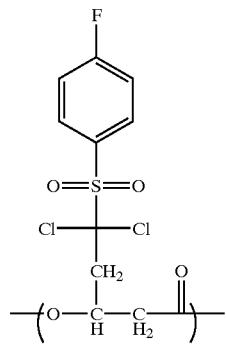

The polyhydroxyalkanoates of the present invention may contains at least one of units defined as the following chemical formulas (7) and (8), besides the units defined as the chemical formulas (1), (2), (3), (4), (5), and (6).

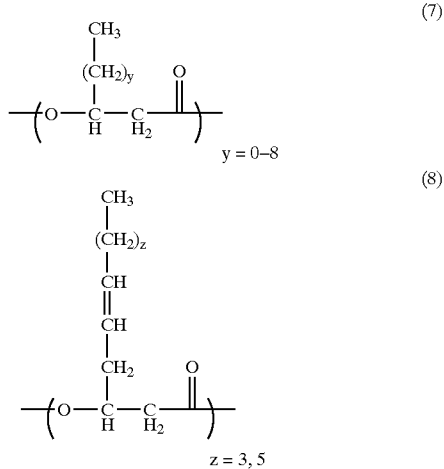

The above formula, y and z independently denote at least one optional integer value within a range shown in the chemical formula, independently of the units defined as the chemical formulas (1), (2), (3)), (4), (5) and (6).

The polyhydroxyalkanoates of the present invention have a number average molecular weight in a range from 1,000 to 500,000.

In addition to the above, the present invention also provides a method for producing the above-described PHA of the present invention. That is, the production method of the polyhydroxyalkanoates of the present invention is a production method of a polyhydroxyalkanoate having any of the above-described structures and comprises a step (step 1) of culturing a microorganism in a culture medium containing at least one kind of compounds defined as the chemical formulas (27) and (28):

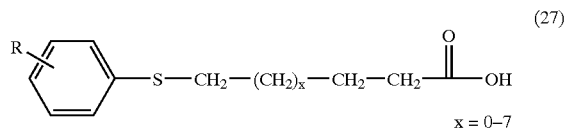

wherein R denotes a substituent optionally selected from H, a halogen atom, CN, $NO_2$, COOR', $SO_2R''$, $CH_3$, $C_2H_5$, $CH_3CH_2CH_2$, $(CH_3)_2CH$ and $(CH_3)_3C$ (R' is H, Na, K, $CH_3$, or $C_2H_5$; and R" is OH, ONa, OK, a halogen atom, $OCH_3$, or $OC_2H_5$); and x denotes at least one optional integer value within the range shown in the chemical formula; and

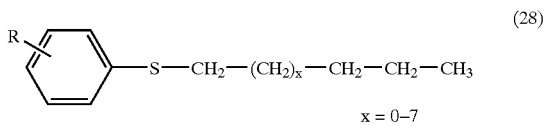

wherein R1 denotes a substituent on an aromatic ring and is optionally selected from H, a halogen atom, CN, $NO_2$, $CH_3$, $C_2H_5$, $CH_3CH_2CH_2$, $(CH_3)_2CH$ and $(CH_3)_3C$; and x denotes at least one optional integer value within the range shown in the chemical formula; and a step (step 2) of treating the polyhydroxyalkanoate produced by the cultured microorganism with sodium hypochlorite to produce the polyhydroxyalkanoate according to the present invention.

Further, between the step 1 and the step 2, the production method of the present invention may further comprise a step of separating the polyhydroxyalkanoate from the cultured microorganism cells. The step of separating the polyhydroxyalkanoate from the cultured microorganism cells may be a step of pulverizing the cultured microorganism cells or a step of extracting the polyhydroxyalkanoate from the microorganism cells with a solvent in which the polyhydroxyalkanoate is soluble. The step of pulverizing the microorganism cells may be carried out by employing any of an ultrasonic pulverization method, a homogenizer method, a pressure pulverization method, a bead impact method, a grinding method, a milling method, and a freezing and thawing method. On the other hand, the step of extracting the polyhydroxyalkanoate from microorganism cells with a solvent in which the polyhydroxyalkanoate is soluble may be carried out using a solvent selected from chloroform, dioxane, tetrahydrofuran, acetonitrile, and acetone.

Additionally, the PHA production method of the present invention is a production method characterized in that polypeptone is contained in the culture medium in the step 1.

Further, the production method is characterized in that yeast extract is contained in the culture medium in the step 1.

Or, the production method is characterized in that saccharides are contained in the culture medium in the step 1. In this case, the saccharides are preferably one or more compounds selected from glyceraldehyde, erythrose, arabinose, xylose, glucose, galactose, mannose, fructose, glycerol, erythritol, xylitol, gluconic acid, glucuronic acid, galacturonic acid, maltose, sucrose, and lactose.

Furthermore, the production method is characterized in that an organic acid or its salt is contained in the culture medium of the step 1. In this case the organic acid or its salt is preferably one or more compounds selected from a group consisting of pyruvic acid, malic acid, lactic acid, citric acid, succinic acid and their salts.

Also, the production method is characterized in that amino acid or its salt is contained in the culture medium of the step 1. In this case the amino acids or its salt is preferably one or more compounds selected from the group consisting of glutamic acid, aspartic acid and their salts.

Or, the production method is characterized in that a straight chain alkanoic acid of 4 to 12 carbons or its salt is contained in the culture medium of the step 1.

In the case of culturing a microorganism in a culture medium containing at least one kind of the compounds having the chemical formula (28), in the step 1, the microorgnism preferably has alkanemonooxygenase. In this case, in order to effectively introduce alkane oxidation system, there may further provide a step of culturing the microorganism in a culture medium containing dicyclopropylketone.

The production method of PHA of the present invention is characterized in that the culture of the microorganism in the step 1 comprises a step (step 1-1) of culturing the microorganism in a culture medium containing at least one kind of compounds defined as chemical formula (27) and polypeptone and successively a step (step 1-2) of culturing the microorganism cultured in the step 1-1 in a culture medium containing at least one kind of compounds defined as chemical formula (27) and an organic acid or its salt. In this embodiment, the foregoing organic acid or its salt are preferably one or more compounds selected from pyruvic acid, malic acid, lactic acid, citric acid, succinic acid and their salts. In this case, the culture medium to be employed for the step 1-2 is further preferable to contain no nitrogen source.

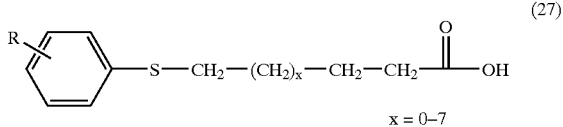

(27)

x = 0–7

In the above chemical formula, R denotes a substituent optionally selected from H, a halogen atom, CN, $NO_2$, COOR', $SO_2R''$ $CH_3$, $C_2H_5$, $CH_3CH_2CH_2$, $(CH_3)_2CH$ and $(CH_3)_3C$ (R' is H, Na, K, $CH_3$, or $C_2H_5$; and R" is OH, ONa, OK, a halogen atom, $OCH_3$, or $OC_2H_5$); and x denotes at least one optional integer value within the range shown in the chemical formula.

Alternatively, the production method of PHA of the present invention is characterized in that the culture of the microorganism in the step 1 comprises a step (step 1-3) of culturing the microorganism in a culture medium containing at least one kind of compounds defined as the following chemical formula (27) and saccharide, and successively a step (step 1-4) of culturing microorganism cultured in the step 1-3 in a culture medium containing at least one kind of compounds defined as the following chemical formula (27) and saccharide. In this embodiment, the foregoing saccharide is preferably one or more compounds selected from the group consisting of glyceraldehyde, erythrose, arabinose, xylose, glucose, galactose, mannose, fructose, glycerol, erythritol, xylitol, gluconic acid, glucuronic acid, galacturonic acid, maltose, sucrose, and lactose. In this case the culture medium employed in the step 1-4 is further preferable to contain no nitrogen source.

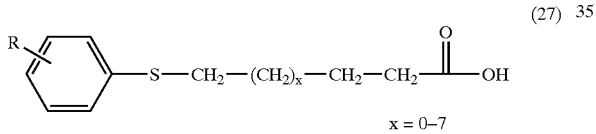

(27)

x = 0–7

In the above chemical formula, R denotes a substituent optionally selected from H, a halogen atom, CN, $NO_2$, COOR', $SO_2R''$, $CH_3$, $C_2H_5$, $CH_3CH_2CH_2$, $(CH_3)_2CH$ and $(CH_3)_3C$ (R' is H, Na, K, $CH_3$, or $C_2H_5$; and R" is OH, ONa, OK, a halogen atom, $OCH_3$, or $OC_2H_5$); and x denotes at least one optional integer value within the range shown in the chemical formula.

A novel polyhydroxyalkanoate of the present invention contains a hydroxyalkanoic acid which becomes a monomer unit having sulfinyl (—SO—) or sulfonyl (—$SO_2$—) structure in which the methylene site at the α-position of the sulfur atom is substituted with chlorine atom. Owing to such a structure, the polyhydroxyalkanoate is provided with physical and chemical properties remarkably different from those of conventionally known polyhydroxyalkanoates produced by microorganism. The polyhydroxyalkanoate is produced in steps of culturing microorganism capable of producing a polyhydroxyalkanoate in a culture medium containing the foregoing hydroxyalkanoic acid and a carbon source for propagation, and treating the polyhydroxyalkanoate produced by the cultured microorganism with sodium hypochlorite.

In the PHA production method of the present invention with the constitution as described above, the microorganism to be employed in the step 1 is preferably microorganism belonging to *Pseudomonas* species. For example, the foregoing microorganism to be employed in the step 1 is further preferably selected from *Pseudomonas cichorii* YN2 strain (FERM BP-7375), *Pseudomonas cichorii* H45 strain (FERM BP-7374), and *Pseudomonas jessenii* P161 strain (FERM BP-7376).

The inventors of the present invention have enthusiastically investigated to develop a highly capable charge control agent practically colorless and free from a metal and finally achieved the present invention.

That is, the present invention is PHA comprising units selected from units having the following chemical formulas:

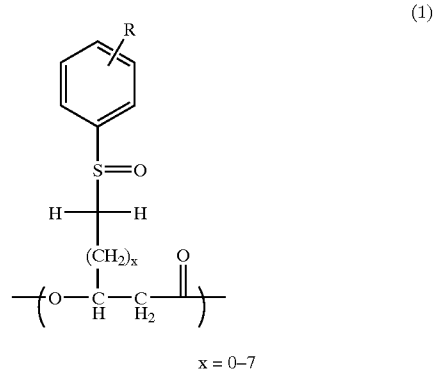

(1)

x = 0–7 in the above formula, R denotes a substituent optionally selected from H, a halogen atom, CN, $NO_2$, COOR', $SO_2R''$, $CH_3$, $C_2H_5$, $CH_3CH_2CH_2$, $(CH_3)_2CH$ and $(CH_3)_3C$ (R' is H, Na, K, $CH_3$, or $C_2H_5$; and R" is OH, ONa, OK, a halogen atom, $OCH_3$, or $OC_2H_5$); and x denotes at least one optional integer value within the range shown in the chemical formula;

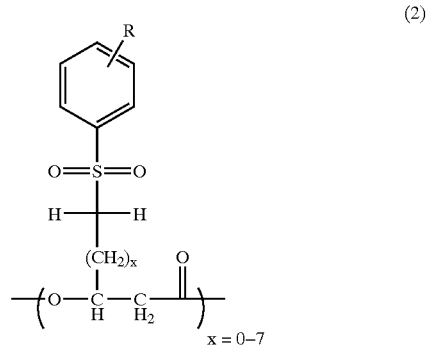

(2)

x = 0–7 in the above formula, R denotes a substituent optionally selected from H, a halogen atom, CN, $NO_2$, COOR', $SO_2R''$, $CH_3$, $C_2H_5$, $CH_3CH_2CH_2$, $(CH_3)_2CH$ and $(CH_3)_3C$ (R' is H, Na, K, $CH_3$, or $C_2H_5$; and R" is OH, ONa, OK, a halogen atom, $OCH_3$, or $OC_2H_5$); and x denotes at least one optional integer value within the range shown in the chemical formula;

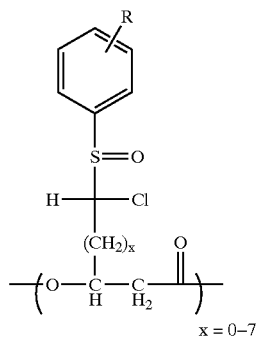

(3)

x = 0–7 in the above formula, R denotes a substituent optionally selected from H, a halogen atom, CN, $NO_2$, $COOR'$, $SO_2R''$, $CH_3$, $C_2H_5$, $CH_3CH_2CH_2$, $(CH_3)_2CH$ and $(CH_3)_3C$ ($R'$ is H, Na, K, $CH_3$, or $C_2H_5$; and $R''$ is OH, ONa, OK, a halogen atom, $OCH_3$, or $OC_2H_5$); and x denotes at least one optional integer value within the range shown in the chemical formula;

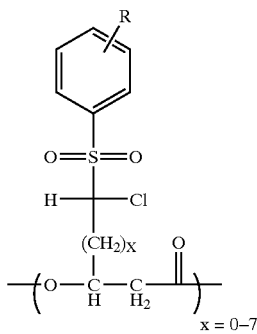

(4)

x = 0–7 in the above formula, R denotes a substituent optionally selected from H, a halogen atom, CN, $NO_2$, $COOR'$, $SO_2R''$, $CH_3$, $C_2H_5$, $CH_3CH_2CH_2$, $(CH_3)_2CH$ and $(CH_3)_3C$ ($R'$ is H, Na, K, $CH_3$, or $C_2H_5$; and $R''$ is OH, ONa, OK, a halogen atom, $OCH_3$, or $OC_2H_5$); and x denotes at least one optional integer value within the range shown in the chemical formula;

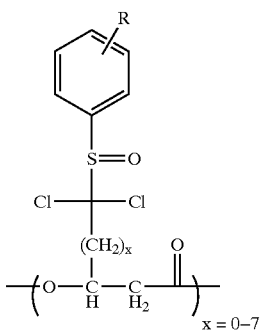

(5)

x = 0–7 in the above formula, R denotes a substituent optionally selected from H, a halogen atom, CN, $NO_2$, $COOR'$, $SO_2R''$, $CH_3$, $C_2H_5$, $CH_3CH_2CH_2$, $(CH_3)_2CH$ and $(CH_3)_3C$ ($R'$ is H, Na, K, $CH_3$, or $C_2H_5$; and $R''$ is OH, ONa, OK, a halogen atom, $OCH_3$, or $OC_2H_5$); and x denotes at least one optional integer value within the range shown in the chemical formula; and

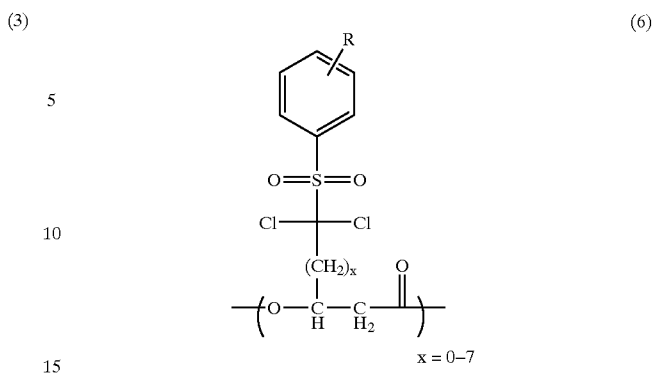

(6)

x = 0–7 in the above formula, R denotes a substituent optionally selected from H, a halogen atom, CN, $NO_2$, $COOR'$, $SO_2R''$, $CH_3$, $C_2H_5$, $CH_3CH_2CH_2$, $(CH_3)_2CH$ and $(CH_3)_3C$ ($R'$ is H, Na, K, $CH_3$, or $C_2H_5$; and $R''$ is OH, ONa, OK, a halogen atom, $OCH_3$, or $OC_2H_5$); and x denotes at least one optional integer value within the range shown in the chemical formula.

The foregoing PHA may further comprise at least one of units having the following chemical formulas (7) and (8), besides the units having the chemical formulas (1), (2), (3), (4), (5) and (6).

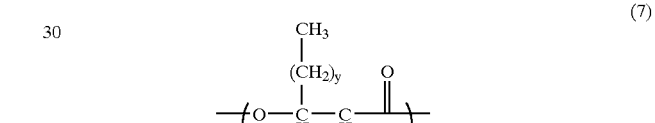

(7)

y = 0–8

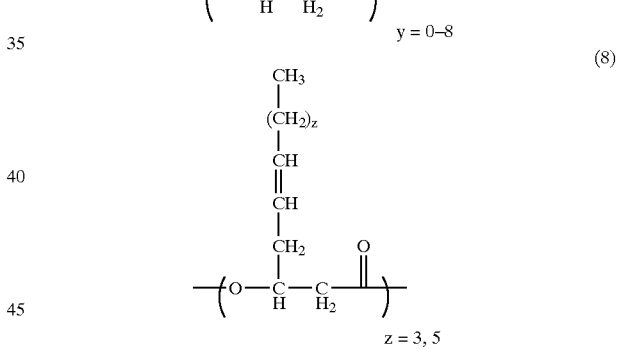

(8)

z = 3, 5

In the above formulas, y and z independently denote at least one optional integer value within a range shown in the chemical formula, independently of the units defined as the chemical formulas (1), (2), (3), (4), (5) and (6).

The PHA contained in the charge control agent of the present invention preferably has a number average molecular weight in a range from 1,000 to 500,000.

Further, the present invention provides a toner binder containing the foregoing charge control agent of the present invention.

Further, the present invention provides an electrostatic latent image developing toner containing at least a binder resin, a coloring agent, and the foregoing charge control agent of the present invention.

Also, the present invention provides an image forming method comprising a step of charging an electrostatic latent image carrier by applying voltage to a charging member from the outside, a step forming an electrostatic latent image on the charged electrostatic latent image carrier, a development step of developing the electrostatic latent image by an electrostatic latent image developing toner to form a toner image on the electrostatic latent image carrier, a transfer step of transferring the toner image on the electrostatic latent image carrier to a recording material, and a fixation step of fixing the toner image on the recording material by heating, wherein that an electrostatic latent image developing toner containing at least a binder resin, a coloring agent and the foregoing charge control agent of the present invention is employed.

Further, the present invention provide an image forming method comprising a step of charging an electrostatic latent image carrier by applying voltage to a charging member from the outside, a step forming an electrostatic latent image on the charged electrostatic latent image carrier, a development step of developing the electrostatic latent image by an electrostatic latent image developing toner to form a toner image on the electrostatic latent image carrier, a first transfer step of transferring the toner image on the electrostatic latent image carrier to an intermediate transfer member, a second transfer step of transferring the toner image on the intermediate transfer member to a recording material, and a fixation step of fixing the toner image on the recording material by heating, wherein an electrostatic latent image developing toner containing at least a binder resin, a coloring agent and the foregoing charge control agent of the present invention is employed.

Further, the present invention provides an image forming apparatus for forming an image using an electrostatic latent image developing toner containing the charge control agent of the present invention.

More particularly, the image forming apparatus of the present invention comprises means for charging an electrostatic latent image carrier by applying voltage to a charging member from the outside, means for forming an electrostatic latent image on the charged electrostatic latent image carrier, development means for developing the electrostatic latent image by an electrostatic latent image developing toner to form a toner image on the electrostatic latent image carrier, transfer means for transferring the toner image on the electrostatic latent image carrier to a recording material, and fixation means for fixing the toner image on the recording material by heating, wherein an electrostatic latent image developing toner containing at least a binder resin, a coloring agent and the foregoing charge control agent of the present invention is employed; and the image forming apparatus of the present invention comprises means for charging an electrostatic latent image carrier by applying voltage to a charging member from the outside, means for forming an electrostatic latent image on the charged electrostatic latent image carrier, development means for developing the electrostatic latent image by an electrostatic latent image developing toner to form a toner image on the electrostatic latent image carrier, first transfer means for transferring the toner image on the electrostatic latent image carrier to an intermediate transfer member, second transfer means for transferring the toner image on the intermediate transfer member to a recording material, and fixation means for fixing the toner image on the recording material by heating, wherein an electrostatic latent image developing toner containing at least a binder resin, a coloring agent and the foregoing charge control agent of the invention is employed.

According to the methods of the invention, a polyhydroxyalkanoate comprising units defined as the chemical formulas (1) and (2) and at least one among four kinds of units defined as the chemical formulas (3), (4), (5) and (6) and its production method are provided.

Further, according to the present invention, addition of at least one compound of the present invention as a charge control agent to an electrostatic latent image developing toner composition makes it possible to provide an electrostatic latent image developing toner excellent in charging properties, highly suitable for electrophotographic process, having improved dispersibility of the compound in toner resin and spent-property and giving excellent transferring properties without image fogging even in the case of high power output by an image forming apparatus. Further, since the charge control agent to be employed in the present invention is colorless or scarcely colored, any optional coloring agent may be selected corresponding to the hue required for a color toner, and the charge control agent of the present invention does not inhibit the hue which a dye or a pigment intrinsically has. Additionally, the electrostatic latent image developing toner of the present invention contains no heavy metal and therefore is significantly safe and biodegradable, the electrostatic latent image developing toner has a remarkable industrial advantages that it requires no combustion treatment and that it can avoid atmospheric air pollution and global warming phenomena from an aspect of environmental preservation.

The above and other objects, effects, features and advantages of the present invention will become more apparent from the following description of embodiments thereof taken in conjunction with the accompanying drawings.

DESCRIPTION OF THE PREFERRED EMBODIMENTS

Figure 1:
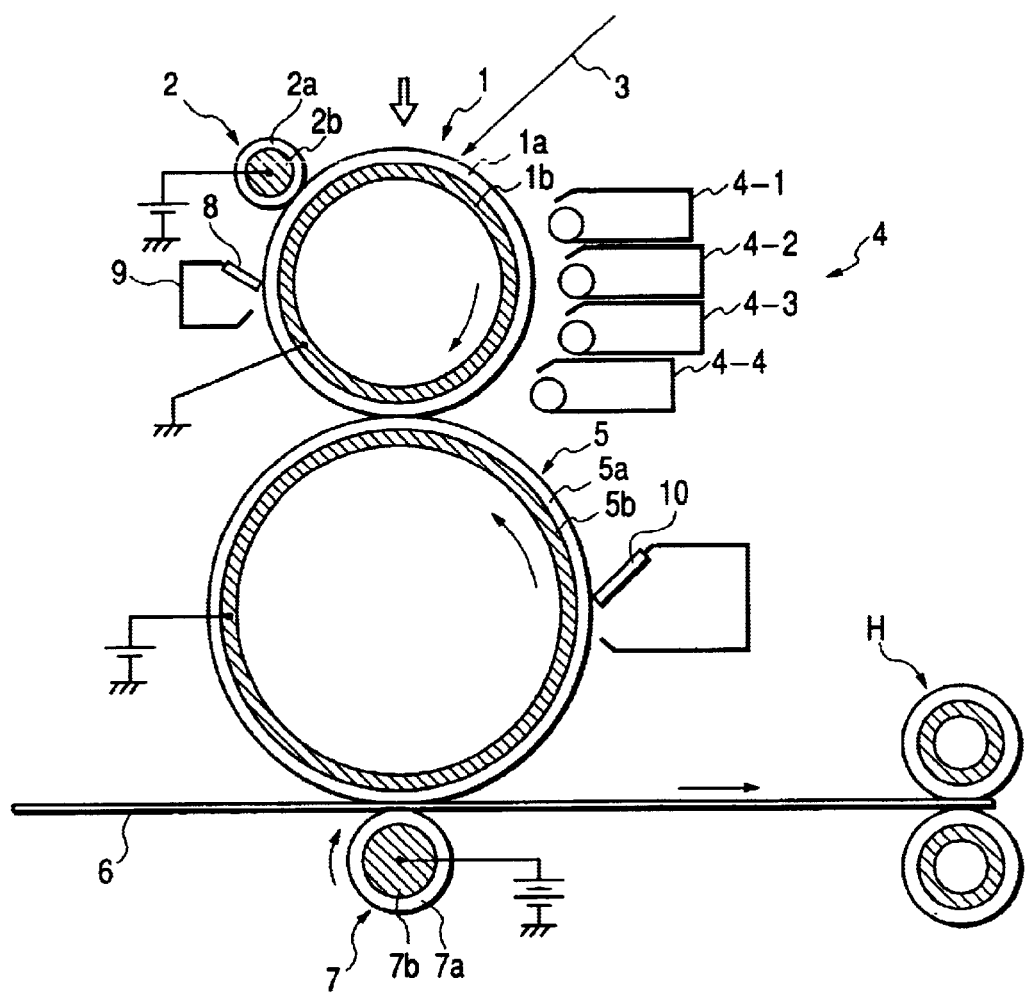
FIG. 1 is a schematic illustration of an image forming apparatus employed for Example 39 to Example 56 and Comparative Example 7 to Comparative Example 12.

Hereinafter, the present invention will be described in details.

A new polyhydroxyalkanoate of the present invention comprise sulfoxide structure (—SO—) and sulfone structure (—SO$_2$—) in monomer units of hydroxyalkanoic acid and the monomer units in which hydrogen atom(s) of the methylene site at the α-position of the sulfur atom is/are substituted with chlorine atom(s).

The polyhydroxyalkanoate of the invention is produced in two steps: a step of carrying out culture of a microorganism capable of producing PHA in a culture medium containing a carbon source for propagation in addition to ω-(substituted phenylsulfanyl)alkanoic acid or 1-(substituted phenylsulfanyl)alkane as a raw material; and a step of treating the polyhydroxyalkanoate containing units having the substituted phenylsulfanyl group in the side chain terminals, produced in the culture step and accumulated in the microorganism, with sodium hypochlorite. That is, in the PHA production method of the present invention, as an intermediate raw material, PHA containing a unit having the substituted phenylsulfanyl group in the side chain terminals is produced by the microorganism and the sulfanyl group (—S—) is oxidized using sodium hypochlorite to convert the intermediate raw material into aimed PHA consisting of sulfoxide structure (—SO—), sulfone structure (—SO$_2$—) and a structure in which hydrogen atom(s) of the methylene site at the α-position of the sulfur atom is/are substituted with chlorine atom(s).

Each production method will be described in details below.

(Method of Producing PHA Using ω-(Substituted Phenylsulfanyl)alkanoic Acid as a Raw Material)

The method of producing PHA using ω-(substituted phenylsulfanyl)alkanoic acid as a raw material according to the present invention will be described below in details.

(Carboxylic Acid Derivative)

A ω-(substituted phenylsulfanyl)alkanoic acid to be employed in the present invention is a compound defined as the following chemical formula (27).

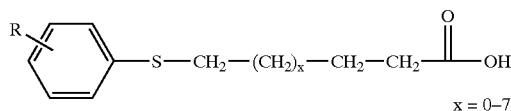

(27)

x = 0–7

In the above formula, R denotes a substituent optionally selected from H, a halogen atom, CN, NO$_2$, COOR', SO$_2$R", CH$_3$, C$_2$H$_5$, CH$_3$CH$_2$CH$_2$, (CH$_3$)$_2$CH and (CH$_3$)$_3$C (R' is H, Na, K, CH$_3$, or C$_2$H$_5$; and R" is OH, ONa, OK, a halogen atom, OCH$_3$, or OC$_2$H$_5$); and x denotes at least one optional integer value within the range shown in the chemical formula.

This compound is produced, for example, by reacting a compound having the chemical formula (29):

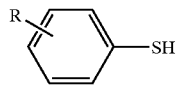

(29)

(in the above formula, R denotes the same as R in the formula (27)) with ω-bromoalkanoic acid ester to synthesize ω-(substituted phenylsulfanyl)alkanoic acid ester and then hydrolyzing the ester.

The microorganism to be employed for a method of the present invention may be any microorganism capable of producing polyhydroxyalkanoate by culture in a culture medium containing the compound defined as the chemical formula (27) to be a precursor for production of the above-described polyhydroxyalkanoate of the present invention by treatment with sodium hypochlorite, and an example of the microorganism is microorganism belonging to *Pseudomonas* species. More particularly, microorganism is *Pseudomonas cichorii* YN2 (FERM BP-7375), *Pseudomonas cichorii* H45 (FERM BP-7374), and *Pseudomonas jessenii* P161 (FERM BP-7376). These three types of microorganism stains have been deposited in International Patent Organism Depositary of Insititute of Advanced Industrial Science and Technology (former National Institute of Biosciene and Human Technology, Agency of Industral Science and Technology) and described in Japanese Patent Application No. 11-371863.

There will be given details concerning strains YN2, H45, and P161.

<Bacteriological Properties of Strain YN2>
(1) Morphological Properties
Shape and size of cells: 0.8 μm×1.5 to 2.0 μm
Polymorphism of cells: negative
Mobility: motile
Sporulation: negative
Gram staining: negative
Colony shape: circular; entire, smooth margin; low convex; smooth surface; glossy; translucent
(2) Physiological Properties
Catalase: positive
Oxidase: positive
O/F test: oxidative (non-fermentative)
Nitrate reduction: negative
Indole production: positive
Acid production from glucose: negative
Arginine dihydrolase: negative
Urease: negative
Esculin hydrolysis: negative
Gelatin hydrolysis: negative
β-Galactosidase: negative
Fluorescent pigment production on King's B agar: positive
Growth under 4% NaCl: positive (weak growth)
Poly-β-hydroxybutyrate accumulation: negative (*)
Tween 80 hydrolysis: positive
(*) Colonies cultured on nutrient agar were stained with Sudan Black for determination.
(3) Substrate Assimilation
Glucose: positive
L-Arabinose: positive
D-Mannose: negative
D-Mannitol: negative
N-Acetyl-D-glucosamine: negative
Maltose: negative
Potassium gluconate: positive
n-Caprate: positive
Adipate: negative
dl-Malate: positive
Sodium citrate: positive
Phenyl acetate: positive
<Bacteriological Properties of Strain H45>
(1) Morphological Properties
Shape and size of cells: rod, 0.8 μm×1.0 to 1.2 μm
Polymorphism of cells: negative
Mobility: motile
Sporulation: negative
Gram staining: negative
Colony shape: circular; entire, smooth margin; low convex; smooth surface; glossy; cream-colored
(2) Physiological Properties
Catalase: positive
Oxidase: positive
O/F test: oxidative
Nitrate reduction: negative
Indole production: negative
Acid production from glucose: negative Arginine dihydrolase: negative
Urease: negative
Esculin hydrolysis: negative
Gelatin hydrolysis: negative
β-Galactosidase: negative
Fluorescent pigment production on King's B agar: positive
Growth under 4% NaCl: negative
Poly-β-hydroxybutyrate accumulation: negative
(3) Ability to Assimilate Substrates
Glucose: positive
L-Arabinose: negative
D-Mannose: positive
D-Mannitol: positive
N-Acetyl-D-glucosamine: positive
Maltose: negative
Potassium gluconate: positive
n-Caprate: positive
Adipate: negative
dl-Malate: positive
Sodium citrate: positive
Phenyl acetate: positive
<Bacteriological Properties of the Strain P161>
(1) Morphological Properties
Shape and size of cells: spheres, φ0.6 μm rods, 0.6 μm×1.5 to 2.0 μm
Polymorphism of cells: elongated form
Mobility: motile
Sporulation: negative
Gram staining: negative
Colony shape: circle; entire, smooth margin; low convex; smooth surface; pale yellow
(2) Physiological Properties
Catalase: positive
Oxidase: positive
O/F test: oxidative
Nitrate reduction: positive
Indole production: negative
Acid production from glucose: negative
Arginine dihydrolase: positive
Urease: negative
Esculin hydrolysis: negative
Gelatin hydrolysis: negative
β-Galactosidase: negative
Fluorescent pigment production on King's B agar: positive
(3) Substrate Assimilation
Glucose: positive
L-Arabinose: positive
D-Mannose: positive
D-Mannitol: positive
N-Acetyl-D-glucosamine: positive
Maltose: negative
Potassium gluconate: positive
n-Caprate: positive
Adipate: negative
dl-Malate: positive
Sodium citrate: positive
Phenyl acetate: positive
(Culture Step)

For common culture of microorganism to be used for the polyhydroxyalkanoate production method according to the present invention, for example, production of preservation strains and propagation for ensuring the number of cells and active state necessary for producing the polyhydroxyalkanoate, a culture medium containing components required to propagate the microorganism to be employed is properly selected. For example, any types of general natural culture media (meat juice media, yeast extract media and the like) and artificial media containing nutrient sources can be employed, unless they cause no bad effects on growth and survival of microorganism. The culture conditions such as temperature, ventilation, agitation and the like may properly be selected depending on the microorganism to be employed.

In order to produce an aimed polyhydroxyalkanoate using such polyhydroxyalkanoate-producing microorganism as described above, an inorganic medium containing at least a compound defined as the foregoing chemical formula (27) corresponding to the monomer unit as a raw material for polyhydroxyalkanoate production and a carbon source for propagation of the microorganism may be used.

The compound defined as the foregoing chemical formula (27) is contained in the culture medium at a ratio preferably from 0.01% to 1% (w/v), more preferably from 0.02% to 0.2% (w/v) based on the culture medium. The water-solubility of the compound and the carbon source contained in the culture medium is not necessarily high, in the case the microorganism described in the present invention is employed, there is no problem even if they are in suspended state. Further, in some cases, the compound may be contained in the culture medium while being dissolved or suspended in a solvent such as 1-hexadecene and n-hexadecane. In this case, the concentration of the solvent is required to be 3% or lower in the culture medium solution.

As the carbon source for propagation, nutrients such as yeast extract, polypeptone, meat extract and the like may be used and further the substances may be selected, based on the usability as substrates for the microorganism strains to be used from saccharides, organic acids produced as intermediates in TCA circuit, organic acids produced by one-step or two-step biochemical reaction from TCA circuit, their salts, aminoacids, their salts, and alkanoic acids and their salts.

Among the above substances, saccharides preferable to be used are one or more compounds selected from aldoses such as glyceraldehyde, erythrose, arabinose, xylose, glucose, galactose, mannose and fructose; alditols such as glycerol, erythritol and xylitol; aldonic acids such as gluconic acid; uronic acids such as glucuronic acid and galacturonic acid; and disaccharides such as maltose, sucrose and lactose.

The organic acids and their salts preferable to be used are one or more compounds selected from pyruvic acid, malic acid, lactic acid, citric acid, succinic acid and their salts.

The amino acids and their salts preferable to be used are one or more compounds selected from glutamic acid, aspartic acid, and their salts.

These substrates are contained in the culture medium at a ratio generally from 0.1% to 5% (w/v), preferably 0.2% to 2% (w/v) based on the culture medium.

The method for producing and accumulating the polyhydroxyalkanoate by and in the microorganism may be carried out by sufficiently propagating the microorganism once and then transferring the strains to a culture medium with a restricted nitrogen source such as ammonium chloride and further carrying out propagation in the state that compounds to be substrates of the aimed units are added to improve the productivity in some cases. More particularly, a multistep system comprising a plurality of stages of the foregoing steps arranged in series can be exemplified.

For example, a method comprises a step (step 1-1) for culturing the microorganism in a culture medium containing the compound defined as the chemical formula (27) and polypeptone, which is continued from the later stage of the logarithmic growth to the steady growth stage, and recovering the strains by centrifugal separation; and then a step (step 1-2) for further culturing the microorganism strains, which are propagated in the step 1-1, in a culture medium containing the compound defined as the chemical formula (27), and an organic acid or its salt, but no nitrogen source; or a method comprises a step (step 1-3) for culturing the microorganism in a culture medium containing the compound defined as the chemical formula (27) and saccharides, which is continued from the later stage of the logarithmic growth to the steady growth stage, and recovering the strains by centrifugal separation; and then a step (step 1-4) for further culturing the microorganism strains, which are propagated in the step 1-3, in a culture medium containing the compound defined as the chemical formula (27), and saccharides, but no nitrogen source.

The culture temperature may be a temperature at which the foregoing strains can well be propagated and may be 15° C. to 40° C., preferably 20° C. to 35° C., and further preferably 20° C. to 30° C.

Any culture manner such as a liquid phase culture manner, a solid phase culture manner or the like may be employed for the culture method as long as the manner is possible to propagate microorganism and produce the polyhydroxyalkanoate. Further, the types of the culture manners such as batch type culture, fed-batch type culture, semi-continuous culture, continuous culture manners or the like. Embodiments of the liquid phase batch type culture manner may be a method involving a step of supplying oxygen by shaking a shaking flask and an oxygen supply method employing a stirring ventilation way by a jar fermenter.

The inorganic culture medium to be employed for the foregoing culture method may be any as long as the culture medium contain components essential for propagation of the microorganism such as a phosphorus source (e.g., a phosphoric acid salt or the like), a nitrogen source (e.g., an ammonium salt, a nitric acid salt or the like) and, for example, an MSB culture medium, an M9 culture medium can be exemplified.

The composition of an inorganic salt culture medium (M9 culture medium) employed for one method of the present invention is as follows:
[M9 Culture Medium]

| | |
|---|---|
| $Na_2HPO_4$ | 6.2 g |
| $KH_2HPO_4$ | 3.0 g |
| NaCl | 0.5 g |
| $NH_4Cl$ | 1.0 g |

(in 1 liter of the culture medium, pH 7.0).

Further, for excellent propagation and polyhydroxyalkanoate production, it is required to add about 0.3% (v/v) of the following trace component solution to the inorganic salt culture medium:
[Trace Component Solution]
nitrilotriacetic acid: 1.5 g; $MgSO_4$: 3.0 g;
$MnSO_4$: 0.5 g; NaCl: 1.0 g; $FeSO_4$: 0.1 g;
$CaCl_2$: 0.1 g; $CoCl_2$: 0.1 g; $ZnSO_4$: 0.1 g;
$CuSO_4$: 0.1 g; $AlK(SO_4)_2$: 0.1 g;
$H_3BO_3$: 0.1 g; $Na_2MoO_4$: 0.1 g; and $NiCl_2$: 0.1 g
(in 1 liter of the trace component solution).
(Method of Producing 1-(Substituted Phenylsulfanyl)alkane as a Raw Material)

The polyhydroxyalkanoate according to the present invention can be obtained by culturing microorganism in a culture medium containing 1-(substituted phenylsulfanyl) alkane having the following chemical formula (28) to produce polyhydroxyalkanoate which is a precursor in the present invention, and treating the produced polyhydroxyalkanoate with sodium hypochlorite;

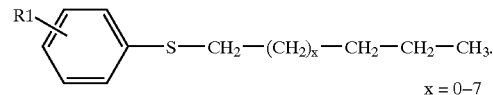

$$x = 0–7$$

wherein R1 denotes a substituent on an aromatic ring and is optionally selected from H, a halogen atom, CN, $NO_2$, $CH_3$, $C_2H_5$, $CH_3CH_2CH_2$, $(CH_3)_2CH$ and $(CH_3)_3C$; and x denotes at least one optional integer value within the range shown in the chemical formula.

The microorganism to be used in this case is not limited, provided that in the culture in a culture medium containing a compound having the chemical formula (28), the microorganism can produce polyhydroxyalkanoate as a precursor which is treated with sodium hypochlorite to obtain polyhydroxyalkanoate of the present invention. It is necessary for the microorganism used in the production of polyhydroxyalkanoate of the present invention to have the ability of converting alkane defined by the chemical formula (28) to the corresponding alkanoic acid, as well as the ability of producing, from the alkanoic acid, polyhydroxyalkanoate as a precursor which becomes the above-described polyhydroxyalkanoate of the present invention. In this case, the ability of converting alkane to alkanoic acid is usually expressed by having a group of enzyme system containing alkanemonooxygenase as an initial enzyme. As one example of microorganisms having such enzyme system, a microoganism belonging to *Psudomonas* species can be listed. More specifically, the above-described *Psudomonas cichorii* YN2 stain is listed.
(Culture Step)

For usual culture of microorganism to be utilized in this culture step, for example, production of preservation strains and propagation for ensuring the number of cells and active state necessary for producing the polyhydroxyalkanoate, a culture medium containing components required to propagate the microorganism to be employed is properly selected. For example, unless they cause no bad effects on growth and survival of microorganism, any types of general natural culture media (meat juice media, yeast extract media and the like) and artificial media containing nutrient sources can be employed. The culture conditions such as temperature, ventilation, agitation and the like may properly be selected depending on the microorganism to be employed.

In order to produce an aimed polyhydroxyalkanoate using such polyhydroxyalkanoate-producing microorganism as described above in the culture step, it is possible to add at least one selected from alkane compounds defined as the foregoing chemical formula (28) corresponding to the monomer unit may be use as a raw material for polyhydroxyalkanoate production to the culture medium and an use inorganic medium containing at least a carbon source for propagation of the microorganism. The alkane compound defined as the foregoing chemical formula (28) as the raw material is contained in the culture medium at an initial ratio preferably in a range from 0.01% to 1% (v/v), more preferably from 0.02% to 0.2% (v/v), based the culture medium.

Further, in the culture step, a step of culturing the microorganism in the presence of dicyclopropylketone, which is an alkane oxidation system inducer, may be included in the production step. Generally, the alkane oxidation system is known to efficiently carry out induction by a straight chain alkane such as octane, nonane and the like, which is a substrate in the metabolic pathway. However, in the case the foregoing exemplified straight chain alkane is used as the inducer, it has to be taken into consideration that the unit proportion of middle chain aliphatic polyhydroxyalkanoates in the produced polyhydroxyalkanoates increases. That is owing to straight chain alkanes are converted into straight chain alkanoic acids by the alkane oxidation system and become monomer substrate of PHA via β-oxidation system.

Also, the alkane compound having the chemical formula (28) to be employed as a raw material of the present invention is possible to induce the alkane oxidation system and is taken as a monomer unit in a polyhydroxyalkanoate similarly to the foregoing straight chain alkanes. The alkane oxidation system is originally evolved as the metabolic system of straight chain alkanes and the alkane compound having the chemical formula (28) of the present invention is insufficient to induce the alkane oxidation system in some cases.

Dicyclopropylketone is known (Journal of Bacteriology, 123, 546–556 (1975)))as so-called non-metabolism induction substance, which does not become a substrate but functions as an induction substance on the alkane oxidation system (which is not be oxidized by alkanemonoxidase). Hence, in the production method of the present invention, it is desirable that the induction of the alkane oxidation system is insufficient or the activity is further improved, and also it is desirable that the composition ratio of the middle chain aliphatic PHA unit in the aimed PHA is low, so that dicyclopropylketone can be used as a preferable induction substance of the alkane oxidation system. In this case, dicyclopropylketone efficiently induce the alkane oxidation system and the substrate metabolism is all applied to the conversion of the substituted alkane of the present invention. Consequently, the alkane compound-derived monomer unit having the chemical formula (28) is efficiently produced to improve the yield of the polyhydroxyalkanoate and increase the composition ratio of monomer units derived from the alkane compound having the chemical formula (28).

Dicyclopropyl ketone may be added to the culture medium together with the alkane compound having the chemical formula (28) and dicyclopropylketone may be added alone to the culture medium. In these cases, the content may properly be selected depending on the conditions such as the type of the substrate for propagation in the culture medium, the existence of the substituted-alkane, whether one-step culture or multi-step culture, which step of multi-step culture it is added to, and the like and generally, it is preferably in a range from 0.001% to 1% (v/v) in the culture medium and more preferably in a range from 0.01% to 0.1% (v/v).

Since the alkane compound having the chemical formula (28) is generally hydrophobic, water solubility is not necessarily high, however the foregoing microorganism is capable of utilizing the compound as a substrate and therefore, at the initial of the culture, even if the portion exceeding the solubility is in suspended state, the microorganism gradually takes it internally during the culture and it is successively dissolved in the culture medium without a problem. In some cases, for efficient intake, the microorganism itself excretes a substance like a surfactant to make intake of the substituted alkane which is a the substrate, easy.

The alkane compound defined as the foregoing chemical formula (28) which is a raw material may be contained in the culture medium, in some cases, in a state dissolved by a solvent such as 1-hexadecene and n-hexadecane or in a state of fine suspensions in order to enhance the dispersibility of the compound. In this case, the addition concentration of the solvent such as 1-hexadecene and n-hexadecane is required to be 3% or lower based on the culture medium.

A substrate for propagation which microogansim utilizes in propagation is separately add to a culture medium. As the substrate for propagation, nutrients such as yeast extract, polypeptone, meat extract and the like may be used. Further, it is possible to select based on the usability as carbon source, depending on the microorganism strains, from saccharides, organic acids produced as intermediates in TCA circuit, organic acids produced by one-step or two-step biochemical reaction from TCA circuit, their salts, amino acids, their salts, and straight chain alkanoic acids having 4 to 12 carbons and their salts.

Among various substrate for propagation, saccharides preferable to be used are one or more compounds selected from aldoses such as glyceraldehyde, erythrose, arabinose, xylose, glucose, galactose, mannose and fructose; alditols such as glycerol, erythritol and xylitol; aldonic acids such as gluconic acid; uronic acids such as glucuronic acid and galacturonic acid; and disaccharides such as maltose, sucrose and lactose.

The organic acids and their salts preferable to be used are one or more compounds selected from the group consisting of pyruvic acid, malic acid, lactic acid, citric acid, succinic acid and their salts. The amino acids and their salts preferable to be used are one or more compounds selected from glutamic acid, aspartic acid, and their salts.

Generally, among the substrates for propagation, polypeptones or saccharides are preferably used, and among the saccharides, at least one selected from the group consisting of glucose, fructose and mannose. These substrates for propagation are contained in the culture medium at a ratio generally from 0.1% to 5% (w/v), more preferably 0.2% to 2% (w/v).

Another method for producing the polyhydroxyalkanoate by the microorganism and accumulating it in the microorganism may be carried out by sufficiently propagating the microorganism once and then transferring the strains to a culture medium with a restricted nitrogen source of such as ammonium chloride and further carrying out propagation in the state that compounds to be substrates of the aimed units are added to improve the productivity in some cases. More particularly, a multistep system comprising a plurality of stages of the foregoing different steps can be exemplified.

More practically, the following two-step culture methods are preferable to be employed: a two-step culture method involving a step (step 1-A) of culturing microorganism in the culture medium containing an alkane compound defined as the chemical formula (28) and polypeptone as a carbon source continuously from the later stage of the logarithmic phase to the steady stage and after recovery of the microorganism cells by centrifugation or the like, a step (step 1-B) of further culturing the microorganism cells cultured and propagated in the prior step 1-A in a culture medium containing the alkane compound having the chemical formula (28) as well as an organic acid or its salts as the carbon source without nitrogen source; or a two-step culture method involving a step (step 1-C) of culturing microorganism in the culture medium containing an alkane compound defined as the chemical formula (28) and glucose as the carbon source continuously from the later stage of the logarithmic phase to the steady stage and after recovery of the microorganism cells by centrifugation or the like, a step (step 1-D) of further culturing the microorganism cells cultured and propagated in the prior step 1-C in a culture medium containing the alkane compound having the chemical formula (28) as well as glucose to be the carbon source without a nitrogen source; and also a two-step culture method involving a step (step 1-E) of culturing microorganism in the culture medium containing an alkane compound defined as the chemical formula (28) and polypeptone to be the carbon source continuously from the later stage of the logarithmic phase to the steady stage and after recovery of the microorganism cells by centrifugation or the like, a step (step 1-F) of further culturing the microorganism cells cultured and propagated in the prior step 1-E in a culture medium containing the alkane compound having the chemical formula (28) as well as saccharides to be the carbon source without a nitrogen source.

In such two-step culture methods, microorganism cells are previously propagated while producing, from the alkane compound having the chemical formula (28), the polyhydroxyalkanoate corresponding to this starting substance in the prior step and the already cultured microorganism cells are put in culture state where the microorganism cells produce mainly polyhydroxyalkanoate in the culture medium containing no nitrogen source in the posterior step, so that the amount of the polyhydroxyalkanoate to be accumulated in the microorganism cells can further be increased.

Further, it is possible to increase the yield amount of the polyhydroxyalkanoate and the proportions of the monomer units in the aimed polyhydroxyalkanoate by adding dicyclopropylketone, which is an effective induction substance in the alkane oxidation pathway having alkanemonoxidase as an initial enzyme, to at least one of the step 1-A and step 1-B, at least one of the step 1-C and step 1-D, and at least one of the step 1-E and step 1-F to efficiently carry out metabolism of the substituted alkane groups into corresponding substituted alkanoic acids.

Further, the culture methods can be made a one-step culture method of mainly aiming induction of the alkane oxidation system by using dicyclopropylketone alone instead of the substituted alkane groups in the step 1-A, step 1-C and step 1-E.

The culture temperature in such culture step may be a temperature at which the foregoing strains can well be propagated and may be 15 to 40° C., preferably 20° C. to 35° C., and more preferably 20° C. to 30° C.

Any culture manner such as a liquid phase culture manner, a solid phase culture manner or the like may be employed for the culture method as long as the manner is possible to propagate utilized microorganism and produce the polyhydroxyalkanoate containing a monomer unit corresponding to a starting substance from at least one selected from alkane compounds of the chemical formula (28) contained in the culture medium. Further, the types of the culture manners such as batch type culture, fed-batch type culture, semi-continuous culture, continuous culture manners or the like, if supply of a raw material, a carbon source and oxygen is suitably carried out. Embodiments of the liquid phase batch type culture manner may be a method involving a step of supplying oxygen by shaking a shaking flask and an oxygen supply method employing a stirring ventilation way by a jar fermenter.

The inorganic culture medium to be employed for the foregoing culture method may be any as long as the culture medium contain components essential for propagation of the microorganism such as a phosphorus source (e.g., a phosphoric acid salt or the like), a nitrogen source (e.g., an ammonium salt, a nitric acid salt or the like) and, for example, an MSB culture medium, an M9 culture medium can be exemplified.

(Sodium Hypochlorite Treatment Step)

The microorganism to be employed for the invention produces the polyhydroxyalkanoate having the phenylsulfanyl structure in the side chains by such a culture method. The polyhydroxyalkanoate of the invention can be produced by treating the polyhydroxyalkanoate produced in such a manner with sodium hypochlorite.

The simplest sodium hypochlorite treatment method is a method carried out by suspending and stirring the microorganism cells, which are cultured in the foregoing conditions and accumulate the polyhydroxyalkanoate, a precursor of the polyhydroxyalkanoate described in the invention, in an aqueous sodium hypochlorite solution as they are and recovering the insoluble components. In the case the concentration of the aqueous sodium hypochlorite solution is relatively high, or the reaction temperature is relatively high, PHA of the invention can be recovered in approximately pure state, however in some cases, the molecular weight is possible to be decreased. On the other hand, in the case the concentration of the aqueous sodium hypochlorite solution is low, components derived from cells of the microorganism may remain.

In such a case, the cultured microorganism cells are pulverized to recover the polyhydroxyalkanoate, as a precursor of the polyhydroxyalkanoate described in the invention, in a rough grade, and then the sodium hypochlorite treatment is carried out. By this method, the polyhydroxyalkanoate with a high purity can be recovered even in a relatively moderate condition.

Further another method is carried out by extracting and isolating only the polyhydroxyalkanoate from the polyhydroxyalkanoate-accumulating microorganism cells with a solvent such as chloroform and acetone in which the accumulated polyhydroxyalkanoate is soluble after the culture step, and then treating the obtained polyhydroxyalkanoate with sodium hypochlorite. In this method, the polyhydroxyalkanoate extracted and recovered from the microorganism cells is sometimes agglomerated in an aqueous solvent and in such a case, the method is often accompanied with operational difficulty such as significant decrease of the treatment efficiency. From that point, the former two methods are easy to be performed since the polyhydroxyalkanoate exists in form of fine particles in the microorganism cells and can be treated as it is or in suspended state.

As sodium hypochlorite used in the method of the present invention, anything can be used as long as it may contribute to the objects of the present invention, that is, oxidation of a sulfanyl (—S—) group and chlorination of a methylene group.

The sodium hypochlorite treatment conditions in the method of the present invention differ depending on the state of the polyhydroxyalkanoate to be treated (the existence of cell components; agglomerated or finely granular state; or the like), yet they are generally as follows.

The concentration of sodium hypochlorite, based on the effective chlorine concentration in the treatment solution, is set to be preferably 0.5% to 12.0%, desirably 1.5% to 5.0%. Also, it is preferable to carry out the treatment with a solution amount of about 50 mL to 300 mL per 1 g of dry weight of the cells. At that time, the treatment temperature is set to be preferably 0° C. to 20° C., desirably 0° C. to 10° C., since the molecular weight of the polyhydroxyalkanoate is possible to be decreased if the temperature is a room temperature (about 20° C.) or higher. Also, the reaction period is generally from about 1 hour to 5 hours and preferably about 2 hours.

In such treatment conditions, the polyhydroxyalkanoate accumulated in the microorganism cells by culturing the microorganism in the above-described conditions is converted into the polyhydroxyalkanoate consisting of, among the following units defined as the chemical formulas (1), (2), (3), (4), (5) and (6), units defined as the chemical formulas (1) and (2) and at least one of four types of units defined as the chemical formulas (3), (4), (5) and (6) in the molecule.

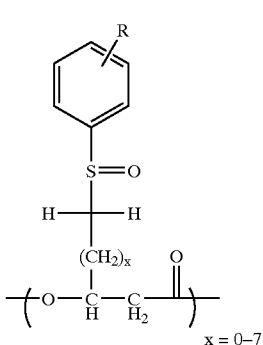

(1)

In the above formula, R denotes a substituent optionally selected from H, a halogen atom, CN, $NO_2$, COOR', $SO_2R''$, $CH_3$, $C_2H_5$, $CH_3CH_2CH_2$, $(CH_3)_2CH$ and $(CH_3)_3C$ (R' is H, Na, K, $CH_3$, or $C_2H_5$; and R" is OH, ONa, OK, a halogen atom, $OCH_3$, or $OC_2H_5$); and x denotes at least one optional integer value within the range shown in the chemical formula.

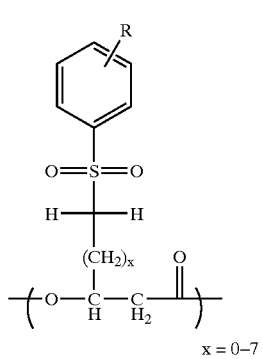

(2)

In the above formula, R denotes a substituent optionally selected from H, a halogen atom, CN, $NO_2$, COOR', $SO_2R''$, $CH_3$, $C_2H_5$, $CH_3CH_2CH_2$, $(CH_3)_2CH$ and $(CH_3)_3C$ (R' is H, Na, K, $CH_3$, or $C_2H_5$; and R" is OH, ONa, OK, a halogen atom, $OCH_3$, or $OC_2H_5$); and x denotes at least one optional integer value within the range shown in the chemical formula.

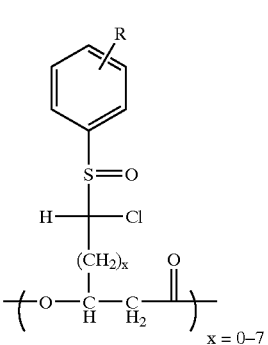

(3)

In the above formula, R denotes a substituent optionally selected from H, a halogen atom, CN, $NO_2$, COOR', $SO_2R''$, $CH_3$, $C_2H_5$, $CH_3CH_2CH_2$, $(CH_3)_2CH$ and $(CH_3)_3C$ (R' is H, Na, K, $CH_3$, or $C_2H_5$; and R" is OH, ONa, OK, a halogen atom, $OCH_3$, or $OC_2H_5$); and x denotes at least one optional integer value within the range shown in the chemical formula.

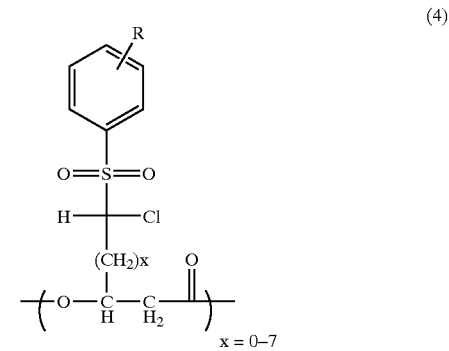

(4)

In the above formula, R denotes a substituent optionally selected from H, a halogen atom, CN, $NO_2$, COOR', $SO_2R''$, $CH_3$, $C_2H_5$, $CH_3CH_2CH_2$, $(CH_3)_2CH$ and $(CH_3)_3C$ (R' is H, Na, K, $CH_3$, or $C_2H_5$; and R" is OH, ONa, OK, a halogen atom, $OCH_3$, or $OC_2H_5$); and x denotes at least one optional integer value within the range shown in the chemical formula.

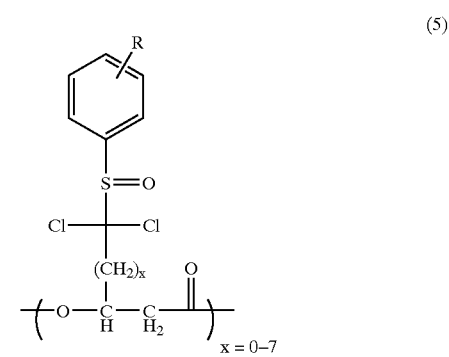

(5)

In the above formula, R denotes a substituent optionally selected from H, a halogen atom, CN, $NO_2$, COOR', $SO_2R''$, $CH_3$, $C_2H_5$, $CH_3CH_2CH_2$, $(CH_3)_2CH$ and $(CH_3)_3C$ (R' is H, Na, K, $CH_3$, or $C_2H_5$; and R" is OH, ONa, OK, a halogen atom, $OCH_3$, or $OC_2H_5$); and x denotes at least one optional integer value within the range shown in the chemical formula.

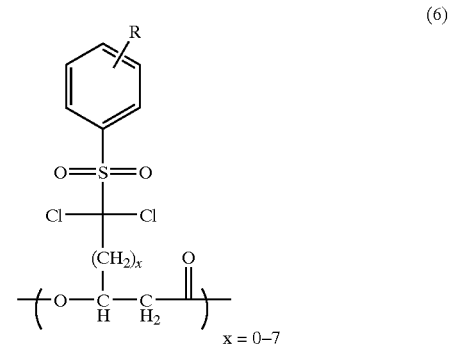

(6)

In the above formula, R denotes a substituent optionally selected from H, a halogen atom, CN, $NO_2$, COOR', $SO_2R''$, $CH_3$, $C_2H_5$, $CH_3CH_2CH_2$, $(CH_3)_2CH$ and $(CH_3)_3C$ (R' is H, Na, K, $CH_3$, or $C_2H_5$; and R" is OH, ONa, OK, a halogen atom, $OCH_3$, or $OC_2H_5$); and x denotes at least one optional integer value within the range shown in the chemical formula.

For the step of recovering the polyhydroxyalkanoate particle in the treatment solution after completion of the above-described step, any manner may be employed if the manner is capable of efficiently separating the polyhydroxyalkanoate particle from the coexisting soluble components to refine the polyhydroxyalkanoate particle. For example, a centrifugal separation method may be employed. Also, if it is probable that chlorine derived from sodium hypochlorite remains in the polyhydroxyalkanoate particle, a step of washing the polyhydroxyalkanoate particle recovered by the centrifugal separation with purified water may be added and further, a washing out step using a chemical agent capable of removing the remaining chlorine to the extent that the physical and chemical properties of the polyhydroxyalkanoate is not changed may be added.

The novel polyhydroxyalkanoate of the present invention comprises hydroxyalkanoic acid to be monomer units having the sulfinyl (—SO—) and sulfonyl (—$SO_2$—) structures and these structures in which hydrogen atom(s) of the methylene site at the α-position of the sulfur atom is/are substituted with chlorine atom(s). Owing to such specific structures, localization of electrons in the molecule takes place to make it possible to utilize the polyhydroxyalkanoate to material development in fields considerably different from those of conventional polyhydroxyalkanoate.

Further, PHA produced in the present invention is found having remarkably excellent properties for a charge control agent and considerably efficient in the case of being used for an electrostatic latent image developing toner containing the charge control agent and in the case of using the electrostatic latent image developing toner for an image forming apparatus comprising a specified development system and accordingly the present invention has been completed.

That is, the present invention provides a charge control agent containing polyhydroxyalkanoate comprising units defined as the following chemical formulas (1) and (2) formulas and at least one unit selected from four kind units having the following chemical formulas (3), (4), (5) and (6), in a molecule.

(1)

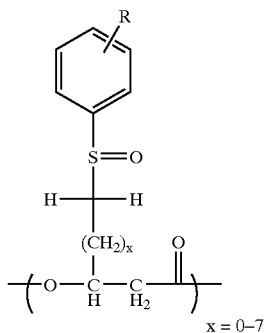

x = 0–7

In the above formula, R denotes a substituent optionally selected from H, a halogen atom, CN, $NO_2$, COOR', $SO_2R$", $CH_3$, $C_2H_5$, $CH_3CH_2CH_2$, $(CH_3)_2CH$ and $(CH_3)_3C$ (R' is H, Na, K, $CH_3$, or $C_2H_5$; and R" is OH, ONa, OK, a halogen atom, $OCH_3$, or $OC_2H_5$); and x denotes at least one optional integer value within the range shown in the chemical formula.

(2)

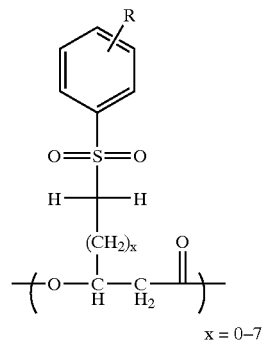

x = 0–7

In the above formula, R denotes a substituent optionally selected from H, a halogen atom, CN, $NO_2$, COOR', $SO_2R$", $CH_3$, $C_2H_5$, $CH_3CH_2CH_2$, $(CH_3)_2CH$ and $(CH_3)_3C$ (R' is H, Na, K, $CH_3$, or $C_2H_5$; and R" is OH, ONa, OK, a halogen atom, $OCH_3$, or $OC_2H_5$); and x denotes at least one optional integer value within the range shown in the chemical formula.

(3)

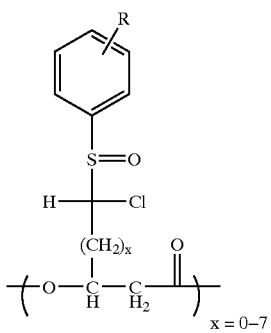

x = 0–7

In the above formula, R denotes a substituent optionally selected from H, a halogen atom, CN, $NO_2$, COOR', $SO_2R$", $CH_3$, $C_2H_5$, $CH_3CH_2CH_2$, $(CH_3)_2CH$ and $(CH_3)_3C$ (R' is H, Na, K, $CH_3$, or $C_2H_5$; and R" is OH, ONa, OK, a halogen atom, $OCH_3$, or $OC_2H_5$); and x denotes at least one optional integer value within the range shown in the chemical formula.

(4)

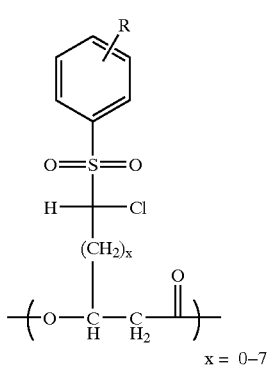

x = 0–7

In the above formula, R denotes a substituent optionally selected from H, a halogen atom, CN, $NO_2$, COOR', $SO_2R$", $CH_3$, $C_2H_5$, $CH_3CH_2CH_2$, $(CH_3)_2CH$ and $(CH_3)_3C$ (R' is H, Na, K, $CH_3$, or $C_2H_5$; and R" is OH, ONa, OK, a halogen atom, $OCH_3$, or $OC_2H_5$); and x denotes at least one optional integer value within the range shown in the chemical formula.

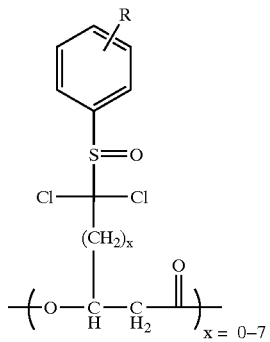

(5)

In the above formula, R denotes a substituent optionally selected from H, a halogen atom, CN, $NO_2$, COOR', $SO_2R''$ $CH_3$, $C_2H_5$, $CH_3CH_2CH_2$, $(CH_3)_2CH$ and $(CH_3)_3C$ (R' is H, Na, K, $CH_3$, or $C_2H_5$; R" is OH, ONa, OK, a halogen atom, $OCH_3$, or $OC_2H_5$); and x denotes at least one optional integer value within the range shown in the chemical formula.

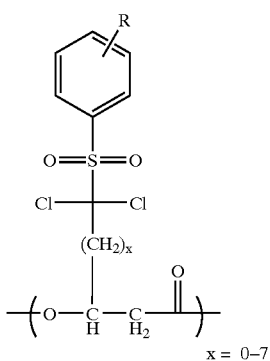

(6)

In the above formula, R denotes a substituent optionally selected from H, a halogen atom, CN, $NO_2$, COOR', $SO_2R''$, $CH_3$, $C_2H_5$, $CH_3CH_2CH_2$, $(CH_3)_2CH$ and $(CH_3)_3C$ (R' is H, Na, K, $CH_3$, or $C_2H_5$; and R" is OH, ONa, OK, a halogen atom, $OCH_3$, or $OC_2H_5$); and x denotes at least one optional integer value within the range shown in the chemical formula.

The charge control agent may be the PHA further consisting of at least one of units defined as the following chemical formulas (7) and (8) (the reference characters y and z separately denote at least one optional integer value within a range shown in the chemical formula, independently of the units defined as the chemical formulas (1), (2), (3), (4), (5), and (6)).

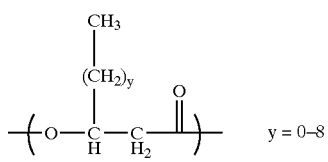

(7)

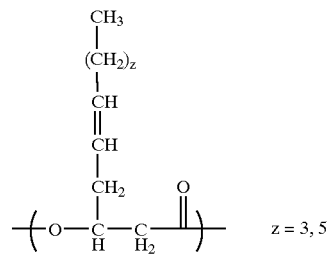

(8)

Further, the present invention provides an electrostatic latent image developing toner containing the charge control agent; an image forming method using the foregoing electrostatic latent image developing toner and comprising a step of uniformly charging an electrostatic latent image carrier by applying voltage to a charging member from the outside, a development step of forming a toner image on the electrostatic latent image carrier, a transfer step of transferring the toner image on the electrostatic latent image carrier to a material to be transferred with or without an intermediate transfer member, and a thermal fixation step of fixing the toner image on the material to be transferred by heating; and an image forming apparatus for forming an image to a recording material using the above-described electrostatic latent image developing toner.

The compounds disclosed in the present invention have basic skeletal structures as biodegradable resin and are expected to cause no adverse effects on the environment and the like. Similar to conventional plastics, the compounds disclosed in the invention can be used for production of a variety of products by melting and processing, and dissimilar to petroleum-derived synthetic polymers, the compounds have outstanding characteristic that they are biologically decomposable as well. Accordingly, when discarded, since the compounds of the invention are biologically decomposed and can be taken in the substance cycle of the nature, the compounds neither remain in natural environments nor cause pollution, unlike many conventionally used synthetic polymer compounds. Also, it has no need to use heavy metals such as chromium, cobalt, nickel, copper, zinc, iron and the like, the load to the environment is lessened as compared with a conventional charge control agent. Further, it is unnecessary to carry out combustion treatment owing to the biodegradation treatment, the compounds are effective materials also from an aspect of prevention of atmospheric air pollution and global warming phenomena and useful for plastics advantageous in environment preservation.

A compound suitable for the charge control agent to be used for the electrostatic latent image developing toner of the invention and disclosed in the invention will be described more particularly in the following.

The compound to be used for the invention is polyester resin of 3-hydroxyalkanoate monomer comprising units having an aromatic ring and a sulfinyl structure or a sulfonyl structure in the side chains and, as other units, units having an aromatic ring and a sulfinyl structure or a sulfonyl structure and also chlorine atom-substituted methylene group at the α-position of sulfur. The compound of the invention may further comprises either one or both of a straight chain 3-hydroxyalkanoate and a 3-hydroxyalkenoate having an unsaturated bond in the side chain, other than the foregoing units.

In the case of producing such a compound by a method comprising a step of producing it by microorganism, the compound of the invention becomes isotactic polymer containing only R-isomer, yet it is not particularly needed to be isotactic polymer if the purpose of the invention is achieved in both physical and functional aspects and the compound may also be an atactic polymer. Further, the compound of the invention can be obtained by a chemical synthesis method employing such as a ring-opening polymerization of a lactone compound.

The methods of the invention are as described above in the case the compound of the invention is produced by the method comprising a step of producing it by microorganism.

The important point of the invention is that the polyhydroxyalkanoate contained in the charge control agent of the invention consists of units having an aromatic ring with a sulfinyl structure or a sulfonyl structure in the side chains and, as other units, units having an aromatic ring with a sulfinyl structure or a sulfonyl structure and also chlorine atom substituting in the methylene group at the α-position. Owing to these structures, localization of electrons takes place in the molecule and accordingly the charge control agent of the invention is provided with excellent negative charge property.

Further, by changing the ratio of the units having these structures, rising of the electric charge can be controlled. Also, by controlling the ratio of the units, the dependency-on-environment can be lessened.

In restriction of production, the polyhydroxyalkanoate contained in the charge control agent of the invention inevitably contains units having an aromatic ring in the side chain and also the sulfinyl structure or the sulfonyl structure, that is, units defined as the foregoing chemical formulas (1), (2) in many cases, yet that is not necessarily essential from an aspect of contribution to charging capability of the charge control agent of the invention and it is supposed that the existence of at least one of the units having an aromatic ring in the side chain and also the sulfinyl structure or the sulfonyl structure and further chlorine atom substituting in the methylene group at the α-position, that is, defined as the foregoing chemical formulas (3), (4), (5), and (6) greatly affects the charging capability of the charge control agent of the invention.

The units having these structures may be contained in 1% by mol in the polymer and their ratio may be selected in consideration of the ratio relative to others and the aimed charging property and in order to obtain a sufficient charging property, it is preferable to contain the units in at least 5% by mol. The upper limit of the units to be contained may be determined in consideration of the type of the binder resin to be selected and the relation with other units and not particularly restricted if it is in a range in which the compatibility with the binder resin is not deteriorated.

The compounds disclosed in the invention have good compatibility with the binder resin and significantly excellent compatibility particularly with polyester type binder resin. Since a toner containing the compounds of the invention has a high specific charging quantity and excellent stability with the lapse of time, the toner can stably provide a clear image in image formation by electrostatic recording even if the toner is stored for a long duration and also, since the compounds are colorless and have a negative charge property, they can be used for production of a black negative charge toner and a color toner as well.

Further, by properly selecting the types and composition ratios of the monomer units composing the compounds of the invention, wide range compatibility control is made possible. If a resin composition in which the charge control agent is put in micro-phase separation state in a toner binder, no electric continuity is formed in the toner so that electric charge can stably be maintained. Further, since the compounds of the invention contain no heavy metals, the compounds are excellently safe in the environments. Further, in the case of producing a toner by suspension polymerization or emulsion polymerization, no polymerization inhibition by heavy metals, which is observed in the case of using a metal-containing charge control agent, takes place so that a toner can stably be produced.

(Addition of PHA to Toner)

In the invention, the method for adding the foregoing compounds to a toner may be a method of internal addition to the toner and a method of external addition to the toner. The addition amount of the internal addition is generally 0.1 to 50% by weight, preferably 0.3 to 30% by weight, and further preferably 0.5 to 20% by weight as the weight ratio of the toner binder and the charge control agent. If it is lower than 0.1% by weight, the improvement degree of the charging property of the toner is insignificant and thus not preferable. Whereas, if it is higher than 50% by weight, it is not preferably from an economical point of view. Further, in the case of the external addition, the weight ratio of the toner binder and the charge control agent is preferably 0.01 to 5% by weight and especially, the compounds are stuck to the surface of the toner by a mechanochemical manner. Further, the above-described compound of the invention may be used in combination of a known charge control agent.

The number average molecular weight of the above-described compounds of the invention is generally 1,000 to 500,000 and preferably 1,000 to 100,000. If it is less than 1,000, the compounds have complete compatibility with the toner binder to make discontinuous domain formation difficult and result in an insufficient quantity of the electric charge and also an undesirable effect on the fluidity of the toner. Further, if it is higher than 500,000, dispersion in the toner becomes difficult.

The molecular weights of the compounds of the invention are measured by GPC (gel permeation chromatography). A practical GPC measurement method is carried out by previously dissolving a compound of the first embodiment of the invention in dimethylformamide (DMF) containing 0.1% by weight of LiBr, measuring the sample with a similar mobile phase, and calculating the molecular weight distribution from calibration curves of standardized polystyrenes.

Further, in the invention, compounds having the ratio (Mw/Mn) of the weight average molecular weight (Mw) and the number average molecular weight (Mn) measured by the above-described manner in a range from 1 to 10 are preferable to be used.

In the invention, the above-described compounds of the invention have a melting point in a range preferably from 20 to 150° C., especially preferably from 40 to 150° C. or have no melting point but a glass transition temperature in a range preferably from 20 to 150° C., especially preferably from 40 to 150° C. If the foregoing melting point is lower than 20° C. or the glass transition temperature with no melting point is lower than 20° C., the fluidity and the storage property of the toner are often adversely affected. Whereas if the foregoing melting point is higher than 150° C. or the glass transition temperature with no melting point is higher than 150° C., the charge control agent becomes difficult to be kneaded with the toner and the charge quantity distribution becomes broad in many cases.

To measure the melting point Tm and the glass transition temperature Tg in this case, a high precision and internally heating input compensation type differential scanning calorimeter, for example, DSC-7 manufactured by Perkin Elmer Inc. may be employed.

Regarding the toner binder and the electrostatic latent image developing toner of the invention, the weight ratio of the toner binder and the charge control agent is generally 0.1 to 50% by weight, preferably 0.3 to 30% by weight, and more preferably 0.5 to 20% by weight. Regarding the composition ratio of the electrostatic latent image developing toner of the invention, generally the foregoing charge control agent is in a range from 0.1 to 50% by weight, the toner binder is in a range from 20 to 95% by weight, and a coloring material is in a range from 0 to 15% by weight on the bases of the weight of the toner and based on the necessity, a magnetic powder (a powder of a ferromagnetic metal such as iron, cobalt, nickel and the like and a compound such as magnetite, hematite, ferrite and the like) functioning as a coloring material may be added in an amount not more than 60% by weight. Further, various additives [a lubricant (polytetrafluoroethylene, a lower molecular weight polyolefin, an aliphatic acid or its metal salt or amide, and the like) and other charge control agents (a nigrosine derivative, a naphthenoic acid metal salt, an alkoxylated amine, a quaternary ammonium salt, and the like)] may be added. Further, in order to improve the fluidity of the toner, a hydrophobic colloidal silica fine powder may also be employed. The amounts of these additives are generally not more than 10% by weight on the bases of the toner weight.

In the toner of the invention, it is preferable for at least some of the toner binder to form a continuous phase and at least some of the charge control agent to form discontinuous domain. As compared with the case where the charge control agent has complete compatibility with the toner binder without forming the discontinuous domain, the added charge control agent is easily exposed to the surface and effective even in a small amount. The dispersion particle diameter of the domain is preferably 0.01 to 4 μm and more preferably 0.05 to 2 μm. If it is bigger than 4 μm, the dispersibility becomes insufficient and the charge quantity distribution becomes broad and the transparency of the toner is deteriorated. Whereas, if the dispersion particle diameter is smaller than 0.01 μm, it becomes similar to the case where the charge control agent has complete compatibility with the binder without forming discontinuous domain, a large amount of the charge control agent is required to be added. That at least some of the foregoing charge control agent forms the discontinuous domain and the dispersion particle size can be observed by observing a specimen of the toner with a transmission electron microscope. In order clearly observe the interface, it is also effective to carry out observation of a toner specimen by electron microscope after the specimen is dyed with ruthenium tetraoxide, osmium tetraoxide and the like.

Further, for the purpose of making the particle diameter of the discontinuous domain, which the foregoing compounds of the invention form, small, a polymer compatible with the foregoing compounds of the invention and also with the toner binder may be added as a compatible agent. The compatible agent may be polymers comprising mutually graft- or block-polymerized polymer chains containing at least 50% by mol of monomers having practically similar structure to that of the constituent monomers of the compounds of the invention and polymer chains containing at least 50% by mol of monomers having practically similar structure to that of the toner. The amount of the compatible agent to be used is generally not more than 30% by weight and preferably 1 to 10% by weight, on the bases of the compounds of the invention.

<Other Constituent Materials>

Hereinafter, other constituent materials constituting the electrostatic latent image developing toner of the invention will be described.

(Binder Resin)

At first, any resin may be used as the binder resin without any particular restrictions if it is generally used for production of a toner. Also, the charge control agent of the invention may previously be mixed with the binder resin to be used as a tone binder composition of the invention having charge controlling capability before production of the toner. For example, as the binder resin, styrene-based polymers, polyester-based polymers, epoxy-based polymers, polyolefin-based polymers, and polyurethane-based polymers, and the like can be exemplified and they are used alone or while being mixed with one another.

The styrene-based polymers may be styrene-(meth) acrylic acid ester copolymers and copolymers of these copolymers with other monomers copolymerizable with them; copolymers of styrene with diene type monomers (butadiene, isoprene and the like) and copolymers of these copolymers with other monomers copolymerizable with them; and the like. The polyester-based polymers may be condensation polymerization products of aromatic dicarboxylic acid and aromatic diol alkylene oxide addition products and the like. The epoxy-based polymers may be reaction products of aromatic diols and epichlorohydrin and their modified products. The polyolefin-based polymers may be polyethylene, polypropylene, and copolymer chains of these polymers with monomers polymerizable with them. The polyurethane-based polymers may be addition polymerization products of aromatic diisocyanates and aromatic diol alkylene oxide addition products and the like.

Practical examples of the binder resin to be employed in the invention are polymers of the following polymerizable monomers or their mixtures or copolymerization products produced from two or more kinds of the following polymerizable monomers. Such polymers are more particularly, for example, styrene-based polymers such as styrene-acrylic acid copolymer, styrene-methacrylic acid copolymer, and the like; polyester-based polymers; epoxy-based polymers; polyolefin-based polymers; and polyurethane-based polymers and they are preferably used.

Practical examples of the polymerizable monomers are styrene and its derivatives such as styrene, o-methylstyrene, m-methylstyrene, p-methylstyrene, p-methoxystyrene, p-phenylstyrene, p-chlorostyrene, 3,4-dichlorostyrene, p-ethylstyrene, 2,4-dimethylstyrene, p-n-butylstyrene, p-tert-butylstyrene, p-n-hexylstyrene, p-n-octylstyrene, p-n-nonylstyrene, p-n-decylstyrene, p-n-dodecylstyrene, and the like; ethylenic unsaturated monoolefins such as ethylene, propylene, butylene, isobutylene and the like; polyenes such as butadiene and the like; vinyl halides such as vinyl chloride, vinylidene chloride, vinyl bromide, vinyl fluoride and the like; vinyl esters such as vinyl acetate, vinyl propionate, vinyl benzoate and the like; α-methylene aliphatic monocarboxylic acid esters such as methyl methacrylate, ethyl methacrylate, propyl methacrylate, n-butyl methacrylate, isobutyl methacrylate, n-octyl methacrylate, dodecyl methacrylate, 2-ethylhexyl methacrylate, stearyl methacrylate, phenyl methacrylate, dimethylaminoethyl methacrylate, diethylaminoethyl methacrylate, and the like; acrylic acid esters such as methyl acrylate, ethyl acrylate, n-butyl acrylate, isobutyl acrylate, propyl acrylate, n-octyl acrylate, dodecyl acrylate, 2-ethylhexyl acrylate, stearyl acrylate, 2-chloroethyl acrylate, phenyl acrylate, and the like; vinyl ethers such as vinyl methyl ether, vinyl ethyl ether, vinyl isobutyl ether, and the like; vinyl ketones such as vinyl methyl ketone, vinyl hexyl ketone, vinyl isopropenyl ketone, and the like; N-vinyl compounds such as N-vinylpyrrole, N-vinylcarbazole, N-vinylindole, N-vinylpyrrolidone and the like; vinyl naphthalenes; acrylic acid or methacrylic acid derivatives such as acrylonitrile, methacrylonitrile, acrylamide and the like; the above-described α, β-unsaturated acid esters; bibasic acid diesters; dicarboxylic acids such as maleic acid, methyl maleate, butyl maleate, dimethyl maleate, phthalic acid, succinic acid, terephthalic acid, and the like; polyols such as ethylene glycol, diethylene glycol, triethylene glycol, 1,2-propylene glycol, 1,3-propylene glycol, 1,4-butanediol, 1,6-hexanediol, bisphenol A, hydrogenated bisphenol A, polyoxyethylene-modified bisphenol A and the like; isocyanates such as p-phenylene diisocyanate, p-xylene diisocyanate, p-xylylene diisocyanate, 1,4-tetramethylene diisocyanate, and the like; amines such as ethylamine, butylamine, ethylenediamine, 1,4-diaminobenzene, 1,4-diaminobutane, monoethanolamine, and the like; epoxy compounds such as diglycidyl ether, ethylene glycol diglycidyl ether, bisphenol A glycidyl ether, hydroquinone glycidyl ether, and the like.

(Cross-linking Agent)

In the case of producing the binder resin to be employed in the invention, based on the necessity, the following cross-linking agent may be used. Examples of a bifunctional cross-linking agent are divinylbenzene, bis(4-acryloxypolyethoxyphenyl)propane, ethylene glycol diacrylate, 1,3-butylene glycol diacrylate, 1,4-butanediol diacrylate, 1,5-pentanediol diacrylate, 1,6-hexanediol diacrylate, neopentyl glycol diacrylate, diethylene glycol diacrylate, triethylene glycol diacrylate, tetraethylene glycol diacrylate, respective diacrylates of polyethylene glycol #200, #400, #600, dipropylene glycol diacrylate, polypropylene glycol diacrylate, polyester type diacrylate, and those obtained by replacing these exemplified acrylates with methacrylates.

Examples of bi- or higher polyfunctional cross-linking agent are pentaerythritol triacrylate, trimethylolethane triacrylate, trimethylolpropane triacrylate, tetramethylolmethane tetraacrylate, oligoester acrylate, those obtained by replacing these acrylates with methacrylates, 2,2-bis(4-methacryloxypolyethoxyphenyl)propane, diallyl phthalate, triallyl cyanurate, triallyl azocyanurate, triallyl isocyanurate, triallyl trimellitate, diaryl chlorendate, and the like.

(Polymerization Initiator)

In the case of producing the binder resin to be employed for the invention, the following polymerization initiators may be used based on the necessity: for example, tert-butyl peroxy-2-ethylhexanoate, cumine perpivalate, tert-butyl peroxylaurate, benzoyl peroxide, lauroyl peroxide, octanoyl peroxide, di-tert-butyl peroxide, tert-butylcumyl peroxide, dicumyl peroxide, 2,2'-azobis isobutyronitrile, 2,2'-azobis(2-methylbutyronitrile), 2,2'-azobis(2,4-dimethylvaleronitrile), 2,2'-azobis(4-methoxy-2,4-dimethylvaleronitrile), 1,1-bis(tert-butylperoxy)-3,3,5-trimethylcyclohexane, 1,1-bis(tert-butylperoxy)cyclohexane, 1,4-bis(tert-butylperoxycarbonyl)cyclohexane, 2,2-bis(tert-butylperoxy)octane, n-butyl 4,4-bis(tert-butylperoxy)valirate, 2,2-bis(tert-butylperoxy)butane, 1,3-bis(tert-butylperoxyisopropyl)benzene, 2,5-dimethyl-2,5-bis(tert-butylperoxy)hexane, 2,5-dimethyl-2,5-bis(benzoylperoxy)hexane, di-tert-butyldiperoxy isophthalate, 2,2-bis(4,4-di-tert-butylperoxycyclohexyl) propane, di-tert-butyl peroxy-α-methylsuccinate, di-tert-butyl peroxydimethylglutarate, di-tert-butyl peroxyhexahydroterephthalate, di-tert-butyl peroxyazelate, 2,5-dimethyl-2,5-(di-tert-butylperoxy)hexane, diethylene glycol bis(tert-butylperoxycarbonate), di-tert-butyl peroxytrimethyladipate, tris(tert-butylperoxy)triazine, vinyltris(tert-butylperoxy)silane and the like. Each of these compounds may be used alone or in combination with others. The use amount of them is generally in 0.05 parts by weight or more (preferably 0.1 to 15 parts by weight) to 100 parts by weight of monomers.

(Other Biodegradable Plastics)

Further, in the invention, biodegradable plastics are also preferable to be used. Examples of the biodegradable plastics are "Ecostar", "Ecostar Plus" (produced by Hagiwara Kogyo Co., Ltd.), "Biopol" (produced by ICI Japan, Co., Ltd.), "Ajicoat" (Ajinomoto Co., Inc.), "PLACCEL", "Polycaprolactone" (produced by Daicel Chem., Ind., Ltd.), "Sholex", "Bionolle" (produced by Showa Denko K.K.), "LACTY" (produced by Shimazu Corporation), "LACEA" (produced by Mitsui Chemicals, Inc.), "IUPEC" (produced by Mitsubishi Gas Chem. Co., Ltd.) and the like.

It is preferable for the combinations of the binder resin and the charge control agent of the invention that the structure of the polymers of the binder resin and the polymer structure of the polymer chain of the charge control agent are similar to each other as much as possible. If the structure of the polymers of the binder resin and the polymer structure of the polymer chain of the charge control agent are considerably dissimilar to each other, the charge control agent tends to be dispersed insufficiently in the binder resin.

The weight ratio of the charge control agent of the invention to be internally added to the binder resin is generally 0.1 to 50% by weight, preferably 0.3 to 30% by weight, and more preferably 0.5 to 20% by weight. If the weight ratio of the charge control agent to be internally added is lower than 0.1% by weight, the charging quantity becomes low and if the weight ratio is higher than 50% by weight, the charging stability of the toner is deteriorated.

(Coloring Agent)

Any coloring agent generally used for production of a toner may be used as the coloring agent composing the electrostatic latent image developing toner of the invention without particular restrictions. For example, carbon black, titanium white, and any other pigment and/or dye may be used. For example, in the case the electrostatic latent image developing toner of the invention is used for a magnetic color toner, examples of the coloring agent to be employed are C.I. Direct Red 1, C.I. Direct Red 4, C.I. Acid Red 1, C.I. Basic Red 1, C.I. Mordant Red 30, C.I. Direct Blue 1, C.I. Direct Blue 2, C.I. Acid Blue 9, C.I. Acid Blue 15, C.I. Basic Blue 3, C.I. Basic Blue 5, C.I. Mordant Blue 7, C.I. Direct Green 6, C.I. Basic Green 4, C.I. Basic Green 6 and the like. Examples of the pigment are Chrome Yellow, Cadmium Yellow, Mineral Fast Yellow, Naval Yellow, Naphthol Yellow S, Hansa Yellow G, Permanent Yellow NCG, Tartrazine Yellow Lake, Chrome Orange, Molybenum Orange, Permanent Orange GTR, Pyrazolone Orange, Benzidine Orange G, Cadmium Red, Permanent Red 4R, Watching Red calcium salt, Eosine Lake, Brilliant Carmine 3B, Manganese Violet, Fast Violet B, Methyl Violet Lake, Prussian Blue, Cobalt Blue, Alkali Blue Lake, Victoria Blue Lake, Phthalocyanine Blue, Fast Sky Blue, Indanthrene Blue BC, Chrome Green, chromium oxide, Pigment Green B, Malachite Green Lake, Final Yellow Green G and the like.

In the case the electrostatic latent image developing toner of the invention is used for a two-component type full color toner, the following coloring agents can be used. For example, coloring pigments for magenta toners are C.I.

Pigment Red 1, 2, 3, 4, 5, 6, 7, 8, 9, 10, 11, 12, 13, 14, 15, 16, 17, 18, 19, 21, 22, 23, 30, 31, 32, 37, 38, 39, 40, 41, 48, 49, 50, 51, 52, 53, 54, 55, 57, 58, 60, 63, 64, 68, 81, 83, 87, 88, 89, 90, 112, 114, 122, 123, 163, 202, 206, 207, 209, C.I. Pigment Violet 19, C.I. Vat Red 1, 2, 10, 13, 15, 23, 29, 35 and the like.

In the invention, the above-exemplified pigments may be used alone, yet use of the pigments in combination with dyes is more preferable to improve the clearness from the aspect of the full color image quality. In such a case, the examples of usable magenta dyes are oil-soluble dyes such as C.I. Solvent Red 1, 3, 8, 23, 24, 25, 27, 30, 49, 81, 82, 83, 84, 100, 109, 121, C.I. Disperse Red 9, C.I. Solvent Violet 8, 13, 14, 21, 27, C.I. Solvent Red 1, 3, 8, 23, 24, 25, 27, 30, 49, 81, and C.I. Disperse Violet 1 and the like; and basic dyes such as C.I. Basic Red 1, 2, 9, 12, 13, 14, 15, 17, 18, 22, 23, 24, 27, 29, 32, 34, 35, 36, 37, 38, 39, 40, C.I. Basic Violet 1, 3, 7, 10, 14, 15, 21, 25, 26, 27, 28 and the like.

As other coloring pigments, examples of cyan coloring pigments are C.I. Pigment Blue 2, 3, 15, 16, 17, C.I. Vat Blue 6, C.I. Acid Blue 45, copper-phthalocyanine pigments having a phthalocyanine skeleton containing substituents of phthalimidomethyl groups in number of 1 to 5, and the like.

Examples of yellow coloring pigments are C.I. Pigment Yellow 1, 2, 3, 4, 5, 6, 7, 10, 11, 12, 13, 14, 15, 16, 17, 23, 65, 73, 83, C.I. Vat Yellow 1, 3, 20 and the like.

The above-described dyes and pigments may be used solely or may be used while being optionally mixed with one another to obtain desired hue of the toner. Incidentally, taking the environmental preservation and the safety to human being into consideration, a variety of edible coloring elements may preferably be used. The content of the coloring agents in the toner may widely altered depending on the desired coloration effects. Generally, in order to obtain the best toner properties, that is, in consideration of the printing coloration capability, the toner shape stability, and the toner leap, these coloring agents are used at a ratio in a range from 0.1 to 60 parts by weight, preferably 0.5 to 20 parts by weight, to 100 parts by weight of the binder resin.

(Other Components of Toner)

In the electrostatic latent image developing toner of the invention may contain the following compounds other than the foregoing binder resin and the coloring agent components, to an extent (within a ratio less than the content of the binder resin) in which no undesired effect is caused in the invention. The examples of the compounds are silicone resin; polyester; polyurethane; polyamide; epoxy resin; poly (vinyl butyral); rosin; modified rosin; terpene resin; phenolic resin; aliphatic or alicyclic hydrocarbon resin such as lower molecular weight polyethylene and lower molecular weight polypropylene; aromatic type petroleum resin; and chlorinated paraffin and paraffin waxes. Among them, preferable waxes to be used are practically lower molecular weight polypropylene and its byproducts, lower molecular weight polyester, and ester type wax and aliphatic derivatives. Among these waxes, waxes separated based on the molecular weight of the waxes by various methods are also preferable to be used for the invention. Further, after separation, the waxes may be modified to control the acid values, block-copolymerized, or graft-modified.

Specially, in the electrostatic latent image developing toner of the invention, in the case such wax components as described above are added and these wax components are found practically dispersed in the binder resin in spherical and/or elliptical island state by cross-sectional observation of the toner by a transmission electron microscope, the toner is provided with excellent properties.

(Production Method of Toner)

Any conventionally known method may be employed for a practical method for producing an electrostatic latent image developing toner of the invention having the constitution as described above. The electrostatic latent image developing toner of the invention can be produced, for example, by a so-called pulverization method for obtaining a toner through the following steps. That is, practically, the compounds of the invention described above, resin materials such as binder resin, other components and waxes to be added based on the necessity are sufficiently mixed by a mixer such as a Henshel mixer, a ball mill and the like and then melted and kneaded using a thermally kneading apparatus such as heating rolls, a kneader, an extruder and the like to make the resin material compatible with one another, and as coloring agents, pigments, dyes, or magnetic materials and also additives such as metal compounds to be added based on the necessity are dispersed or dissolved in the resulting mixture, and after solidification of the mixture by cooling, the obtained solidified product is pulverized by a pulverizing apparatus such as a jet mill, a ball mill and the like and then classified to obtain an electrostatic latent image developing toner of the invention with a desired particle size. In the above-described classification step, from an aspect of productivity, a multi-step classification apparatus is preferable to be employed.

Further, the electrostatic latent image developing toner of the invention can be obtained by mixing and stirring the binder resin and the compounds of the invention in a solvent (e.g., aromatic hydrocarbons such as toluene, xylene and the like; halogen compounds such as chloroform, ethylene dichloride, and the like; ketones such as acetone, methyl ethyl ketone, and the like; amides such as dimethylformamide and the like), and then adding the resulting mixture to water to re-precipitate the mixture, filtering and drying the precipitated solid matter, and pulverizing the solid matter by a pulverizing apparatus such as a jet mill, a ball mill, and the like, and then classifying the pulverized matter to obtain the electrostatic latent image developing toner of the invention with a desired particle size.

Further, the electrostatic latent image developing toner of the invention can be produced by a so-called polymerization method as follows. That is, in this case, the compounds of the invention, a polymerizable monomer, and as coloring agents, pigments, dyes, or magnetic materials and also based on the necessity, additives such as a cross-linking agent, a polymerization initiator, waxes, and others are mixed and dispersed and in the presence of a surfactant or the like, the mixture is subjected to suspension polymerization to obtain a polymerizable and coloring resin particle, and after the obtained particle is separated by solid-liquid separation, the particle is dried and classified if necessary to obtain an electrostatic latent image developing toner of the invention with a desired particle size.

Furthermore, a coloring fine particle containing no charge control agent is produced by the above-described manner and then either solely or together with an extra-addition agent such as colloidal silica, the compounds of the invention may be stuck and added to the surface of the particle by a mechanochemical method or the like.

(Silica Extra-addition Agent)

In the invention, it is preferable to externally add a silica fine powder to the toner produced in such a manner as described above in order to improve the charging stability, the development capability, the fluidity, and the durability. The silica fine powder to be employed in this case can provide desirable effects if it has a specific surface area in a range of 20 m²/g or higher (especially 30 to 400 m²/g) measured based on the nitrogen adsorption by BET method. The content of the silica fine powder to be added is preferably 0.01 to 8 parts by weight, more preferably 0.1 to 5 parts by weight, to 100 parts by weight of the toner particle. In this case, based on the necessity, the silica fine powder to be used in the case is preferably treated for the purpose of controlling the hydrophobicity and charging property with silicone varnish, variously modified silicone varnish, silicone oil, variously modified silicone oil, a silane coupling agent, a silane coupling agent having a functional group, and other organosilicon compounds. These treatment agent may be used by mixing.

(Inorganic Powder)

Further, in order to improve the development capability and the durability, the following inorganic powder is preferable to be added. Examples of the powder are oxides of metals such as magnesium, zinc, aluminum, cerium, cobalt, iron, zirconium, chromium, manganese, strontium tin, antimony and the like; compounded metal oxides such as calcium titanate, magnesium titanate, and strontium titanate; metal salts such as calcium carbonate, magnesium carbonate, and aluminum carbonates; clay minerals such as kaolin; phosphate compounds such as apatite; silicon compounds such as silicon carbide, and silicon nitride; and carbon powder such as carbon black and graphite. Among them, fine powders of zinc oxide, aluminum oxide, cobalt oxide, manganese oxide, strontium titanate, and magnesium titanate are preferable to be used.

(Lubricant)

Further, the following lubricant powder may be added to the toner. For example, fluoro resin such as Teflon, poly (vinylidene fluoride) and the like; fluoride compounds such as carbon fluoride; aliphatic acid metal salts such as zinc stearate; aliphatic acid derivatives such as aliphatic acid, aliphatic acid esters and the like; and molybdenum sulfide.

(Carrier)

The electrostatic latent image developing toner of the invention having the above-described constitution is usable for a variety of conventionally known toners; solely as a non-magnetic mono-component developer, as a non-magnetic toner together with a magnetic carrier for composing a magnetic two-component developer, as a magnetic toner to be used solely for a magnetic mono-component toner. In this case, as the carrier to be used in the case of the two-component development, any conventionally known carrier may be used. More particularly, particles of surface-oxidized or non-oxidized metals such as iron, nickel, cobalt, chromium and rare earth metals, their alloys and oxides and having an average particle size of 20 to 300 μm may be used as the carrier particle. Further, the carrier to be used in the invention are preferably the above-described carrier particle whose surface bears or is coated with a substance such as styrene-based resin, acrylic resin, silicone resin, fluoro resin, polyester resin and the like.

(Magnetic Toner)

The electrostatic latent image developing toner of the invention may be a magnetic toner by adding a magnetic material to the toner particle. In this case, the magnetic material may take a role also as a coloring agent. The magnetic material to be used in this case may be iron oxides such as magnetite, hematite, and ferrite; metals such as iron, cobalt, and nickel; alloys of these metals with metals such as aluminum, cobalt, copper lead, magnesium, tin, zinc, antimony, beryllium, bismuth, cadmium, calcium, manganese, selenium, titanium, tungsten, and vanadium; and their mixtures. The magnetic material to be used in the invention has an average particle size preferably 2 μm or smaller, more preferably 0.1 to 0.5 μm. The amount to be added to the toner is preferably 20 to 200 parts by weight to 100 parts by weight of the binder resin and especially preferably 40 to 150 parts by weight to 100 parts by weight of the binder resin.

Further, in order to give high image quality, it is required to precisely develop extremely small latent image dots and for that, it is preferable to control, for example, the weight average particle size of the electrostatic latent image developing toner of the invention to be in a range from 4 μm to 9 μm. That is, if the toner particle has a weight average particle size smaller than 4 μm, the transfer efficiency is decreased and a large amount of the transfer residual toner tends to remain on a photosensitive member to result in an undesirable cause of uneven and irregular image formation attributed to fogging and transfer failures. Whereas, if the toner particle has a weight average particle size larger than 9 μm, letters and line images tend to be eliminated.

In the invention, the average particle size and the particle size distribution of the toner are measured by using Coulter Counter TA-II model or Coulter Multisizer (manufactured by Beckman Coulter, Inc.) or the like to which an interface (manufactured by Nikkaki-bios Co.) for outputting the distribution by number, the distribution by volume and a PC9801 personal computer (manufactured by NEC) are connected. As an electrolytic solution to be used at that time, an aqueous 1% NaCl solution is prepared using first-grade sodium chloride. As the electrolytic solution, for example, a commercialized ISOTON R-II (produced by Coulter Scientific Japan Co.) may also be usable. A practical measurement method involves steps of adding 0.1 to 5 ml of a surfactant (preferably an alkylbenzenesulfonic acid salt is used) as a dispersant to 100 to 150 ml of the above-described aqueous solution, further adding 2 to 20 mg of a sample to the resulting solution to obtain a specimen to be measured. At the time of measurement, the electrolytic solution in which the specimen to be measured is suspended is treated for dispersion for 1 to 3 minutes by an ultrasonic dispersing apparatus and then the volume and the number of the toner particles of 2 μm or larger are measured by the foregoing Coulter Counter TA-II model using 100 μm apertures as apertures and the distribution by volume and the distribution by number are calculated. Then, the weight average particle size (D4) on the bases of the volume calculated from the distribution by volume according to the invention and the length average particle size (D1) on the bases of the number calculated from the distribution by number are calculated.

(Charging Quantity)

That the electrostatic latent image developing toner of the invention has a charging quantity (a two-component manner) per unit weight in a range preferably from $-10$ to $-80\,\mu C/g$, more preferably from $-15$ to $-70\,\mu C/g$ is desirable to improve the transfer efficiency in a transfer method using a transfer member to apply voltage thereto.

Figure 7:
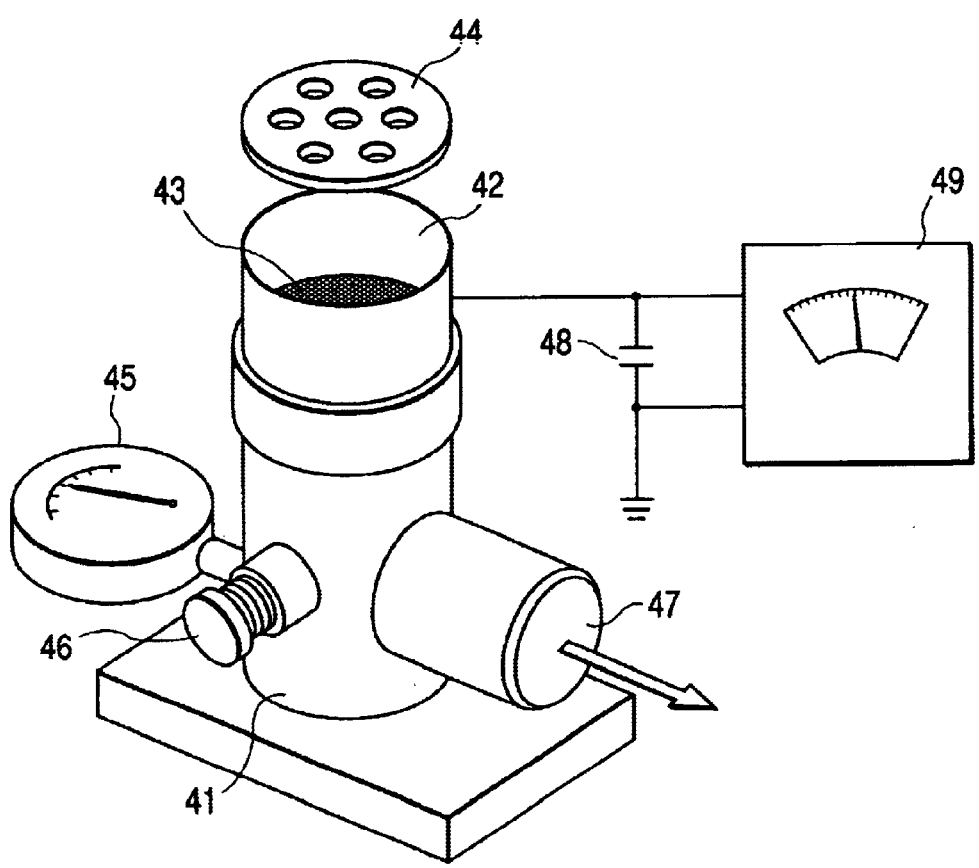
FIG. 7 is a schematic view of a blow-off charge amount measurement apparatus for measuring the charging quantity of a toner.

The measurement method of the charging quantity (a two-component tripo) by the two-component method employed in the invention will be described as follows. A charging quantity measurement apparatus illustrated in FIG. 7 is used for the measurement. At first, under a specified environment, EFV 200/300 (produced by Powdertech Co.) is used as a carrier and a bottle made of a polyethylene with a capacity of 50 to 100 ml is charged with a mixture of 9.5 g of the carrier and 0.5 g of a toner, an object to be measured, set in a shaking apparatus so controlled as to keep the amplitude constant, and shaken for a prescribed period in the shaking conditions of an amplitude of 100 mm and a shaking speed of 100 time reciprocation per 1 minute. Then, 1.0 to 1.2 g of the foregoing mixture is fed to a measurement container 42 made of a metal having a mesh screen 43 in the bottom 500 and a cover 44 made of a metal is put on. The entire weight of the measurement container 42 at that time is weighed and denoted as W1 (g). Next, the gas in the container is aspirated through a suction port 47 by an un-illustrated aspirator (at least the portion contacting the measurement container 22 is made of an insulator) and an air ventilation adjustment valve 45 is controlled to control the pressure of the vacuum meter 45 to be 2,450 Pa (250 mmAq). Under such a state, aspiration is carried out for 1 minute to suck and remove the toner. The potential of a potentiometer 49 at that time is denoted as V (volt). The reference numeral 48 denotes a capacitor and the capacity is denoted as C ($\mu$F). The weight of the entire measurement container after the aspiration is weighed and denoted as W2 (g). The friction charging quantity ($\mu$C/g) of the toner can be calculated according to the following equation from these measurement values.

Friction charging quantity $(\mu C/g) = C \times V/(W1-W2)$ (Molecular Weight Distribution of Binder Resin)

The binder resin to be employed for the constituent materials of the electrostatic latent image developing toner of the invention is preferable to have a peak within a range from 3,000 to 15,000 in a low molecular weight region of the molecular weight distribution measured by GPC, especially, in the case of production by the pulverization method. That is, if the GPC peak exceeds 15,000 in the low molecular weight region, it sometimes becomes difficult to obtain a toner with a sufficiently improved transfer efficiency. Whereas if binder resin having a GPC peak of less than 3,000 is used, melting takes place easily at the time of surface treatment and therefore it is undesirable.

In the invention, the molecular weight of the binder resin is measured by GPC (gel permeation chromatography). A practical GPC measurement method is carried out as follows: a toner previously extracted with THF (tetrahydrofuran) solvent for 20 hours using a Soxhlet extractor is used as a sample for measurement and using columns A-801, 802, 803, 804, 805, 806, and 807 manufactured by Showa Denko K.K. and calibration curves of standardized polystyrene resins, the molecular weight distribution is measured. Further, in the invention, it is preferable to use the binder resin having a ratio (Mw/Mn) of the weight average molecular weight (Mw) and the number average molecular weight (Mn) measured as described above within a range from 2 to 100.

(Glass Transition Temperature of Toner)

Further, the toner of the invention is preferable to be adjusted by using proper materials so as to have a glass transition temperature Tg in a range from 40° C. to 75° C., more preferably 52° C. to 70° C., from a viewpoint of the fixation and storage stability. In this case, the measurement of the glass transition temperature Tg may be carried out using a high precision and internally heating input compensation type differential scanning calorimeter, for example, DSC-7 manufactured by Perkin Elmer, Inc. may be employed. The measurement method is carried out according to ASTM D3418-82. In the invention, in the case of measuring the glass transition temperature Tg, it is preferable that a measurement sample is once heated to cancel the entire hysteresis and then quenched and again heated at a heating rate of 10° C./min to employ the DSC curve measured during the heating from 0 to 200° C.

(Image Formation Method)

The electrostatic latent image developing toner of the invention having the above-described constitution is especially preferable to be employed for an image forming method comprising at least a charging step of charging an electrostatic latent image carrier by applying voltage to a charging member from the outside, a step of forming an electrostatic latent image on the charged electrostatic latent image carrier, a development step of developing the electrostatic latent image by the electrostatic latent image developing toner to form a toner image on the electrostatic latent image carrier, a transfer step of transferring the toner image to an object recording material, and a fixation step of fixing the toner image on the recording material by heating fixation, or an image forming method comprising a transfer process involving a first transfer step of transferring the toner image on the electrostatic latent image carrier to an intermediate transfer member and a second transfer step of transferring the toner image on the transfer member to an object recording material.

Hereinafter, the invention will be described more particularly with reference to Examples. These Examples are examples of the best modes of the present invention, yet the invention is not at all restricted to these Examples.

At first, the following Example 1 to Example 3 are examples of production of PHA containing 3-hydroxy-5-(phenylsulfinyl)valeric acid unit defined as the foregoing chemical formula (9) and 3-hydroxy-5-(phenylsulfonyl) valeric acid unit defined as the foregoing chemical formula (10) and in addition to them, at least one of chlorine-substituted units selected from four kinds of units; 5-chloro-3-hydroxy-5-(phenylsulfinyl)valeric acid unit defined as chemical formula (11), 5-chloro-3-hydroxy-5-(phenylsulfonyl)valeric acid unit defined as chemical formula (12), 5,5-dichloro-3-hydroxy-5-(phenylsulfinyl)valeric acid unit defined as chemical formula (13), and 5,5-dichloro-3-hydroxy-5-(phenylsulfonyl)valeric acid unit defined as chemical formula (14) in the polymer molecule and obtained by culturing PHA producing bacteria in a culture medium containing 5-(phenylsulfanyl)valeric acid as a raw material and then treating the PHA produced by the PHA producing bacteria with sodium hypochlorite.

EXAMPLE 1

*Pseudomonas cichorii* YN2 was inoculated in 200 mL of M9 culture medium containing 0.5% polypeptone and cultured in a shaking flask of 500 mL capacity under the conditions of shaking at 30° C. and 125 stroke/min. After 72 hours, 2 mL of the foregoing culture solution was added to 1,000 mL of M9 culture medium containing 0.5% of polypeptone and 0.1% of 5-(phenylsulfanyl)valeric acid and culture was carried out in a shaking flask of 2,000 mL capacity under the conditions of shaking at 30° C. and 125 stroke/min for 23 hours.

The resulting culture solution was centrifuged [78,000 m/s$^2$ (=8,000 G), 4° C., 10 minutes] to recover microorganism cells. The obtained cells were suspended in 40 mL of pure water and 20 mL of an aqueous sodium hypochlorite solution (effective chlorine concentration 5% or higher, produced by Kishida Chemical Co., Ltd.) was added. The resulting mixture was shaken at 4° C. for 2 hours to make the cell constituting components other than PHA soluble and simultaneously oxidize and chlorinate polyhydroxyalkanoate. After completion of the reaction, coarse polyhydroxyalkanoate was recovered by centrifugation [29,400 m/s$^2$ (=3,000 G), 4° C., 30 minutes].

The obtained coarse polyhydroxyalkanoate was washed with water to obtain polyhydroxyalkanoate with a higher refining degree by suspension in 70 mL of pure water and centrifugation [29,400 m/s² (=3,000 G), 4° C., 30 minutes] repeated three times. Then, the obtained polyhydroxyalkanoate was suspended in 10 mL of pure water and freeze-dried to obtain 470 mg of refined polyhydroxyalkanoate particles.

Figure 8:
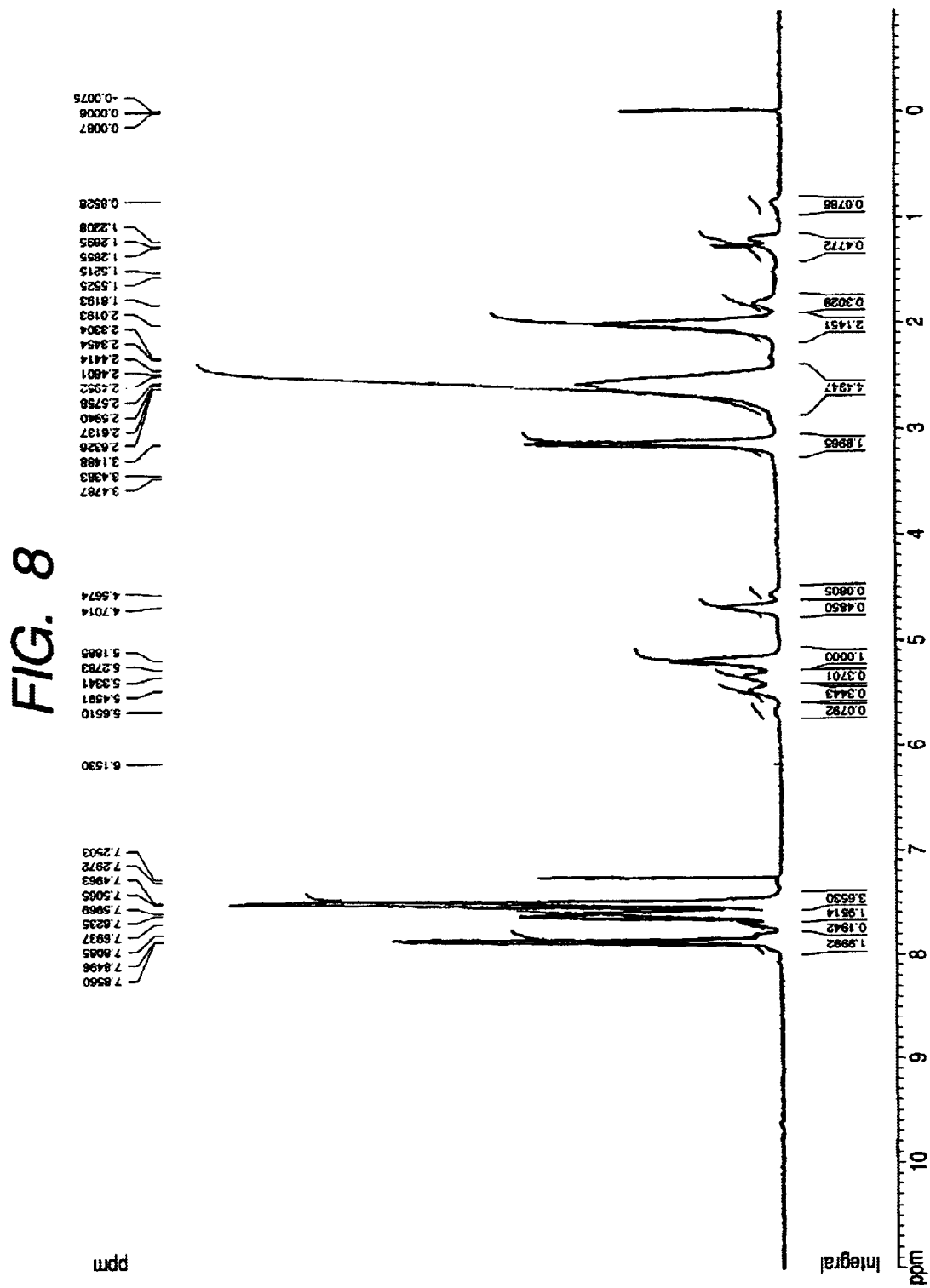
FIG. 8 is $^1$H-NMR spectra of PHA of Example 1.

The obtained polyhydroxyalkanoate was subjected to NMR analysis in the following conditions.
<Measurement Apparatus> FT-NMR: Bruker DPX 400
   resonance frequency: ¹H=400 MHz
   measurement nucleus: ¹H
   solvent used: $CDCl_3$
   reference: capillary-sealed $TMS/CDCl_3$
   measurement temperature: room temperature
FIG. 8 shows the measured ¹H-NMR spectrum chart and Table 1 shows the calculation results of the contents (% by mol) of the contained monomer units based on the identification results.

As a result, the obtained polyhydroxyalkanoate was found to be a polyhydroxyalkanoate containing 3-hydroxy-5-(phenylsulfinyl)valeric acid unit defined as the foregoing chemical formula (9), 3-hydroxy-5-(phenylsulfonyl)valeric acid unit defined as the foregoing chemical formula (10) and, in addition to them, 5-chloro-3-hydroxy-5-(phenylsulfinyl)valeric acid unit defined as chemical formula (11), 5-chloro-3-hydroxy-5-(phenylsulfonyl)valeric acid unit defined as chemical formula (12), 5,5-dichloro-3-hydroxy-5-(phenylsulfinyl)valeric acid unit defined as chemical formula (13), and 5,5-dichloro-3-hydroxy-5-(phenylsulfonyl)valeric acid unit defined as chemical formula (14), and as units other than the above units, a straight chain 3-hydroxyalkanoic acid unit of 4 to 12 carbons defined as the chemical formula (7) or a straight chain 3-hydroxyalkenoic acid unit defined as the chemical formula (8). (Incidentally, in Table 1, the straight chain 3-hydroxyalkanoic acid unit of 4 to 12 carbons defined as the chemical formula (7) or the straight chain 3-hydroxyalkenoic acid unit defined as the chemical formula (8) is also shown as 3HA)

TABLE 1

| Unit type | NMR (mol %) |
|---|---|
| Chemical Formula (9) and Chemical Formula (10) | 53.0 |
| Chemical Formula (11) and Chemical Formula (12) | 35.0 |
| Chemical Formula (13) and Chemical Formula (14) | 3.0 |
| 3HA | 9.0 |

Incidentally, the units defined as the chemical formula (9) and the chemical formula (10), the units defined as the chemical formula (11) and the chemical formula (12), and the units defined as the chemical formula (13) and the chemical formula (14) were difficult to calculate the respective proportions from ¹H-NMR, however the proportions were comprehensively judged based on the results of IR absorption spectrometry and thermal decomposition GC-MS analysis in addition to the NMR analysis to conclude that all of the above-described 6 kinds of units were contained in the polymer.

The obtained polyhydroxyalkanoate was subjected to GPC (gel permeation chromatography) to measure the molecular weight. The conditions of GPC were as follows: apparatus: Tosoh Corporation HLC-8020; column: Polymer Laboratory Plgel MIXED-C (5 µm)×2; mobile phase solvent: DMF containing 0.1% by weight LiBr; conversion into polystyrene. The results were the number average molecular weight (Mn): 14,900, the weight average molecular weight (Mw): 31,100, and Mw/Mn: 2.1.

EXAMPLE 2

*Pseudomonas cichorii* H45 was inoculated in 200 mL of M9 culture medium containing 0.5% polypeptone and cultured in a shaking flask of 500 mL capacity under the conditions of shaking at 30° C. and 125 stroke/min. After 72 hours, 2 mL of the foregoing culture solution was added to 1,000 mL of M9 culture medium containing 0.5% of polypeptone and 0.1% of 5-(phenylsulfanyl)valeric acid and culture was carried out in a shaking flask of 2,000 mL capacity under the conditions of shaking at 30° C. and 125 stroke/min for 23 hours.

The resulting culture solution was centrifuged [78,000 m/s² (=8,000 G), 4° C., 10 minutes] to recover microorganism cells. The obtained cells were treated with sodium hypochlorite in the same conditions as those of Example 1 to obtain 351 mg of refined polyhydroxyalkanoate particles.

EXAMPLE 3

*Pseudomonas jessenii* P161 was inoculated in 200 mL of M9 culture medium containing 0.5% polypeptone and cultured in a shaking flask of 500 mL capacity under the conditions of shaking at 30° C. and 125 stroke/min. After 72 hours, 2 mL of the foregoing culture solution was added to 1,000 mL of M9 culture medium containing 0.5% of polypeptone and 0.1% of 5-(phenylsulfanyl)valeric acid and culture was carried out in a shaking flask of 2,000 mL capacity under the conditions of shaking at 30° C. and 125 stroke/min for 23 hours.

The resulting culture solution was centrifuged [78,000 m/s² (=8,000 G), 4° C., 10 minutes] to recover microorganism cells. The obtained cells were treated with sodium hypochlorite in the same conditions as those of Example 1 to obtain 311 mg of refined polyhydroxyalkanoate particles.

The polyhydroxyalkanoates obtained in Example 2 and Example 3 were subjected to NMR analysis and molecular weight measurement in the same conditions as those of Example 1. The results are shown in Table 2 and Table 3. (In Table 2, the abbreviation 3HA denotes the straight chain 3-hydroxyalkanoic acid unit of 4 to 12 carbons defined as the chemical formula (7) or the straight chain 3-hydroxyalkenoic acid unit defined as the chemical formula (8).)

TABLE 2

| | | Proportion of each unit contained (mol %) | | | |
|---|---|---|---|---|---|
| | PHA particle (mg) | Chemical Formula (9) and Chemical Formula (10) | Chemical Formula (11) and Chemical Formula (12) | Chemical Formula (13) and Chemical Formula (14) | 3HA |
| Example 2 | 351 | 53.3 | 34.2 | 5.0 | 7.5 |
| Example 3 | 311 | 52.3 | 35.0 | 4.2 | 9.5 |

TABLE 3

| | Mn | Mw | Mw/Mn |
|---|---|---|---|
| Example 2 | 16200 | 32100 | 2.0 |
| Example 3 | 16800 | 33400 | 2.0 |

The following Example 4 to Example 9 are examples of production of PHA containing 3-hydroxy-4-(phenylsulfinyl)

butyric acid unit defined as the foregoing chemical formula (15) and 3-hydroxy-4-(phenylsulfonyl)butyric acid unit defined as the foregoing chemical formula (16) and in addition to them, at least one of chlorine-substituted units selected from four kinds of units: 4-chloro-3-hydroxy-4-(phenylsulfinyl)butyric acid unit defined as chemical formula (17), 4-chloro-3-hydroxy-4-(phenylsulfonyl)butyric acid unit defined as chemical formula (18), 4,4-dichloro-3-hydroxy-4-(phenylsulfinyl)butyric acid unit defined as chemical formula (19), and 4,4-dichloro-3-hydroxy-4-(phenylsulfonyl)butyric acid unit defined as chemical formula (20) in the polymer molecule and obtained by culturing PHA producing bacteria in a culture medium containing 4-(phenylsulfanyl)butyric acid as a raw material and then treating the PHA produced by the PHA producing bacteria with sodium hypochlorite.

EXAMPLE 4

*Pseudomonas cichorii* YN2 was inoculated in 1,000 mL of M9 culture medium containing 0.5% glucose and 0.1% of 4-(phenylsulfanyl)butyric acid and cultured in a shaking flask of 2,000 mL capacity under the conditions of shaking at 30° C. and 125 stroke/min. After 72 hours, the microorganism cells were recovered by centrifugation and again suspended in 1,000 mL of M9 culture medium containing 0.5% glucose, 0.1% of 4-(phenylsulfanyl)butyric acid and no nitrogen source ($NH_4Cl$) and cultured in a shaking flask of 2,000 mL capacity under the conditions of shaking at 30° C. and 125 stroke/min. After 48 hours, the microorganism cells were recovered by centrifugation [78,000 m/s$^2$ (=8,000 G), 4° C., 10 minutes] of the foregoing culture solution.

The obtained microorganism cells were suspended in 40 mL of pure water and 20 mL of an aqueous sodium hypochlorite solution (effective chlorine concentration 5% or higher, produced by Kishida Chemical Co., Ltd.) was added. The resulting mixture was shaken at 4° C. for 2 hours to make the cell constituting components other than polyhydroxyalkanoate soluble and simultaneously oxidize and chlorinate the polyhydroxyalkanoate. On completion of the reaction, coarse polyhydroxyalkanoate was recovered by centrifugation [29,400 m/s$^2$ (=3,000 G), 4° C., 30 minutes].

The obtained coarse polyhydroxyalkanoate was washed with water to obtain polyhydroxyalkanoate with a higher refining degree by suspension in 70 mL of pure water and centrifugation [29,400 m/s$^2$ (=3,000 G), 4° C., 30 minutes] repeated three times. Then, the obtained polyhydroxyalkanoate was suspended in 10 mL of pure water and freeze-dried to obtain 631 mg of refined polyhydroxyalkanoate particles.

The obtained polyhydroxyalkanoate was subjected to NMR analysis in the same conditions as those of Example 1. The results are shown in Table 5. The obtained polyhydroxyalkanoate was found to be a polyhydroxyalkanoate containing 3-hydroxy-4-(phenylsulfinyl)butyric acid unit defined as the foregoing chemical formula (15) and 3-hydroxy-4-(phenylsulfonyl)butyric acid unit defined as the foregoing chemical formula (16) and in addition to them, 4-chloro-3-hydroxy-4-(phenylsulfinyl)butyric acid unit defined as chemical formula (17), 4-chloro-3-hydroxy-4-(phenylsulfonyl)butyric acid unit defined as chemical formula (18), 4,4-dichloro-3-hydroxy-4-(phenylsulfinyl) butyric acid unit defined as chemical formula (19), and 4,4-dichloro-3-hydroxy-4-(phenylsulfonyl)butyric acid unit defined as chemical formula (20), and as units other than these above, a straight chain 3-hydroxyalkanoic acid unit of 4 to 12 carbons defined as the chemical formula (7) or a straight chain 3-hydroxyalkenoic acid unit defined as the chemical formula (8). (Incidentally, in Table 4, the straight chain 3-hydroxyalkanoic acid unit of 4 to 12 carbons defined as the chemical formula (7) or the straight chain 3-hydroxyalkenoic acid unit defined as the chemical formula (8) is also shown as 3HA.)

TABLE 4

| Unit type | NMR (mol %) |
| --- | --- |
| Chemical Formula (15) and Chemical Formula (16) | 26.6 |
| Chemical Formula (17) and Chemical Formula (18) | 50.3 |
| Chemical Formula (19) and Chemical Formula (20) | 12.4 |
| 3HA | 10.7 |

Incidentally, the units defined as Chemical Formula (15) and Chemical Formula (16), the units defined as Chemical Formula (17) and Chemical Formula (18), and the units defined as Chemical Formula (19) and Chemical Formula (20) were difficult to calculate the respective proportions from $^1$H-NMR, however the proportions were comprehensively judged based on the results of IR absorption spectrometry and thermal decomposition GC-MS analysis in addition to the NMR analysis to conclude that all of the above-described 6 kinds of units were contained in the polymer.

The molecular weight measurement was carried out in the same conditions as those of Example 1 and found as follows: the number average molecular weight (Mn): 2,200, the weight average molecular weight (Mw): 5,800, and Mw/Mn: 2.6.

EXAMPLE 5

*Pseudomonas cichorii* YN2 was inoculated in 1,000 mL of M9 culture medium containing 0.5% polypeptone and 0.1% of 4-(phenylsulfanyl)butyric acid and cultured in a shaking flask of 2,000 mL capacity under the conditions of shaking at 30° C. and 125 stroke/min. After 47 hours, the microorganism cells were recovered by centrifugation and again suspended in 1000 mL of M9 culture medium containing 0.5% sodium pyruvate, 0.1% of 4-(phenylsulfanyl) butyric acid and no nitrogen source ($NH_4Cl$) and cultured by shaking at 30° C. and 125 stroke/min. After 48 hours, the microorganism cells were recovered by centrifugation [78,000 m/s$^2$ (=8,000 G), 4° C., 10 minutes] of the foregoing culture solution. The obtained microorganism cells were treated with sodium hypochlorite in the same conditions as those of Example 1 to obtain 531 mg of polyhydroxyalkanoate particles.

EXAMPLE 6

*Pseudomonas cichorii* YN2 was inoculated in 1,000 mL of M9 culture medium containing 0.5% glycerol and 0.1% of 4-(phenylsulfanyl)butyric acid and cultured in a shaking flask of 2,000 mL capacity under the conditions of shaking at 30° C. and 125 stroke/min. After 47 hours, the microorganism cells were recovered by centrifugation and again suspended in 1000 mL of M9 culture medium containing 0.5% glycerol, 0.1% of TPxBA and no nitrogen source ($NH_4Cl$) and further cultured by shaking at 30° C. and 125 stroke/min. After 48 hours, the microorganism cells were recovered by centrifugation [78,000 m/s$^2$ (=8,000 G), 4° C., 10 minutes] of the foregoing culture solution. The obtained microorganism cells were treated with sodium hypochlorite in the same conditions as those of Example 1 to obtain 473 mg of polyhydroxyalkanoate particles.

EXAMPLE 7

*Pseudomonas cichorii* YN2 was inoculated in 1,000 mL of M9 culture medium containing 0.5% yeast extract and 0.1% of 4-(phenylsulfanyl)butyric acid and cultured in a shaking flask of 2,000 mL capacity under the conditions of shaking at 30° C. and 125 stroke/min. After 48 hours, the microorganism cells were recovered by centrifugation [78,000 m/s$^2$ (=8,000 G), 4° C., 10 minutes] of the foregoing culture solution. The obtained microorganism cells were treated with sodium hypochlorite in the same conditions as those of Example 1 to obtain 55 mg of polyhydroxyalkanoate particles.

EXAMPLE 8

*Pseudomonas cichorii* YN2 was inoculated in 1,000 mL of M9 culture medium containing 0.5% glutamic acid and 0.1% of 4-(phenylsulfanyl)butyric acid and cultured in a shaking flask of 2,000 mL capacity under the conditions of shaking at 30° C. and 125 stroke/min. After 47 hours, the microorganism cells were recovered by centrifugation [78,000 m/s$^2$ (=8,000 G), 4° C., 10 minutes] of the foregoing culture solution. The obtained microorganism cells were treated with sodium hypochlorite in the same conditions as those of Example 1 to obtain 228 mg of polyhydroxyalkanoate particles.

EXAMPLE 9

*Pseudomonas cichorii* YN2 was inoculated in 1,000 mL of M9 culture medium containing 0.1% nonanoic acid and 0.1% of 4-(phenylsulfanyl)butyric acid and cultured in a shaking flask of 2,000 mL capacity under the conditions of shaking at 30° C. and 125 stroke/min. After 47 hours, the microorganism cells were recovered by centrifugation [78,000 m/s$^2$ (=8,000 G), 4° C., 10 minutes] of the foregoing culture solution. The obtained microorganism cells were treated with sodium hypochlorite in the same conditions as those of Example 1 to obtain 189 mg of polyhydroxyalkanoate particles.

The polyhydroxyalkanoates obtained in Example 5 to Example 9 were subjected to NMR analysis and molecular weight measurement in the same conditions as those of Example 1. The results are shown in Table 5 and Table 6. (In Table 5, the abbreviation 3HA denotes the straight chain 3-hydroxyalkanoic acid unit of 4 to 12 carbons defined as the chemical formula or 3-hydroxyalkenoic acid unit defined as the chemical formula (7) or chemical formula (8).)

TABLE 5

| | PHA particle (mg) | Proportion of each unit contained (mol %) | | | |
|---|---|---|---|---|---|
| | | Chemical Formula (15) and Chemical Formula (16) | Chemical Formula (17) and Chemical Formula (18) | Chemical Formula (19) and Chemical Formula (20) | 3HA |
| Example 5 | 531 | 27.3 | 51.6 | 13.7 | 7.4 |
| Example 6 | 473 | 26.6 | 52.8 | 10.8 | 9.8 |
| Example 7 | 55 | 24.9 | 45.2 | 12.5 | 17.4 |
| Example 8 | 228 | 28.1 | 52.6 | 13.8 | 5.5 |
| Example 9 | 189 | 2.1 | 3.8 | 1.1 | 93.0 |

TABLE 6

| | Mn | Mw | Mw/Mn |
|---|---|---|---|
| Example 5 | 2200 | 5700 | 2.6 |
| Example 6 | 2400 | 5800 | 2.4 |
| Example 7 | 2300 | 6000 | 2.6 |
| Example 8 | 2500 | 6300 | 2.5 |
| Example 9 | 2100 | 2600 | 2.7 |

The following Example 10 is an example of production of PHA containing 3-hydroxy-5-[(4-fluorophenyl)sulfinyl]valeric acid unit defined as the foregoing chemical formula (21) and 3-hydroxy-5-[(4-fluorophenyl)sulfonyl]valeric acid unit defined as the foregoing chemical formula (22) and in addition to them, at least one of chlorine-substituted units selected from four kinds of units; 5-chloro-3-hydroxy-5-[(4-fluorophenyl)sulfinyl]valeric acid unit defined as chemical formula (23), 5-chloro-3-hydroxy-5-[(4-fluorophenyl)sulfonyl]valeric acid unit defined as chemical formula (24), 5,5-dichloro-3-hydroxy-5-[(4-fluorophenyl)sulfinyl]valeric acid unit defined as chemical formula (25), and 5,5-dichloro-3-hydroxy-5-[(4-fluorophenyl)sulfonyl]valeric acid unit defined as chemical formula (26) in the polymer molecule and obtained by culturing PHA producing bacteria in a culture medium containing 5-[(4-fluorophenyl)sulfanyl]valeric acid as a raw material and then treating the PHA produced by the PHA producing bacteria with sodium hypochlorite.

EXAMPLE 10

*Pseudomonas cichorii* YN2 was inoculated in 1,000 mL of M9 culture medium containing 0.5% polypeptone and 0.1% of 5-[(4-fluorophenyl)sulfanyl]valeric acid and cultured in a shaking flask of 2,000 mL capacity under the conditions of shaking at 30° C. and 125 stroke/min. After 48 hours, the microorganism cells were recovered by centrifugation [78,000 m/s$^2$ (=8,000 G), 4° C., 10 minutes] of the foregoing culture solution.

The obtained cells were suspended in 40 mL of pure water and 20 mL of an aqueous sodium hypochlorite solution (effective chlorine concentration 5% or higher, produced by Kishida Chemical Co., Ltd.) was added. The resulting mixture was shaken at 4° C. for 2 hours to make the cell constituting components other than PHA soluble and simultaneously oxidize and chlorinate the polyhydroxyalkanoate. On completion of the reaction, coarse polyhydroxyalkanoate was recovered by centrifugation [29,400 m/s$^2$ (=3,000 G), 4° C., 30 minutes].

The obtained coarse polyhydroxyalkanoate was washed with water to obtain polyhydroxyalkanoate with a higher refining degree by suspension in 70 mL of pure water and centrifugation [29,400 m/s$^2$ (=3,000 G), 4° C., 30 minutes] repeated three times. Then, the obtained polyhydroxyalkanoate was suspended in 10 mL of pure water and freeze-dried to obtain 250 mg of refined polyhydroxyalkanoate particles.

The obtained polyhydroxyalkanoate was subjected to NMR analysis in the same conditions as those of Example 1. The results are shown in Table 7. The obtained polyhydroxyalkanoate was found to be PHA containing 3-hydroxy-5-[(4-fluorophenyl)sulfinyl]valeric acid unit defined as the foregoing chemical formula (21) and 3-hydroxy-5-[(4-fluorophenyl)sulfonyl]valeric acid unit defined as the foregoing chemical formula (22) and in addition to them, 5-chloro-3-hydroxy-5-[(4-fluorophenyl)sulfinyl]valeric acid unit defined as chemical formula (23), 5-chloro-3-hydroxy-5-[(4-fluorophenyl)sulfonyl]valeric acid unit defined as chemical formula (24), 5,5-dichloro-3-hydroxy-5-[(4-fluorophenyl)sulfinyl]valeric acid unit defined as chemical formula (25), and 5,5-dichloro-3-hydroxy-5-[(4-fluorophenyl)sulfonyl]valeric acid unit defined as chemical formula (26) and as units other than these above, a straight chain 3-hydroxyalkanoic acid unit of 4 to 12 carbons defined as the chemical formula (7) or a straight chain 3-hydroxyalkenoic acid unit defined as the chemical formula (8). (Incidentally, in Table 7, the straight chain 3-hydroxyalkanoic acid unit of 4 to 12 carbons defined as the chemical formula (7) or the straight chain 3-hydroxyalkenoic acid unit defined as the chemical formula (8) is also shown as 3HA.)

TABLE 7

| Unit type | NMR (mol %) |
|---|---|
| Chemical Formula (21) and Chemical Formula (22) | 33.2 |
| Chemical Formula (23) and Chemical Formula (24) | 31.2 |
| Chemical Formula (25) and Chemical Formula (26) | 3.4 |
| 3HA | 32.2 |

Incidentally, the units defined as Chemical Formula (21) and Chemical Formula (22), the units defined as Chemical Formula (23) and Chemical Formula (24), and the units defined as Chemical Formula (25) and Chemical Formula (26) were difficult to calculate the respective proportions from $^1$H-NMR, however the proportions were comprehensively judged based on the results of IR absorption spectrometry and thermal decomposition GC-MS analysis in addition to the NMR analysis to conclude that all of the above-described 6 kinds of units were contained in the polymer.

The molecular weight measurement was carried out in the same conditions as those of Example 1 and found as follows: the number average molecular weight (Mn): 13,700, the weight average molecular weight (Mw): 24,800, and Mw/Mn: 1.8.

The following Examples 11 to 19 shows examples of producing PHAs containing, in a polymer molecule, 3-hydroxy-5-(phenylsulfinyl)valeric acid unit defined as the foregoing chemical formula (9) and 3-hydroxy-5-(phenylsulfonyl)valeric acid unit defined as the foregoing chemical formula (10), and at least one of four kinds of chloro-substituted units, i.e., 5-chloro-3-hydroxy-5-(phenylsulfinyl)valeric acid unit defined as chemical formula (11), 5-chloro-3-hydroxy-5-(phenylsulfonyl)valeric acid unit defined as chemical formula (12), 5,5-dichloro-3-hydroxy-5-(phenylsulfinyl)valeric acid unit defined as chemical formula (13), and 5,5-dichloro-3-hydroxy-5-(phenylsulfonyl)valeric acid unit defined as chemical formula (14), by culturing PHA producing strain in a culture medium containing 1-(phenylsulfanyl)pentane as a raw material, and then treating PHA produced by the PHA producing strain with sodium hypochlorite.

EXAMPLE 11

*Pseudomonas cichorii* YN2 was inoculated in 200 mL of M9 culture medium containing 0.5% (w/v) polypeptone and cultured in a shaking flask of 500 mL capacity for 12 hours under the conditions of shaking at 30° C. and 125 stroke/min. 1,000 mL of M9 culture medium containing 0.5% (w/v) of glucose was prepared and placed in a shaking flask of 2,000 mL capacity, and it was sterilized by an autoclave. After the flask was taken out from it to room temperature, 1-(phenylsulfanyl)pentane sterilized by a filter was added to the flask so that the concentration of 1-(phenylsulfanyl) pentane was set to 0.1% (v/v). 2 mL of the foregoing culture solution was inoculated, and shaking culture was carried out for 48 hours under the conditions of at 30° C. and 125 stroke/min.

The resulting culture solution was centrifuged [78,000 m/s$^2$ (=8,000 G), 4° C., 10 minutes] to recover microorganism cells.

The obtained cells were suspended in 40 mL of pure water and 20 mL of an aqueous sodium hypochlorite solution (effective chlorine concentration 5% or higher, produced by Kishida Chemical Co., Ltd.) was added. The resulting mixture was shaken at 4° C. for 2 hours to make the cell constituting components other than PHA soluble and simultaneously oxidize and chlorinate polyhydroxyalkanoate. After completion of the reaction, coarse polyhydroxyalkanoate was recovered by centrifugation [29,400 m/s$^2$ (=3,000 G), 4° C., 30 minutes].

The obtained coarse polyhydroxyalkanoate was washed with water to obtain polyhydroxyalkanoate with a higher refining degree by suspension in 70 mL of pure water and centrifugation [29,400 m/s$^2$ (=3,000 G), 4° C., 30 minutes] repeated three times. Then, the obtained polyhydroxyalkanoate was suspended in 10 mL of pure water and freeze-dried to obtain 425 mg of refined polyhydroxyalkanoate particles.

The obtained polyhydroxyalkanoate was found to be a polyhydroxyalkanoate containing 3-hydroxy-5-(phenylsulfinyl)valeric acid unit defined as the foregoing chemical formula (9), 3-hydroxy-5-(phenylsulfonyl)valeric acid unit defined as the foregoing chemical formula (10) and, in addition to them, 5-chloro-3-hydroxy-5-(phenylsulfinyl)valeric acid unit defined as chemical formula (11), 5-chloro-3-hydroxy-5-(phenylsulfonyl)valeric acid unit defined as chemical formula (12), 5,5-dichloro-3-hydroxy-5-(phenylsulfinyl)valeric acid unit defined as chemical formula (13), and 5,5-dichloro-3-hydroxy-5-(phenylsulfonyl)valeric acid unit defined as chemical formula (14), and as units other than the above units, a straight chain 3-hydroxyalkanoic acid unit of 4 to 12 carbons defined as the chemical formula (7) or a straight chain 3-hydroxyalkenoic acid unit defined as the chemical formula (8). (Incidentally, in Table 8, the straight chain 3-hydroxyalkanoic acid unit of 4 to 12 carbons defined as the chemical formula (7) or the straight chain 3-hydroxyalkenoic acid unit defined as the chemical formula (8) is also shown as 3HA)

TABLE 8

| Unit type | NMR (mol %) |
|---|---|
| Chemical Formula (9) and Chemical Formula (10) | 55.2 |
| Chemical Formula (11) and Chemical Formula (12) | 37.8 |
| Chemical Formula (13) and Chemical Formula (14) | 3.5 |
| 3HA | 3.5 |

Incidentally, the units defined as the chemical formula (9) and the chemical formula (10), the units defined as the chemical formula (11) and the chemical formula (12), and the units defined as the chemical formula (13) and the chemical formula (14) were difficult to calculate the respective proportions from $^1$H-NMR, however the proportions were comprehensively judged based on the results of IR absorption spectrometry and thermal decomposition GC-MS analysis in addition to the NMR analysis to conclude that all of the above-described 6 kinds of units were contained in the polymer.

The obtained polyhydroxyalkanoate was subjected to GPC (gel permeation chromatography) to measure the molecular weight. The conditions of GPC were as follows: apparatus: Tosoh Corporation HLC-8020; column: Polymer Laboratory Plgel MIXED-C (5 μm)×2; mobile phase solvent: DMF containing 0.1% by weight LiBr; conversion into polystyrene. The results were the number average molecular weight (Mn): 13,900, the weight average molecular weight (Mw): 29,200, and Mw/Mn: 2.1.

EXAMPLE 12

Pseudomonas cichorii YN2 was inoculated in 200 mL of M9 culture medium containing 0.5% (w/v) polypeptone and cultured in a shaking flask of 500 mL capacity for 12 hours under the conditions of shaking at 30° C. and 125 stroke/min. 1,000 mL of M9 culture medium containing 0.5% (w/v) of polypeptone was prepared and placed in a shaking flask of 2,000 mL capacity, and it was sterilized by an autoclave. After the flask was taken out from it to room temperature, 1-(phenylsulfanyl)pentane sterilized by a filter was added to the flask so that the concentration of 1-(phenylsulfanyl)pentane was set to 0.1% (v/v). 2 mL of the foregoing culture solution was inoculated, and shaking culture was carried out for 48 hours under the conditions of at 30° C. and 125 stroke/min.

The resulting culture solution was centrifuged [78,000 m/s$^2$ (=8,000 G), 4° C., 10 minutes] to recover microorganism cells.

The obtained cells were suspended in 40 mL of pure water and 20 mL of an aqueous sodium hypochlorite solution (effective chlorine concentration 5% or higher, produced by Kishida Chemical Co., Ltd.) was added. The resulting mixture was shaken at 4° C. for 2 hours to make the cell constituting components other than PHA soluble and simultaneously oxidize and chlorinate polyhydroxyalkanoate. After completion of the reaction, coarse polyhydroxyalkanoate was recovered by centrifugation [29,400 m/s$^2$ (=3,000 G), 4° C., 30 minutes].

The obtained coarse polyhydroxyalkanoate was washed with water to obtain polyhydroxyalkanoate with a higher refining degree by suspension in 70 mL of pure water and centrifugation [29,400 m/s$^2$ (=3,000 G), 4° C., 30 minutes] repeated three times. Then, the obtained polyhydroxyalkanoate was suspended in 10 mL of pure water and freeze-dried to obtain 235 mg of refined polyhydroxyalkanoate particles.

EXAMPLE 13

Pseudomonas cichorii YN2 was inoculated in 200 mL of M9 culture medium containing 0.5% (w/v) polypeptone and cultured in a shaking flask of 500 mL capacity for 12 hours under the conditions of shaking at 30° C. and 125 stroke/min. 1,000 mL of M9 culture medium containing 0.5% (w/v) of gultamic acid was prepared and placed in a shaking flask of 2,000 mL capacity, and it was sterilized by an autoclave. After the flask was taken out from it to room temperature, 1-(phenylsulfanyl)pentane sterilized by a filter was added to the flask so that the concentration of 1-(phenylsulfanyl)pentane was set to 0.1% (v/v). 2 mL of the foregoing culture solution was inoculated, and shaking culture was carried out for 48 hours under the conditions of at 30° C. and 125 stroke/min.

The resulting culture solution was centrifuged [78,000 m/s$^2$ (=8,000 G), 4° C., 10 minutes] to recover microorganism cells.

The obtained cells were suspended in 40 mL of pure water and 20 mL of an aqueous sodium hypochlorite solution (effective chlorine concentration 5% or higher, produced by Kishida Chemical Co., Ltd.) was added. The resulting mixture was shaken at 4° C. for 2 hours to make the cell constituting components other than PHA soluble and simultaneously oxidize and chlorinate polyhydroxyalkanoate. After completion of the reaction, coarse polyhydroxyalkanoate was recovered by centrifugation [29,400 m/s$^2$ (=3,000 G), 4° C., 30 minutes].

The obtained coarse polyhydroxyalkanoate was washed with water to obtain polyhydroxyalkanoate with a higher refining degree by suspension in 70 mL of pure water and centrifugation [29,400 m/s$^2$ (=3,000 G), 4° C., 30 minutes] repeated three times. Then, the obtained polyhydroxyalkanoate was suspended in 10 mL of pure water and freeze-dried to obtain 950 mg of refined polyhydroxyalkanoate particles.

EXAMPLE 14

Pseudomonas cichorii YN2 was inoculated in 200 mL of M9 culture medium containing 0.5% (w/v) polypeptone and cultured in a shaking flask of 500 mL capacity for 12 hours under the conditions of shaking at 30° C. and 125 stroke/min. 1,000 mL of M9 culture medium containing 0.5% (w/v) of nonanoic acid was prepared and placed in a shaking flask of 2,000 mL capacity, and it was sterilized by an autoclave. After the flask was taken out from it to room temperature, 1-(phenylsulfanyl)pentane sterilized by a filter was added to the flask so that the concentration of 1-(phenylsulfanyl)pentane was set to 0.1% (v/v). 2 mL of the foregoing culture solution was inoculated, and shaking culture was carried out for 48 hours under the conditions of at 30° C. and 125 stroke/min.

The resulting culture solution was centrifuged [78,000 m/s$^2$ (=8,000 G), 4° C., 10 minutes] to recover microorganism cells.

The obtained cells were suspended in 40 mL of pure water and 20 mL of an aqueous sodium hypochlorite solution (effective chlorine concentration 5% or higher, produced by Kishida Chemical Co., Ltd.) was added. The resulting mixture was shaken at 4° C. for 2 hours to make the cell constituting components other than PHA soluble and simultaneously oxidize and chlorinate polyhydroxyalkanoate. After completion of the reaction, coarse polyhydroxyalkanoate was recovered by centrifugation [29,400 m/s$^2$ (=3,000 G), 4° C., 30 minutes].

The obtained coarse polyhydroxyalkanoate was washed with water to obtain polyhydroxyalkanoate with a higher refining degree by suspension in 70 mL of pure water and centrifugation [29,400 m/s$^2$ (=3,000 G), 4° C., 30 minutes] repeated three times. Then, the obtained polyhydroxyalkanoate was suspended in 10 mL of pure water and freeze-dried to obtain 322 mg of refined polyhydroxyalkanoate particles.

EXAMPLE 15

Pseudomonas cichorii YN2 was inoculated in 200 mL of M9 culture medium containing 0.5% (w/v) polypeptone and cultured in a shaking flask of 500 mL capacity for 12 hours under the conditions of shaking at 30° C. and 125 stroke/min. 1,000 mL of M9 culture medium containing 0.5% (w/v) of yeast extract was prepared and placed in a shaking flask of 2,000 mL capacity, and it was sterilized by an autoclave. After the flask was taken out from it to room temperature, 1-(phenylsulfanyl)pentane sterilized by a filter was added to the flask so that the concentration of 1-(phenylsulfanyl)pentane was set to 0.1% (v/v). 2 mL of the foregoing culture solution was inoculated, and shaking culture was carried out for 48 hours under the conditions of at 30° C. and 125 stroke/min.

The resulting culture solution was centrifuged [78,000 m/s$^2$ (=8,000 G), 4° C., 10 minutes] to recover microorganism cells.

The obtained cells were suspended in 40 mL of pure water and 20 mL of an aqueous sodium hypochlorite solution (effective chlorine concentration 5% or higher, produced by Kishida Chemical Co., Ltd.) was added. The resulting mixture was shaken at 4° C. for 2 hours to make the cell constituting components other than PHA soluble and simultaneously oxidize and chlorinate polyhydroxyalkanoate. After completion of the reaction, coarse polyhydroxyalkanoate was recovered by centrifugation [29,400 m/s$^2$ (=3,000 G), 4° C., 30 minutes].

The obtained coarse polyhydroxyalkanoate was washed with water to obtain polyhydroxyalkanoate with a higher refining degree by suspension in 70 mL of pure water and centrifugation [29,400 m/s$^2$ (=3,000 G), 4° C., 30 minutes] repeated three times. Then, the obtained polyhydroxyalkanoate was suspended in 10 mL of pure water and freeze-dried to obtain 207 mg of refined polyhydroxyalkanoate particles.

EXAMPLE 16

*Pseudomonas cichorii* YN2 was inoculated in 200 mL of M9 culture medium containing 0.5% (w/v) polypeptone and cultured in a shaking flask of 500 mL capacity for 12 hours under the conditions of shaking at 30° C. and 125 stroke/min. 1,000 mL of M9 culture medium containing 0.5% (w/v) of polypeptone was prepared and placed in a shaking flask of 2,000 mL capacity, and it was sterilized by an autoclave. After the flask was taken out from it to room temperature, 1-(phenylsulfanyl)pentane sterilized by a filter was added to the flask so that the concentration of 1-(phenylsulfanyl)pentane was set to 0.1% (v/v). 2 mL of the foregoing culture solution was inoculated, and shaking culture was carried out under the conditions of at 30° C. and 125 stroke/min. When a turbidity at 600 nm became 0.1, dicyclopropylketone was further added so that its concentration became 0.05% (v/v), then the mixture was well stirred and the shaking culture was continued.

After 48 hours, the resulting culture solution was centrifuged [78,000 m/s$^2$ (=8,000 G), 4° C., 10 minutes] to recover microorganism cells.

The obtained cells were suspended in 40 mL of pure water and 20 mL of an aqueous sodium hypochlorite solution (effective chlorine concentration 5% or higher, produced by Kishida Chemical Co., Ltd.) was added. The resulting mixture was shaken at 4° C. for 2 hours to make the cell constituting components other than PHA soluble and simultaneously oxidize and chlorinate polyhydroxyalkanoate. After completion of the reaction, coarse polyhydroxyalkanoate was recovered by centrifugation [29,400 m/s$^2$ (=3,000 G), 4° C., 30 minutes].

The obtained coarse polyhydroxyalkanoate was washed with water to obtain polyhydroxyalkanoate with a higher refining degree by suspension in 70 mL of pure water and centrifugation [29,400 m/s$^2$ (=3,000 G), 4° C., 30 minutes] repeated three times. Then, the obtained polyhydroxyalkanoate was suspended in 10 mL of pure water and freeze-dried to obtain 282 mg of refined polyhydroxyalkanoate particles.

EXAMPLE 17

*Pseudomonas cichorii* YN2 was inoculated in 200 mL of M9 culture medium containing 0.5% (w/v) polypeptone and cultured in a shaking flask of 500 mL capacity for 12 hours under the conditions of shaking at 30° C. and 125 stroke/min. 1,000 mL of M9 culture medium containing 0.5% (w/v) of glucose was prepared and placed in a shaking flask of 2,000 mL capacity, and it was sterilized by an autoclave. After the flask was taken out from it to room temperature, 1-(phenylsulfanyl)pentane sterilized by a filter was added to the flask so that the concentration of 1-(phenylsulfanyl)pentane was set to 0.1% (v/v). 2 mL of the foregoing culture solution was inoculated, and shaking culture was carried out for 90 hours under the conditions of at 30° C. and 125 stroke/min.

The resulting culture solution was centrifuged [78,000 m/s$^2$ (=8,000 G), 4° C., 10 minutes] to recover microorganism cells.

1,000 mL of M9 culture medium containing 0.5% (w/v) sodium pyruvate and not containing NH$_4$Cl as a nitrogen source was prepared and placed in a shaking flask of 2,000 mL capacity, and it was sterilized by an autoclave. After the flask was taken out from it to room temperature, 1-(phenylsulfanyl)pentane sterilized by a filter was added to the flask so that the concentration of 1-(phenylsulfanyl)pentane was set to 0.1% (v/v), and the mixture was well stirred. The recovered strain was again suspended in the culture medium, and shaking culture was carried out for 90 hours under the conditions of at 30° C. and 125 stroke/min.

The resulting culture solution was centrifuged [78,000 m/s$^2$ (=8,000 G), 4° C., 10 minutes] to recover microorganism cells.

The obtained cells were suspended in 40 mL of pure water and 20 mL of an aqueous sodium hypochlorite solution (effective chlorine concentration 5% or higher, produced by Kishida Chemical Co., Ltd.) was added. The resulting mixture was shaken at 4° C. for 2 hours to make the cell constituting components other than PHA soluble and simultaneously oxidize and chlorinate polyhydroxyalkanoate. After completion of the reaction, coarse polyhydroxyalkanoate was recovered by centrifugation [29,400 m/s$^2$ (=3,000 G), 4° C., 30 minutes].

The obtained coarse polyhydroxyalkanoate was washed with water to obtain polyhydroxyalkanoate with a higher refining degree by suspension in 70 mL of pure water and centrifugation [29,400 m/s$^2$ (=3,000 G), 4° C., 30 minutes] repeated three times. Then, the obtained polyhydroxyalkanoate was suspended in 10 mL of pure water and freeze-dried to obtain 602 mg of refined polyhydroxyalkanoate particles.

EXAMPLE 18

*Pseudomonas cichorii* YN2 was inoculated in 200 mL of M9 culture medium containing 0.5% (w/v) polypeptone and cultured in a shaking flask of 500 mL capacity for 12 hours under the conditions of shaking at 30° C. and 125 stroke/min. 1,000 mL of M9 culture medium containing 0.5% (w/v) of glucose was prepared and placed in a shaking flask of 2,000 mL capacity, and it was sterilized by an autoclave. After the flask was taken out from it to room temperature, 1-(phenylsulfanyl)pentane sterilized by a filter was added to the flask so that the concentration of 1-(phenylsulfanyl)pentane was set to 0.1% (v/v). 2 mL of the foregoing culture solution was inoculated, and shaking culture was carried out for 90 hours under the conditions of at 30° C. and 125 stroke/min.

The resulting culture solution was centrifuged [78,000 m/s² (=8,000 G), 4° C., 10 minutes] to recover microorganism cells.

1,000 mL of M9 culture medium containing 0.5% (w/v) glucose and not containing NH₄Cl as a nitrogen source was prepared and placed in a shaking flask of 2,000 mL capacity, and it was sterilized by an autoclave. After the flask was taken out from it to room temperature, 1-(phenylsulfanyl)pentane sterilized by a filter was added to the flask so that the concentration of 1-(phenylsulfanyl)pentane was set to 0.1% (v/v), and the mixture was well stirred. The recovered strain was again suspended in the culture medium, and shaking culture was carried out for 90 hours under the conditions of at 30° C. and 125 stroke/min.

The resulting culture solution was centrifuged [78,000 m/s² (=8,000 G), 4° C., 10 minutes] to recover microorganism cells.

The obtained cells were suspended in 40 mL of pure water and 20 mL of an aqueous sodium hypochlorite solution (effective chlorine concentration 5% or higher, produced by Kishida Chemical Co., Ltd.) was added. The resulting mixture was shaken at 4° C. for 2 hours to make the cell constituting components other than PHA soluble and simultaneously oxidize and chlorinate polyhydroxyalkanoate. After completion of the reaction, coarse polyhydroxyalkanoate was recovered by centrifugation [29,400 m/s² (=3,000 G), 4° C., 30 minutes].

The obtained coarse polyhydroxyalkanoate was washed with water to obtain polyhydroxyalkanoate with a higher refining degree by suspension in 70 mL of pure water and centrifugation [29,400 m/s² (=3,000 G), 4° C., 30 minutes] repeated three times. Then, the obtained polyhydroxyalkanoate was suspended in 10 mL of pure water and freeze-dried to obtain 610 mg of refined polyhydroxyalkanoate particles.

EXAMPLE 19

*Pseudomonas cichorii* YN2 was inoculated in 200 mL of M9 culture medium containing 0.5% (w/v) polypeptone and cultured in a shaking flask of 500 mL capacity for 12 hours under the conditions of shaking at 30° C. and 125 stroke/min. 1,000 mL of M9 culture medium containing 0.5% (w/v) of polypeptone was prepared and placed in a shaking flask of 2,000 mL capacity, and it was sterilized by an autoclave. After the flask was taken out from it to room temperature, 1-(phenylsulfanyl)pentane sterilized by a filter was added to the flask so that the concentration of 1-(phenylsulfanyl)pentane was set to 0.1% (v/v). 2 mL of the foregoing culture solution was inoculated, and shaking culture was carried out for 48 hours under the conditions of at 30° C. and 125 stroke/min.

The resulting culture solution was centrifuged [78,000 m/s² (=8,000 G), 4° C., 10 minutes] to recover microorganism cells.

1,000 mL of M9 culture medium containing 0.5% (w/v) glucose and not containing NH₄Cl as a nitrogen source was prepared and placed in a shaking flask of 2,000 mL capacity, and it was sterilized by an autoclave. After the flask was taken out from it to room temperature, 1-(phenylsulfanyl)pentane sterilized by a filter was added to the flask so that the concentration of 1-(phenylsulfanyl)pentane was set to 0.1% (v/v), and the mixture was well stirred. The recovered strain was again suspended in the culture medium, and shaking culture was carried out for 90 hours under the conditions of at 30° C. and 125 stroke/min.

The resulting culture solution was centrifuged [78,000 m/s² (=8,000 G), 4° C., 10 minutes] to recover microorganism cells.

The obtained cells were suspended in 40 mL of pure water and 20 mL of an aqueous sodium hypochlorite solution (effective chlorine concentration 5% or higher, produced by Kishida Chemical Co., Ltd.) was added. The resulting mixture was shaken at 4° C. for 2 hours to make the cell constituting components other than PHA soluble and simultaneously oxidize and chlorinate polyhydroxyalkanoate. After completion of the reaction, coarse polyhydroxyalkanoate was recovered by centrifugation [29,400 m/s² (=3,000 G), 4° C., 30 minutes].

The obtained coarse polyhydroxyalkanoate was washed with water to obtain polyhydroxyalkanoate with a higher refining degree by suspension in 70 mL of pure water and centrifugation [29,400 m/s² (=3,000 G), 4° C., 30 minutes] repeated three times. Then, the obtained polyhydroxyalkanoate was suspended in 10 mL of pure water and freeze-dried to obtain 587 mg of refined polyhydroxyalkanoate particles.

The polyhydroxyalkanoates obtained in Examples 12 to 19 were subjected to NMR analysis and molecular weight measurement in the same conditions as those of Example 1. The results are shown in Table 9 and Table 10. (In Table 9, the abbreviation 3HA denotes the straight chain 3-hydroxyalkanoic acid unit of 4 to 12 carbons defined as the chemical formula (7) or the straight chain 3-hydroxyalkenoic acid unit defined as the chemical formula (8).)

TABLE 9

| | PHA particle (mg) | Proportion of each unit contained (mol %) | | | |
|---|---|---|---|---|---|
| | | Chemical Formula (9) and Chemical Formula (10) | Chemical Formula (11) and Chemical Formula (12) | Chemical Formula (13) and Chemical Formula (14) | 3HA |
| Example 12 | 235 | 38.1 | 22.8 | 2.3 | 36.8 |
| Example 13 | 950 | 6.9 | 2.7 | 0.3 | 90.1 |
| Example 14 | 322 | 4.9 | 3.0 | 0.1 | 92.0 |
| Example 15 | 207 | 38.2 | 20.8 | 3.5 | 37.5 |
| Example 16 | 282 | 42.1 | 23.5 | 3.1 | 31.3 |
| Example 17 | 602 | 52.1 | 33.2 | 3.3 | 11.4 |
| Example 18 | 610 | 51.4 | 32.1 | 3.4 | 13.1 |
| Example 19 | 587 | 53.7 | 34.9 | 3.3 | 7.1 |

TABLE 10

| | Mn | Mw | Mw/Mn |
|---|---|---|---|
| Example 12 | 14200 | 29800 | 2.1 |
| Example 13 | 12900 | 25800 | 2.0 |
| Example 14 | 13200 | 27700 | 2.1 |
| Example 15 | 13900 | 29300 | 2.1 |
| Example 16 | 11000 | 24100 | 2.2 |
| Example 17 | 12500 | 26000 | 2.0 |
| Example 18 | 12800 | 26900 | 2.1 |
| Example 19 | 12100 | 25400 | 2.1 |

The following Example 20 is an example of production of PHA containing 3-hydroxy-5-[(4-methylphenyl)sulfinyl]valeric acid unit defined as the following chemical formula (30) and 3-hydroxy-5-[(4-methylphenyl)sulfonyl]valeric acid unit defined as the following chemical formula (31) and, in addition to them, at least one of chlorine-substituted units selected from four kinds of units: 5-chloro-3-hydroxy-5-[(4-methylphenyl)sulfinyl]valeric acid unit defined as the following chemical formula (32), 5-chloro-3-hydroxy-5-[(4-methylphenyl)sulfonyl]valeric acid unit defined as the following chemical formula (33), 5,5-dichloro-3-hydroxy-5-[(4-methylphenyl)sulfinyl]valeric acid unit defined as the following chemical formula (34), and 5,5-dichloro-3-hydroxy-5-[(4-methylphenyl)sulfonyl]valeric acid unit defined as the following chemical formula (35) in the polymer molecule and obtained by culturing PHA producing bacteria in a culture medium containing 1-[(4-methylphenyl)sulfanyl]pentane as a raw material and then treating the PHA produced by the PHA producing bacteria with sodium hypochlorite.

EXAMPLE 20

Pseudomonas cichorii YN2 was inoculated in 200 mL of M9 culture medium containing 0.5% (w/v) polypeptone and cultured in a shaking flask of 500 mL capacity for 12 hours under the conditions of shaking at 30° C. and 125 stroke/min. 1,000 mL of M9 culture medium containing 0.5% (w/v) of glucose was prepared and placed in a shaking flask of 2,000 mL capacity, and it was sterilized by an autoclave. After the flask was taken out from it to room temperature, 1-[(4-methylphenyl)sulfanyl]pentane sterilized by a filter was added to the flask so that the concentration of 1-[(4-methylphenyl)sulfanyl]pentane was set to 0.1% (v/v). 2 mL of the foregoing culture solution was inoculated, and shaking culture was carried out for 90 hours under the conditions of at 30° C. and 125 stroke/min.

The resulting culture solution was centrifuged [78,000 m/s$^2$ (=8,000 G), 4° C., 10 minutes] to recover microorganism cells.

1,000 mL of M9 culture medium containing 0.5% (w/v) glucose and not containing $NH_4Cl$ as a nitrogen source was prepared and placed in a shaking flask of 2,000 mL capacity, and it was sterilized by an autoclave. After the flask was taken out from it to room temperature, 1-[(4-methylphenyl)sulfanyl]pentane sterilized by a filter was added to the flask so that the concentration of 1-[(4-methylphenyl)sulfanyl] pentane was set to 0.1% (v/v), and the mixture was well stirred. The recovered strain was again suspended in the culture medium, and shaking culture was carried out for 90 hours under the conditions of at 30° C. and 125 stroke/min.

The resulting culture solution was centrifuged [78,000 m/s$^2$ (=8,000 G), 4° C., 10 minutes] to recover microorganism cells.

The obtained cells were suspended in 40 mL of pure water and 20 mL of an aqueous sodium hypochlorite solution (effective chlorine concentration 5% or higher, produced by Kishida Chemical Co., Ltd.) was added. The resulting mixture was shaken at 4° C. for 2 hours to make the cell constituting components other than PHA soluble and simultaneously oxidize and chlorinate polyhydroxyalkanoate. After completion of the reaction, coarse polyhydroxyalkanoate was recovered by centrifugation [29,400 m/s$^2$ (=3,000 G), 4° C., 30 minutes].

The obtained coarse polyhydroxyalkanoate was washed with water to obtain polyhydroxyalkanoate with a higher refining degree by suspension in 70 mL of pure water and centrifugation [29,400 m/s$^2$ (=3,000 G), 4° C., 30 minutes] repeated three times. Then, the obtained polyhydroxyalkanoate was suspended in 10 mL of pure water and freeze-dried to obtain 348 mg of refined polyhydroxyalkanoate particles.

The obtained coarse polyhydroxyalkanoates were subjected to NMR analysis and molecular weight measurement in the same conditions as those of Example 1. The results are shown in Table 11. The obtained polyhydroxyalkanoates were found to be polyhydroxyalkanoates containing 3-hydroxy-5-[(4-methylphenyl)sulfinyl]valeric acid unit defined as the following chemical formula (30) and 3-hydroxy-5-[(4-methylphenyl)sulfonyl]valeric acid unit defined as the following chemical formula (31) and, in addition to them, 5-chloro-3-hydroxy-5-[(4-methylphenyl)sulfinyl]valeric acid unit defined as the following chemical formula (32), 5-chloro-3-hydroxy-5-[(4-methylphenyl)sulfonyl]valeric acid unit defined as the following chemical formula (33), 5,5-dichloro-3-hydroxy-5-[(4-methylphenyl)sulfinyl]valeric acid unit defined as the following chemical formula (34), and 5,5-dichloro-3-hydroxy-5-[(4-methylphenyl)sulfonyl]valeric acid unit defined as the following chemical formula (35), and as units other than the above units, a straight chain 3-hydroxyalkanoic acid unit of 4 to 12 carbons defined as the chemical formula (7) or a straight chain 3-hydroxyalkenoic acid unit defined as the chemical formula (8). (Incidentally, in Table 11, the straight chain 3-hydroxyalkanoic acid unit of 4 to 12 carbons defined as the chemical formula (7) or the straight chain 3-hydroxyalkenoic acid unit defined as the chemical formula (8) is also shown as 3HA)

TABLE 11

| Unit type | NMR (mol %) |
| --- | --- |
| Chemical Formula (30) and Chemical Formula (31) | 23.0 |
| Chemical Formula (32) and Chemical Formula (33) | 14.1 |
| Chemical Formula (34) and Chemical Formula (35) | 1.7 |
| 3HA | 61.2 |

Incidentally, the units defined as the chemical formula (30) and the chemical formula (31), the units defined as the chemical formula (32) and the chemical formula (33), and the units defined as the chemical formula (34) and the chemical formula (35) were difficult to calculate the respective proportions from $^1$H-NMR, however the proportions were comprehensively judged based on the results of IR absorption spectrometry and thermal decomposition GC-MS analysis in addition to the NMR analysis to conclude that all of the above-described 6 kinds of units were contained in the polymer.

The obtained polyhydroxyalkanoate was subjected to GPC (gel permeation chromatography) to measure the molecular weight. The conditions of GPC were as follows: apparatus: Tosoh Corporation HLC-8020; column: Polymer Laboratory Plgel MIXED-C (5 μm)×2; mobile phase solvent: DMF containing 0.1% by weight LiBr; conversion into polystyrene. The results were the number average molecular weight (Mn): 8,200, the weight average molecular weight (Mw): 16,300, and Mw/Mn: 2.0.

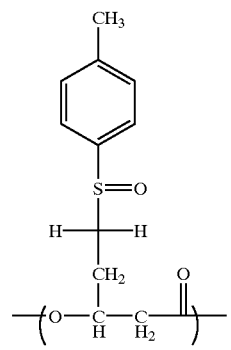

(30)

-continued

(31) 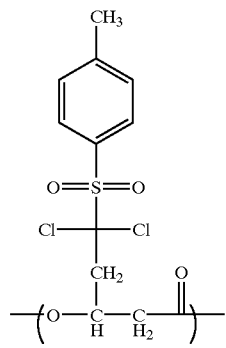

(35)

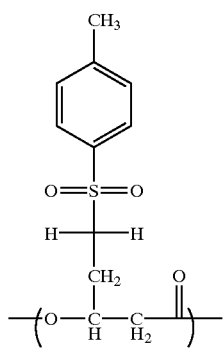

(32)

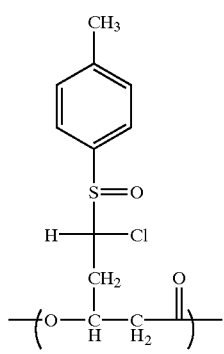

The compounds obtained in the above-described Examples 1, 4, 10 were used as exemplified compound (1), (2), (3), respectively, as shown in Table 12.

TABLE 12

| | |
|---|---|
| Example 1 | Exemplified Compound (1) |
| Example 4 | Exemplified Compound (2) |
| Example 10 | Exemplified Compound (3) |

Using each of the produced charge control agents, each toner was produced and evaluated (Examples 21 to 60).

EXAMPLE 21

At first, a four neck flask with 2 L capacity and equipped with a high speed mixing apparatus TK-Homomixer was charged with an aqueous $Na_3PO_4$ solution, controlled to be rotated at 10,000 rpm and heated to 60° C. An aqueous solution $CaCl_2$ was gradually added to the flask to produce an aqueous dispersion medium containing extremely small water-insoluble dispersant $Ca_3(PO_4)_2$.

(33) 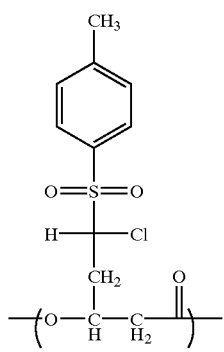

On the other hand, the following composition was dispersed for 3 hours using a ball mill and then 10 parts by weight of a release agent (ester wax) and 10 parts by weight of 2,2'-azobis(2,4-dimethylvaleronitrile) were added to obtain a polymerizable monomer composition:

styrene monomer
  82 parts by weight,
ethyhexyl acrylate monomer
  18 parts by weight,
divinylbenzene monomer
  0.1 parts by weight,
cyan coloring agent (C.I. Pigment Blue 15)
  6 parts by weight,
polyethylene oxide resin (molecular weight 3,200, acid value 8)
  5 parts by weight, and
exemplified compound (1)
  2 parts by weight.

(34) 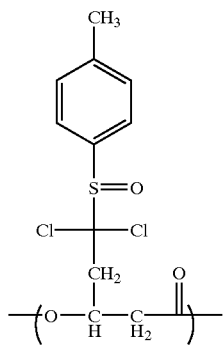

Next, the foregoing obtained polymerizable monomer composition was fed to the previously prepared aqueous dispersion medium and granulated while being rotated at 10,000 rpm. After that, while being stirred by paddle stirring blades, the composition was reacted at 65° C. for 3 hours and then polymerized at 80° C. for 6 hours to complete polymerization reaction. On completion of the reaction, the resulting suspension was cooled, mixed with an acid to dissolve the water-insoluble dispersant $Ca_3(PO_4)_2$ and then filtered, washed with water, and dried to obtain a blue polymer particle (1). The particle size of the obtained blue polymer particle (1) measured by Coulter Counter Multisizer (manufactured by Coulter Co.) was a weight average particle size of 7.1 μm and the fine powder ratio (the existence ratio of particles with 3.17 μm or smaller in the distribution by number) was 5.5% by number.

To 100 parts by weight of the foregoing prepared blue polymer particle, as a fluidity improving agent, 1.3 parts by weight of a hydrophobic silica fine powder (BET: 270 m²/g) treated with hexamethyldisilazane was externally added and mixed in dry state by a Henshel mixer to obtain a blue toner (1) of this example. Further, 7 parts by weight of the blue toner (1) and 93 parts by weight of resin-coated magnetic ferrite carrier (average particle size: 45 μm) were mixed to produce a two-component blue developer (1) for magnetic brush development.

respectively, in conditions of ordinary temperature and ordinary humidify (25° C., 60% RH) and high temperature and high humidify (30° C., 80% RH) according to the above-described electrostatic property measurement method. Further, measured values of two-component blow-off electrostatic properties were rounded to one decimal place and evaluated on the following bases. The results were collectively shown in Table 13.

[Electrostatic Property]
AA: excellent (–20 μC/g or lower),
A: good (–19.9 to –10.0 μC/g),
B: practically usable (–9.9 to –5.0 μC/g),
C: impossible for use (–4.9 μC/g or higher),
Table 13 Electrostatic Property of Blue Toners (1) to (4)

TABLE 13

Electrostatic Property of Blue Toners (1) to (4)

| | | | Particle size distribution | | Ordinary temperature and ordinary humidity (Q/M) | | High temperature and high humidity (Q/M) | |
|---|---|---|---|---|---|---|---|---|
| Example | Compound No. | Toner No.: Blue | Average particle size (μm) | Fine powder content (% by number) | Stir for 10 sec. | Stir for 300 sec. | Stir for 10 sec. | Stir for 300 sec. |
| 21 | 1 | 1 | 7.1 | 5.5 | AA | AA | AA | AA |
| 22 | 2 | 2 | 7.4 | 5.7 | AA | AA | AA | AA |
| 23 | 3 | 3 | 7.2 | 5.6 | AA | AA | AA | AA |
| Comparative Example 1 | — | 4 | 7.0 | 5.2 | C | C | C | C |

EXAMPLE 22 AND 23

Blue toners (2) and (3) of Example 22 and 23 were obtained in the same manner as Example 21 except that each 2.0 parts by weight of the exemplified compounds (2) and (3) were separately used in place of the exemplified compound (1). The properties of the respective toners were measured in the same manner as Example 21 and the results were shown in Table 13. Using the respective toners, two-component blue developers (2) and (3) were respectively obtained in the same manner as Example 21.

COMPARATIVE EXAMPLE 1

Blue toner (4) of Comparative Example 1 was obtained in the same manner as Example 21 except that no exemplified compound was used. The properties of the toner were measured in the same manner as Example 21 and the results were shown in Table 9. Using the toner, a two-component blue developer (4) of Comparative Example 1 was obtained in the same manner as Example 21.

<Evaluation>

The two-component blue developers (1) to (3) obtained in the foregoing Examples 21 to 23 and the two-component blue developer (4) of Comparative Example 1 were subjected to the measurement for measuring the electrostatic properties after stirring for 10 seconds and 300 seconds,

EXAMPLE 24 TO EXAMPLE 26

Yellow toners (1) to (3) of Examples 24 to 26 were obtained in the same manner as Example 21 except that each 2.0 parts by weight of the exemplified compounds (1) to (3) were separately used and a yellow coloring agent (Hansa Yellow G) was used in place of the cyan coloring agent. The properties of 10 these toners were measured in the same manner as Example 21 and the results were shown in Table 14. Using the respective toners, two-component yellow developers (1) to (3) were respectively obtained in the same manner as Example 21.

COMPARATIVE EXAMPLE 2

Yellow toner (4) of Comparative Example 2 was obtained in the same manner as Example 21 except that no exemplified compound was used and a yellow coloring agent (Hansa Yellow G) was used in place of the cyan coloring agent. The properties of the toner were measured in the same manner as Example 21 and the results were shown in Table 14. Using the toner, a two-component yellow developer (4) of Comparative Example 2 was obtained in the same manner as Example 21.

<Evaluation>

The two-component yellow developers (1) to (3) obtained in the foregoing Examples 24 to 26 and the two-component yellow developer (4) obtained in Comparative Example 2 were subjected to the measurement for measuring the electrostatic properties after stirring for 10 seconds and 300 seconds, respectively, in conditions of ordinary temperature and ordinary humidify (25° C., 60% RH) and high temperature and high humidify (30° C., 80% RH) according to the above-described electrostatic property measurement method. Further, measured values of two-component blow-off electrostatic properties were rounded to one decimal place and evaluated on the following bases. The results were collectively shown in Table 10.

[Electrostatic Property]
AA: excellent (−20 μC/g or lower),
A: good (−19.9 to −10.0 μC/g),
B: practically usable (−9.9 to −5.0 μC/g),
C: impossible for use (−4.9 μC/g or higher),
Table 14 Electrostatic Property of Yellow Toners (1) to (4)

TABLE 14

Electrostatic Property of Yellow Toners (1) to (4)

| | | | Particle size distribution | | Electrostatic property | | | |
| | | | | | Ordinary temperature and ordinary humidity (Q/M) | | High temperature and high humidity (Q/M) | |
| Example | Compound No. | Toner No.: Yellow | Average particle size (μm) | Fine powder content (% by number) | Stir for 10 sec. | Stir for 300 sec. | Stir for 10 sec. | Stir for 300 sec. |
|---|---|---|---|---|---|---|---|---|
| 24 | 1 | 1 | 7.2 | 5.4 | AA | AA | AA | AA |
| 25 | 2 | 2 | 7.5 | 5.8 | AA | AA | AA | AA |
| 26 | 3 | 3 | 7.1 | 5.5 | AA | AA | AA | AA |
| Comparative Example 2 | — | 4 | 7.2 | 4.9 | C | C | C | C |

EXAMPLE 27 TO EXAMPLE 29

Black toners (1) to (3) of Examples 27 to 29 were obtained in the same manner as Example 21 except that each 2.0 parts by weight of the exemplified compounds (1) to (3) were separately used and carbon black (DBP oil absorption capacity 110 mL/100 g) was used in place of the cyan coloring agent. The properties of these toners were measured in the same manner as Example 21 and the results were shown in Table 15. Using the respective toners, two-component black developers (1) to (3) were respectively obtained in the same manner as Example 21.

COMPARATIVE EXAMPLE 3

Black toner (4) of Comparative Example 3 was obtained in the same manner as Example 21 except that no exemplified compound was used and carbon black (DBP oil absorption capacity 110 mL/100 g) was used in place of the cyan coloring agent. The properties of the toner were measured in the same manner as Example 21 and the results were shown in Table 14. Using the toner, a two-component black developer (4) of Comparative Example 3 was obtained in the same manner as Example 21.

<Evaluation>

The two-component black developers (1) to (3) obtained in the foregoing Examples 27 to 29 and the two-component black developer (4) obtained in Comparative Example 3 were subjected to the measurement for measuring the electrostatic properties after stirring for 10 seconds and 300 seconds, respectively, in conditions of ordinary temperature and ordinary humidify (25° C., 60% RH) and high temperature and high humidify (30° C., 80% RH) according to the above-described electrostatic property measurement method. Further, measured values of two-component blow-off electrostatic properties were rounded to one decimal place and evaluated on the following bases. The results were collectively shown in Table 14.

[Electrostatic Property]
AA: excellent (−20 μC/g or lower),
A: good (−19.9 to −10.0 μC/g),
B: practically usable (−9.9 to −5.0 μC/g),
C: impossible for use (−4.9 μC/g or higher).
Table 15 Electrostatic Property of Black Toners (1) to (4)

TABLE 15

Electrostatic Property of Black Toners (1) to (4)

| | | | Particle size distribution | | Electrostatic property | | | |
| | | | | | Ordinary temperature and ordinary humidity (Q/M) | | High temperature and high humidity (Q/M) | |
| Example | Compound No. | Toner No.: Black | Average particle size (μm) | Fine powder content (% by number) | Stir for 10 sec. | Stir for 300 sec. | Stir for 10 sec. | Stir for 300 sec. |
|---|---|---|---|---|---|---|---|---|
| 27 | 1 | 1 | 7.0 | 5.2 | AA | AA | AA | AA |
| 28 | 2 | 2 | 7.4 | 5.5 | AA | AA | AA | AA |

TABLE 15-continued

Electrostatic Property of Black Toners (1) to (4)

| | | | Particle size distribution | | Electrostatic property | | | |
|---|---|---|---|---|---|---|---|---|
| | | | | | Ordinary temperature and ordinary humidity (Q/M) | | High temperature and high humidity (Q/M) | |
| Example | Compound No. | Toner No.: Black | Average particle size (μm) | Fine powder content (% by number) | Stir for 10 sec. | Stir for 300 sec. | Stir for 10 sec. | Stir for 300 sec. |
| 29 | 3 | 3 | 7.2 | 5.4 | AA | AA | AA | AA |
| Comparative Example 3 | — | 4 | 6.9 | 5.3 | C | B | C | B |

EXAMPLE 30

Styrene-butyl acrylate copolymer resin (glass transition temperature 70° C.)
  100 parts by weight,
Magenta pigment (C.I. Pigment Red 114)
  5 parts by weight, and
Exemplified compound (1)
  2 parts by weight.

The above-described composition was mixed and melted and kneaded by a biaxial extruder (L/D=30). After being cooled, the kneaded mixture was coarsely pulverized by a hammer mill and finely pulverized by a jet mill and then classified to obtain a magenta coloring particle (1) by the pulverization method. The magenta coloring particle (1) had a weight average particle diameter 7.1 μm and a fine powder content of 5.0% by number.

To 100 parts by weight of the foregoing prepared magenta coloring particle (1), as a fluidity improving agent, 1.5 parts by weight of a hydrophobic silica fine powder (BET: 250 m²/g) treated with hexamethyldisilazane was externally added and mixed in dry state by a Henshel mixer to obtain a magenta toner (1) of this example. Further, 7 parts by weight of the magenta toner (1) and 93 parts by weight of resin-coated magnetic ferrite carrier (average particle size: 45 μm) were mixed to produce a two-component type magenta developer (1) for magnetic brush development.

EXAMPLES 31 AND 32

Magenta toners (2) and (3) of Examples 31 and 32 were obtained in the same manner as Example 30 except that each 2.0 parts by weight of the exemplified compounds (2) and (3) were separately used in place of the exemplified compound (1). The properties of the respective toners were measured in the same manner as Example 21 and the results were shown in Table 16. Using the respective toners, two-component magenta developers (2) and (3) were respectively obtained in the same manner as Example 30.

COMPARATIVE EXAMPLE 4

Magenta toner (4) of Comparative Example 4 was obtained in the same manner as Example 30 except that no exemplified compound was used. The properties of the toner were measured in the same manner as Example 21 and the results were shown in Table 16. Using the toner, a two-component magenta developer (4) of Comparative Example 4 was obtained in the same manner as Example 30.

<Evaluation>

The two-component magenta developers (1) to (3) obtained in the foregoing Examples 30 to 32 and the two-component magenta developer (4) of Comparative Example 4 were subjected to the measurement for measuring the electrostatic properties after stirring for 10 seconds and 300 seconds, respectively, in conditions of ordinary temperature and ordinary humidify (25° C., 60% RH) and high temperature and high humidify (30° C., 80% RH) according to the above-described electrostatic property measurement method. Further, measured values of two-component blow-off electrostatic properties were rounded to one decimal place and evaluated on the following bases. The results were collectively shown in Table 16.

[Electrostatic Property]
AA: excellent (−20 μC/g or lower),
A: good (−19.9 to −10.0 μC/g),
B: practically usable (−9.9 to −5.0 μC/g),
C: impossible for use (−4.9 μC/g or higher).

Table 16 Electrostatic Property of Magenta Toners (1) to (4)

TABLE 16

Electrostatic Property of Magenta Toners (1) to (4)

|  |  |  | Particle size distribution | | Electrostatic property | | | |
|---|---|---|---|---|---|---|---|---|
|  |  |  | | | Ordinary temperature and ordinary humidity (Q/M) | | High temperature and high humidity (Q/M) | |
| Example | Compound No. | Toner No.: Red | Average particle size (μm) | Fine powder content (% by number) | Stir for 10 sec. | Stir for 300 sec. | Stir for 10 sec. | Stir for 300 sec. |
| 30 | 1 | 1 | 7.1 | 5.1 | AA | AA | AA | AA |
| 31 | 2 | 2 | 7.2 | 5.2 | AA | AA | AA | AA |
| 32 | 3 | 3 | 7.0 | 5.2 | AA | AA | AA | AA |
| Comparative Example 4 | — | 4 | 7.1 | 5.1 | C | B | C | B |

EXAMPLES 33 TO 35

Black toners (5) to (7) of Examples 33 to 35 were obtained in the same manner as Example 30 except that each 2.0 parts by weight of the exemplified compounds (1) to (3) were separately used and carbon black (DBP oil absorption capacity 110 mL/100 g) was used in place of the magenta pigment. The properties of these toners were measured in the same manner as Example 21 and the results were shown in Table 17. Using the respective toners, two-component black developers (5) to (7) were respectively obtained in the same manner as Example 30.

COMPARATIVE EXAMPLE 5

Black toner (8) of Comparative Example 5 was obtained in the same manner as Example 30 except that no exemplified compound was used and carbon black (DBP oil absorption capacity 110 mL/100 g) was used in place of the magenta pigment. The properties of the toner were measured in the same manner as Example 21 and the results were shown in Table 17. Using the toner, a two-component black developer (8) of Comparative Example 5 was obtained in the same manner as Example 30.

<Evaluation>

The two-component black developers (5) to (7) obtained in the foregoing Examples 33 to 35 and the two-component black developer (8) obtained in Comparative Example 5 were subjected to the measurement for measuring the electrostatic properties after stirring for 10 seconds and 300 seconds, respectively, in conditions of ordinary temperature and ordinary humidify (25° C., 60% RH) and high temperature and high humidify (30° C., 80% RH) according to the above-described electrostatic property measurement method. Further, measured values of two-component blow-off electrostatic properties were rounded to one decimal place and evaluated on the following bases. The results were collectively shown in Table 17.

[Electrostatic Property]
AA: excellent (−20 μC/g or lower),
A: good (−19.9 to −10.0 μC/g),
B: practically usable (−9.9 to −5.0 μC/g),
C: impossible for use (−4.9 μC/g or higher).

Table 17 Electrostatic Property of Black Toners (5) to (8)

TABLE 17

Electrostatic Property of Black Toners (5) to (8)

|  |  |  | Particle size distribution | | Electrostatic property | | | |
|---|---|---|---|---|---|---|---|---|
|  |  |  | | | Ordinary temperature and ordinary humidity (Q/M) | | High temperature and high humidity (Q/M) | |
| Example | Compound No. | Toner No.: Black | Average particle size (μm) | Fine powder content (% by number) | Stir for 10 sec. | Stir for 300 sec. | Stir for 10 sec. | Stir for 300 sec. |
| 33 | 1 | 5 | 7.2 | 5.2 | AA | AA | AA | AA |
| 34 | 2 | 6 | 7.4 | 5.3 | A | AA | A | AA |
| 35 | 3 | 7 | 7.3 | 5.1 | AA | AA | AA | AA |
| Comparative Example 5 | — | 8 | 7.0 | 5.7 | C | B | C | C |

EXAMPLE 36

Polyester resin
  100 parts by weight,
Carbon black (DBP oil absorption capacity 110 mL/100 g)
  5 parts by weight, and
Exemplified compound (1)
  2 parts by weight.

The polyester resin was synthesized as follows:
751 parts by weight of bisphenol A-propylene oxide 2 mole adduct, 104 parts by weight of terephthalic acid, and 167 parts by weight of trimellitic acid anhydride were condensation-polymerized using 2 parts by weight of dibutyl tin oxide as a catalyst to obtain the polyester resin having a softening point of 125° C.

The above-described composition was mixed and melted and kneaded by a biaxial extruder (L/D=30). After being cooled, the kneaded mixture was coarsely pulverized by a hammer mill and finely pulverized by a jet mill and then classified to obtain a black coloring particle (9) by the pulverization method. The black coloring particle (9) had a weight average particle diameter 7.9 μm and a fine powder content of 4.5% by number.

To 100 parts by weight of the foregoing prepared black coloring particle (9), as a fluidity improving agent, 1.5 parts by weight of a hydrophobic silica fine powder (BET: 250 m$^2$/g) treated with hexamethyldisilazane was externally added and mixed in dry state by a Henshel mixer to obtain a black toner (9) of this example. Further, 7 parts by weight of the black toner (9) and 93 parts by weight of resin-coated magnetic ferrite carrier (average particle size: 45 μm) were mixed to produce a two-component type black developer (9) for magnetic brush development.

EXAMPLE 37 AND EXAMPLE 38

Black toners (10) and (11) of Examples 37 and 38 were obtained in the same manner as Example 36 except that each 2.0 parts by weight of the exemplified compounds (2) and (3) were separately used in place of the exemplified compound (1). The properties of the respective toners were measured in the same manner as Example 21 and the results were shown in Table 18. Using the respective toners, two-component black developers (10) and (11) were respectively obtained in the same manner as Example 36.

COMPARATIVE EXAMPLE 6

Black toner (12) of Comparative Example 6 was obtained in the same manner as Example 36 except that no exemplified compound was used. The properties of the toner were measured in the same manner as Example 21 and the results were shown in Table 18. Using the toner, a two-component black developer (12) of Comparative Example 6 was obtained in the same manner as Example 36.

<Evaluation>

The two-component black developers (9) to (11) obtained in the foregoing Examples 36 to 38 and the two-component black developer (12) of Comparative Example 6 were subjected to the measurement for measuring the electrostatic properties after stirring for 10 seconds and 300 seconds, respectively, in conditions of ordinary temperature and ordinary humidify (25° C., 60% RH) and high temperature and high humidify (30° C., 80% RH) according to the above-described electrostatic property measurement method. Further, measured values of two-component blow-off electrostatic properties were rounded to one decimal place and evaluated on the following bases. The results were collectively shown in Table 18.

[Electrostatic Property]
AA: excellent (−20 μC/g or lower),
A: good (−19.9 to −10.0 μC/g),
B: practically usable (−9.9 to −5.0 μC/g),
C: impossible for use (−4.9 μC/g or higher).

Table 18 Electrostatic Property of Black Toners (9) to (12)

TABLE 18

Electrostatic Property of Black Toners (9) to (12)

| Example | Compound No. | Toner No.: Black | Particle size distribution Average particle size (μm) | Particle size distribution Fine powder content (% by number) | Ordinary temperature and ordinary humidity (Q/M) Stir for 10 sec. | Ordinary temperature and ordinary humidity (Q/M) Stir for 300 sec. | High temperature and high humidity (Q/M) Stir for 10 sec. | High temperature and high humidity (Q/M) Stir for 300 sec. |
|---|---|---|---|---|---|---|---|---|
| 36 | 1 | 9 | 7.9 | 4.5 | AA | AA | AA | AA |
| 37 | 2 | 10 | 8.0 | 4.8 | AA | AA | AA | AA |
| 38 | 3 | 11 | 7.8 | 4.7 | AA | AA | AA | AA |
| Comparative Example 6 | — | 12 | 7.5 | 4.9 | C | B | C | B |

EXAMPLE 39 TO EXAMPLE 56 AND COMPARATIVE EXAMPLE 7 TO COMPARATIVE EXAMPLE 12

At first, an image forming apparatus employed for an image forming method for Example 29 to Example 46 and Comparative Example 7 to Comparative Example 12 will be described. FIG. 1 is a schematic illustration of a cross-section of the image forming apparatus for performing the image forming method of these examples of the invention and comparative examples. The photosensitive drum 1 shown in FIG. 1 had a photosensitive layer 1a containing an organic photo-semiconductor on a substrate 1b and was made possible to be rotated in the direction shown as an arrow and charged to have a surface potential of about −600 V by a charging roller 2, a charging member, which was on the opposite to the photosensitive drum 1 and rotating while being brought into contact with the drum. As shown in FIG. 1, the charging roller 2 was composed of a core metal 2b and a conductive elastic layer 2a formed on the core metal 2b.

Figure 2:
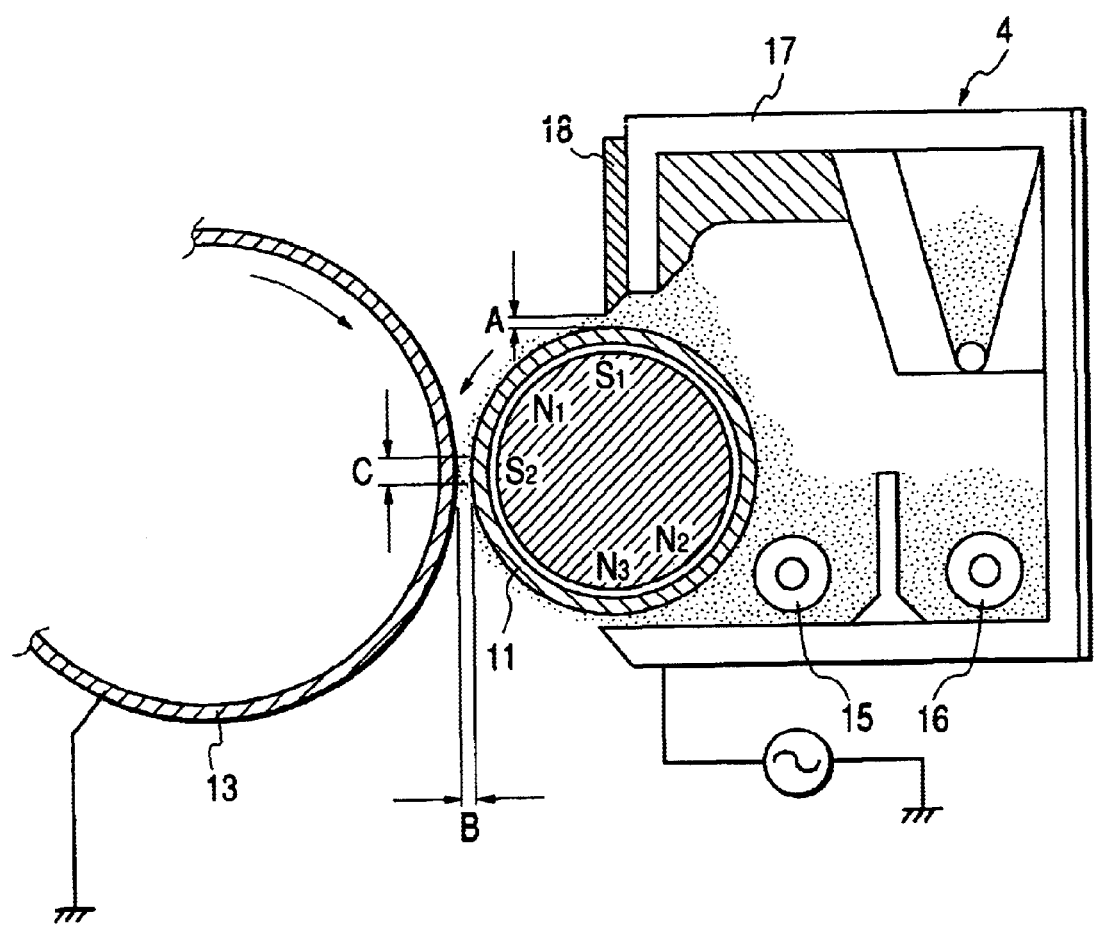
FIG. 2 is a cross-sectional view of a main portion of a developing apparatus for two-component developer employed for Example 39 to Example 56 and Comparative Example 7 to Comparative Example 12.

Next, the surface-charged photosensitive drum 1 was exposed to light 3 and at that time, the exposure of the photosensitive member was turned on and off responding to the digital image information by a polygon mirror to form an electrostatic latent image with an electric potential of −100 V in the exposed areas and −600 V in the dark areas. Successively, the electrostatic latent image on the photosensitive drum 1 was reversely developed by a plurality of development devices 4-1, 4-2, 4-3, and 4-4 to form an apparent image and obtain a toner image on the photosensitive drum 1. At that time, as the developer, the two-component type developers obtained in Examples 21 to 38 and Comparative Examples 1 to 6 were respectively used and toner images of the yellow toners, magenta toners, cyan toners, or black toners were formed. FIG. 2 shows a magnified cross-sectional view of a main portion of the respective development devices 4 for two-component developers employed in that case.

Next, the toner image on the photosensitive drum 1 was transferred to an intermediate transfer member 5 being rotated while being brought into contact with the photosensitive drum 1. As a result, a four color-overlaid apparent color image was formed. The transfer-residual toners remaining in the photosensitive drum 1 without being transferred were recovered in a residual toner container 9 by a cleaner member 8.

The intermediate transfer member 5, as illustrated in FIG. 1, was composed of a core metal 5b as a support member and an elastic layer 5a formed thereon. In this example, an intermediate transfer member 5 was composed of a pipe-like core metal 5b and an elastic layer 5a of nitrile-butadiene rubber (NBR), in which carbon black as a conductivity-providing agent was sufficiently dispersed, formed thereon. The hardness of the elastic layer 5b measured according to JIS K-6301 was 30 degrees and the volume resistance value was 109 Ω·cm. The transfer current necessary to transfer a toner image from the photosensitive drum 1 to the intermediate transfer member 5 was about 5 µA, and the current was obtained by applying +500 V from the power source to the core metal 5b.

The four color toner-overlaid apparent color image formed on the intermediate transfer member 5 was transferred to an object transfer material such as paper by a transfer roller 7 and after that, fixed and made firm by a heating fixation apparatus H. The transfer roller 7 comprised a core metal 7b with an outer diameter of 10 mm and an elastic layer 7a of a foamed material of ethylene-propylene-diene type three-dimensional copolymer (EPDM) in which carbon black as a conductivity-providing agent was sufficiently dispersed was formed thereon. The intrinsic volume resistance value of the elastic layer 7a was 106 Ω·cm and the hardness measured according to JIS K-6301 was 35 degrees. The transfer current of 15 µA was applied by applying voltage to the transfer roller 7.

Figure 5:
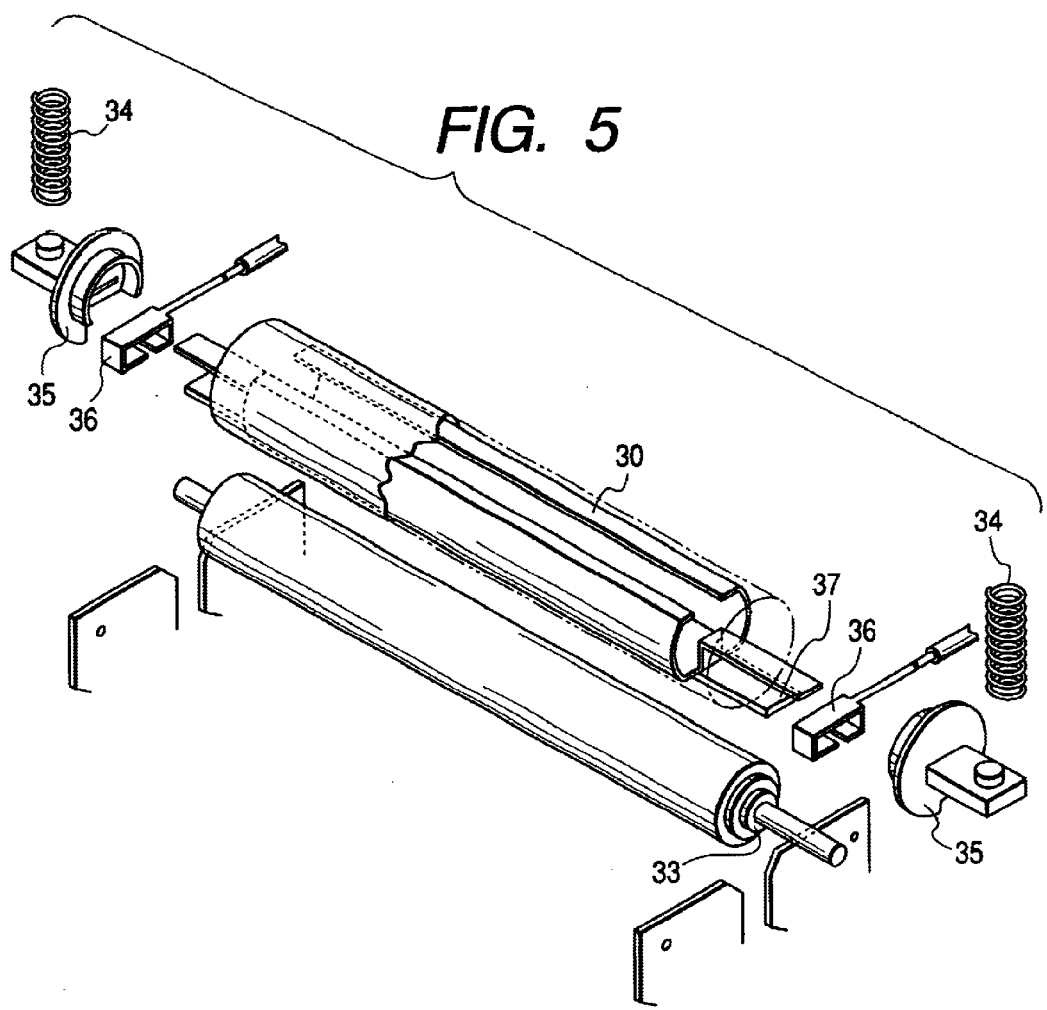
FIG. 5 is a fragmentary perspective view of a main portion of a fixing apparatus employed for Examples of the present invention.
Figure 6:
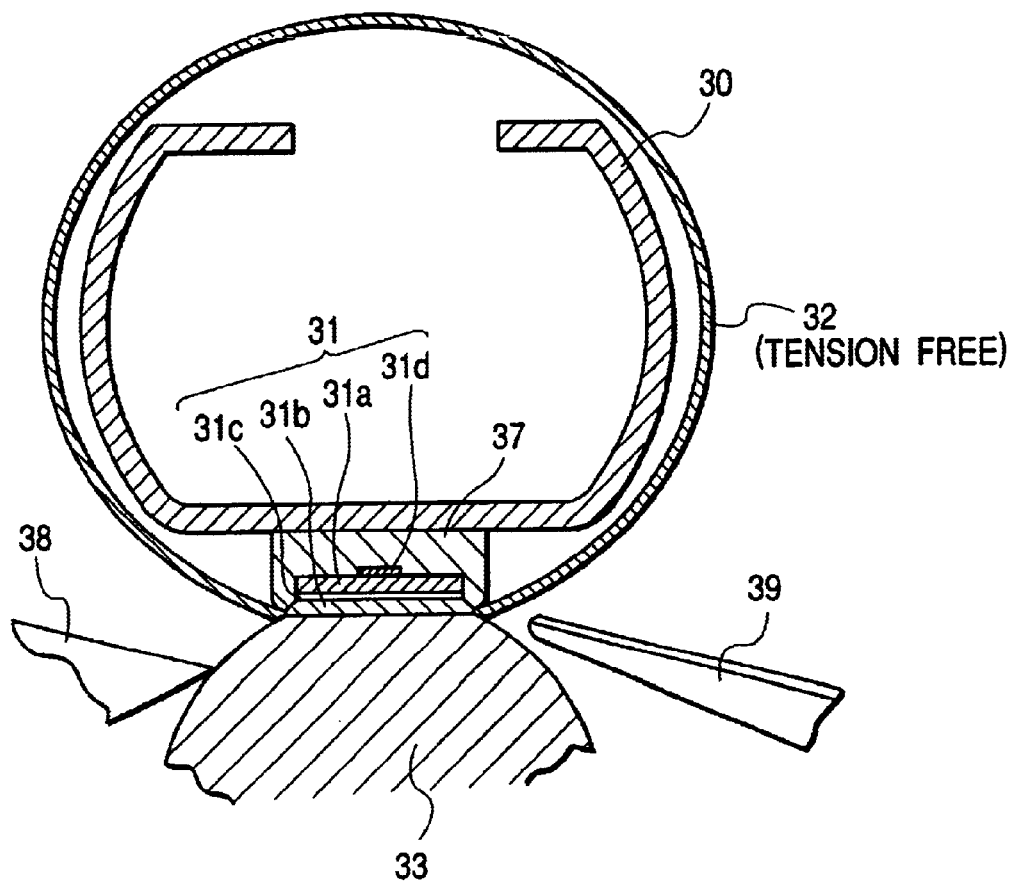
FIG. 6 is a magnified cross-sectional view of a main portion showing a film-like state of a developing apparatus employed for Examples of the invention at the non-operation time.

In the apparatus illustrated in FIG. 1, as the heating fixation apparatus H, a heating roll type fixation apparatus with no oil application mechanism was employed as illustrated in FIG. 5 and FIG. 6. In this case, an upper roller and a lower roller both having surface layers of fluoro resin were employed. The diameter of the rollers was 60 mm. At the time of fixation, the fixation temperature was adjusted at 160° C. and the nip width was set to be 7 mm. The transfer residual toner on the photosensitive drum 1 recovered by cleaning was transported to the developer by a reuse system and used repeatedly.

<Evaluation>

A printing-out test was carried out in the above described manner in the conditions of ordinary temperature and ordinary humidify (25° C., 60% RH) and high temperature and high humidify (30° C., 80% RH) at a printing-out speed of 8 sheets (A4 size)/min using the two-component type developers produced using the toners of Examples 11 to 28 and two-component type developers produced using the toners of Comparative Examples 1 to 6 in a unicolor intermittent mode (that is, a mode in which 10 second-pause of the developing apparatus was performed every one-copy printing-out and toner deterioration was promoted by preliminary operation at the time of restarting) while properly supplementing the toners. The obtained printed-out images were evaluated in the following items. The evaluation results were collectively shown in Table 19.

[Printed-out Image Evaluation]

1. Image Density

Printing out was carried out in a prescribed number of common paper sheets (75 g/m$^2$) for a copying machine and the image density was evaluated base on the degree of the image density retention of a printed-out image on completion of printing to that of a printed-out image at the initial time. The image density was evaluated by measuring the relative density of each printed-out image to the while area with an original image density of 0.00, using Macbeth Reflectometer (manufactured by Macbeth Co.).

AA: excellent (the image density on completion 1.40 or higher)
A: good (the image density on completion not lower than 1.35 and lower than 1.40)
B: fair (the image density on completion not lower than 1.00 and lower than 1.35)
C: poor (the image density on completion lower than 1.00)

2. Image Fogging

Printing out was carried out in a prescribed number of common paper sheets (75 g/m$^2$) and the image fogging was evaluated base on the entirely white image at the time of completion of printing. More particularly, the evaluation was carried out by the following manner. The worst value of the reflection density of the white areas after printing measured using a reflectometer (REFLECTOMETER ODEL TC-6DS, manufactured by TOKYO DENSHOKU CO., LTD.) was defined as Ds and the average value of the reflection density of the paper sheets before printing was defined as Dr and the value (Ds−Dr) was calculated as the fogging and evaluated based on the following.

AA: excellent (the fogging 0% or higher and less than 1.5%)
A: good (the fogging 1.5% or higher and less than 3.0%)
B: practically usable (the fogging 3.0% or higher and less than 5.0%)
C: impossible for use (the fogging 5.0% or higher)

3. Transfer

Printing out of an entirely black image was carried out in a prescribed number of common paper sheets (75 g/m$^2$) and the image depletion of the printed-out image on completion of printing was observed with eye observation and evaluated based on the following.

AA: excellent (scarce occurrence)
A: good (slight)
B: practically usable
C: impossible for use Also, when the occurrence of scratches and adhesion of the residual toner on the surface of the photosensitive drum and intermediate transfer member in the case of forming 5,000 copy printed-out images using two-component type developers of Example 39 to Example 56 and Comparative Example 7 to Comparative Example 12 and the effect on the printed-out images (matching with an image forming apparatus) were evaluated by eye observation, any system using two-component type developers of Example 39 to Example 56 was found causing no scratch and adhesion of the residual toner on the surface of the photosensitive drum and intermediate transfer member, showing excellent matching with the image forming apparatus. Whereas, the systems using two-component type developers of Comparative Example 7 to Comparative Example 12 were all found causing adhesion of the residual toner on the surface photosensitive drum. Further, in the systems using two-component type developers of Comparative Example 7 to Comparative Example 12, adhesion of toners and surface scratching were observed on the surface of the intermediate transfer member to show a problem in the matching with the image forming apparatus such as formation of vertical stripe-like image defects on printed-out images.

cleaner 21 brought into contact with the photosensitive drum 20, then transported to the inside of the cleaner 21 by a cleaner roller, passed through a cleaner reuse 23, and turned back to a developer 26 via a hopper 25 through a supply pipe 24 equipped with a transportation screw for reuse.

Figure 3:
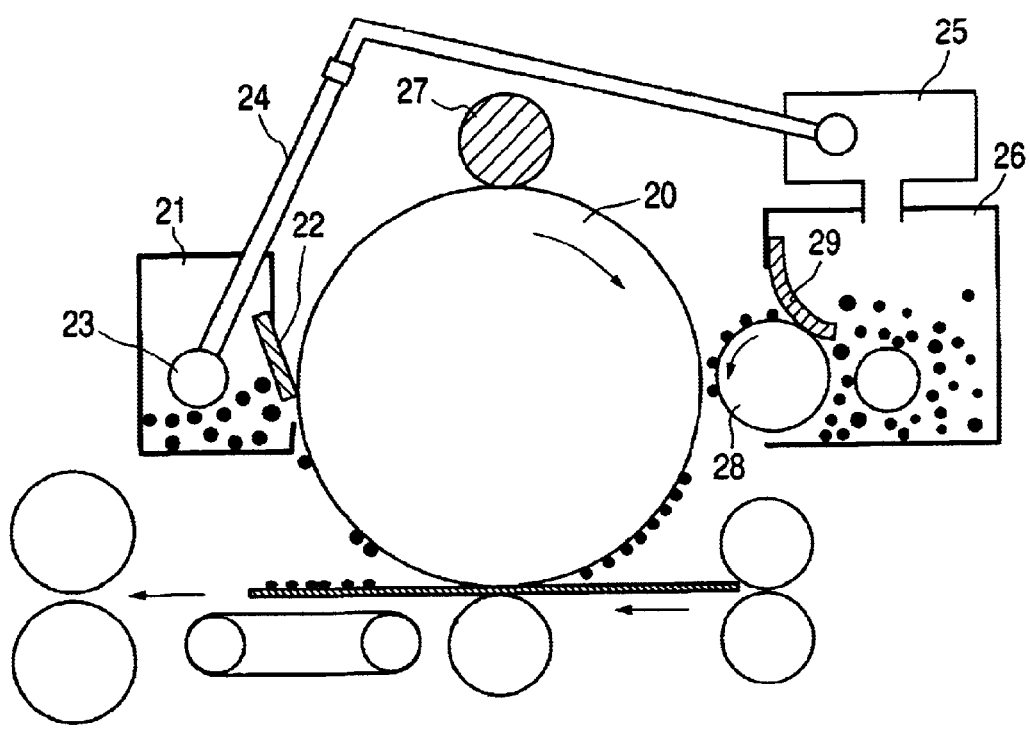
FIG. 3 is a schematic illustration of an image forming apparatus comprising a reuse mechanism of a toner and employed for Example 57 to Example 59 and Comparative Example 13 to Comparative Example 15.

In the image forming apparatus shown in FIG. 3, the surface of the photosensitive drum 20 was charged by a primary charging roller 27. For the primary charging roller 27, a rubber roller (diameter 12 mm, the contacting pressure 50 g/cm) coated with nylon resin and containing dispersed conductive carbon was used and an electrostatic latent image with a dark part potential VD=−700 V and a light part potential VL=−200 V were formed on the electrostatic latent image carrier(the photosensitive drum 20) by laser exposure (600 dpi, unillustrated). As a toner carrier, a developing sleeve 28 coated with resin in which carbon black was dispersed and having the surface roughness Ra of 1.1 was employed.

Figure 4:
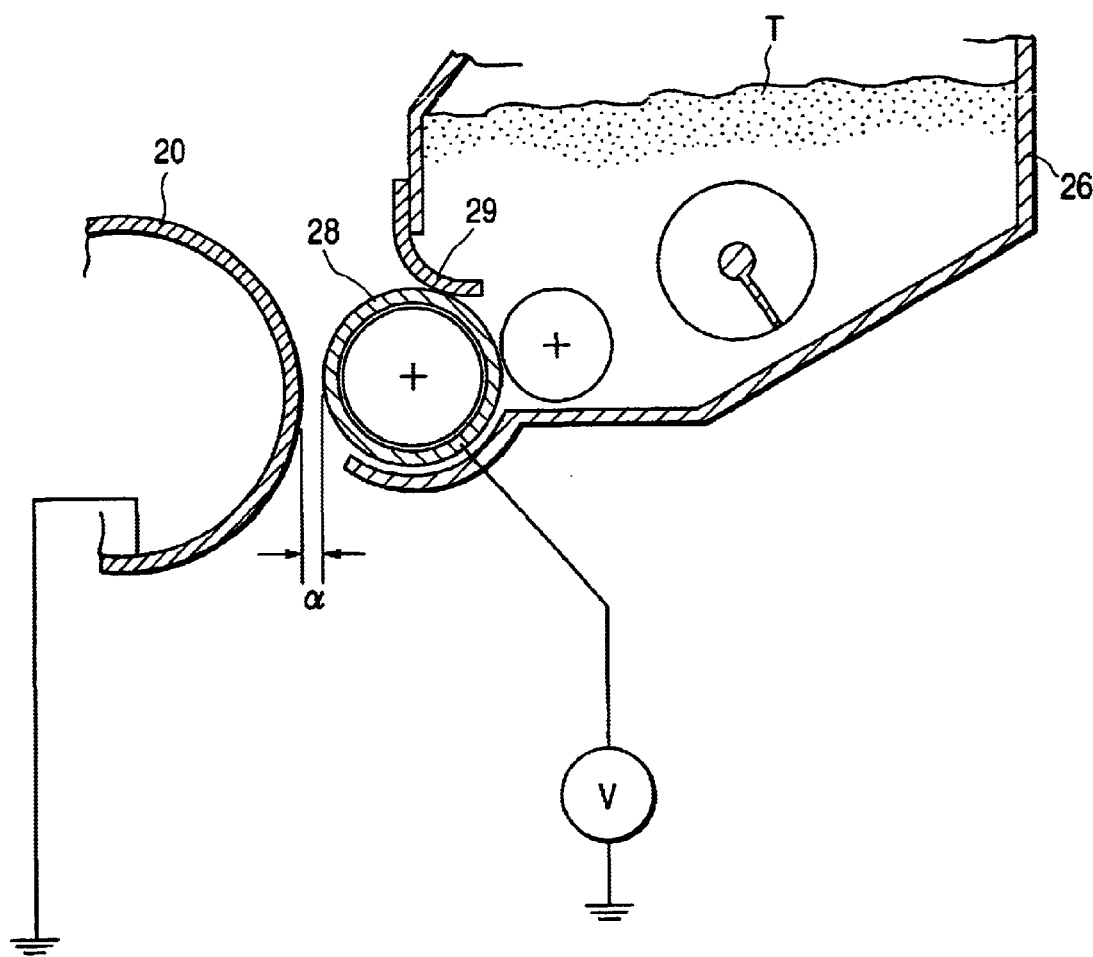
FIG. 4 is a cross-sectional view of a main portion of a developing apparatus for a monocomponent developer employed for Example 57 to Example 59 and Comparative Example 13 to Comparative Example 15.

FIG. 4 shows a magnified cross-sectional view of a main portion of the developing apparatus for a monocomponent type developer employed for Example 57 to Example 59 and

TABLE 19

Result of Printed-Out Image Evaluation

| Example | Two-component developer | Ordinary temperature and ordinary humidity | | | High temperature and high humidity | | |
| --- | --- | --- | --- | --- | --- | --- | --- |
| | | Image density | Image fogging | Transfer | Image density | Image fogging | Transfer |
| 39 | Blue 1 | AA | AA | AA | AA | AA | AA |
| 40 | Blue 2 | AA | AA | AA | A | AA | AA |
| 41 | Blue 3 | AA | AA | AA | AA | AA | AA |
| 42 | Yellow 1 | AA | AA | AA | AA | AA | AA |
| 43 | Yellow 2 | AA | AA | AA | AA | AA | AA |
| 44 | Yellow 3 | AA | AA | AA | AA | AA | AA |
| 45 | Black 1 | AA | AA | AA | AA | AA | AA |
| 46 | Black 2 | AA | AA | AA | AA | AA | AA |
| 47 | Black 3 | AA | AA | AA | AA | AA | AA |
| 48 | Red 1 | AA | AA | AA | AA | AA | AA |
| 49 | Red 2 | AA | AA | AA | AA | AA | AA |
| 50 | Red 3 | AA | AA | AA | AA | AA | AA |
| 51 | Black 5 | AA | AA | AA | AA | AA | AA |
| 52 | Black 6 | AA | AA | AA | AA | AA | AA |
| 53 | Black 7 | AA | AA | AA | AA | AA | AA |
| 54 | Black 9 | AA | AA | AA | AA | AA | AA |
| 55 | Black 10 | AA | AA | AA | AA | AA | AA |
| 56 | Black 11 | AA | AA | AA | AA | AA | AA |
| Comparative Example 7 | Blue 4 | C | C | C | C | C | C |
| 8 | Yellow 4 | C | C | C | C | C | C |
| 9 | Black 4 | B | B | C | B | C | C |
| 10 | Red 4 | B | B | C | B | C | C |
| 11 | Black 8 | B | B | C | C | C | C |
| 12 | Black 12 | B | B | C | B | C | C |

EXAMPLE 57 TO EXAMPLE 59 AND COMPARATIVE EXAMPLE 13 TO COMPARATIVE EXAMPLE 15

Toners obtained in Examples 21, 24, 27 and Comparative Examples 1 to 3 were used as developers for Example 57 to Example 59 and Comparative Example 13 to Comparative Example 15. As means for forming images, as shown in FIG. 3, a reuse mechanism was attached to a commercialized laser beam printer LBP-EX (manufactured by Canon, Inc.) to modify the printer and the obtained printer was reset to be used as an image forming apparatus. That is, in the image forming apparatus shown in FIG. 3, a system for recovering and repeatedly using the toner was attached so that the un-transferred toner remaining on the photosensitive drum 20 after transferring was scraped by an elastic blade 22 of a Comparative Example 13 to Comparative Example 15. The electrostatic latent image developing conditions were so set as to keep the speed of the developing sleeve 28 as 1.1 times fast as that of the moving speed of the photosensitive drum 20 and adjust the gap α (S-D gap) between the photosensitive drum 20 and the developing sleeve 28 to be 270 μm. As a toner thickness regulating member, a blade 29 made of urethane rubber was attached thereto to be employed. The set temperature of a thermally fixing apparatus for fixing the toner image was 160° C. The fixing apparatus illustrated in FIG. 5 and FIG. 6 was employed as the fixing apparatus.

In such a manner, in the conditions of ordinary temperature and ordinary humidity (25° C., 60% RH), 30,000 copy printing-out was carried out at a printing-out speed of 8 sheets (A4 size)/min in a continuous mode (that is, a mode in which toner consumption was promoted without taking pause of the developing apparatus) while properly supplementing the toners. The image density of the obtained printed-out images was evaluated and its endurance was evaluated based on the following. Also, the 10,000th printed-out image was observed and evaluated for the image fogging based on the following. Further, simultaneously, the conditions of respective unis composing the image forming apparatus after the endurance test were observed to evaluate matching of the respective toners with the foregoing respective units. The above-described evaluation results were collectively shown in Table 20.

[Changes in Image Density During Endurance]

Printing out was carried out in a prescribed number of common paper sheets (75 g/m$^2$) for a copying machine and the image density was evaluated base on the degree of the image density retention of a printed-out image on completion of printing to that of a printed-out image at the initial time. The image density was evaluated by measuring the relative density of each printed-out image to the while area with an original image density of 0.00, using Macbeth Reflectometer (manufactured by Macbeth Co.)

AA: excellent (the image density on completion 1.40 or higher)
A: good (the image density on completion not lower than 1.35 and lower than 1.40)
B: fair (the image density on completion not lower than 1.00 and lower than 1.35)
C: poor (the image density on completion lower than 1.00)

[Image Fogging]

Printing out was carried out in a prescribed number of common paper sheets (75 g/m$^2$) and the image fogging was evaluated base on the entirely white image at the time of completion of printing. More particularly, the evaluation was carried out by the following manner. The worst value of the reflection density of the white areas after printing measured using a reflectometer (REFLECTOMETER ODEL TC-6DS, manufactured by TOKYO DENSHOKU CO., LTD.) was defined as Ds and the average value of the reflection density of the paper sheets before printing was defined as Dr and the value (Ds−Dr) was calculated as the fogging and evaluated based on the following.

AA: excellent (the fogging 0% or higher and less than 1.5%)
A: good (the fogging 1.5% or higher and less than 3.0%)
B: practically usable (the fogging 3.0% or higher and less than 5.0%)
C: impossible for use (the fogging 5.0% or higher)

[Evaluation of Matching with Image Forming Apparatus]

1. Matching with Developing Sleeve

On completion of the printing-out test, adhesion of the residual toner to the surface of the developing sleeve and the effect on the printed-out images were evaluated by eye observation.

AA: excellent (no occurrence)
A: good (scarce occurrence)
B: practically usable (adhesion observed but scarce effect on images)
C: impossible for use (much adhesion observed and image unevenness observed)

2. Matching with Photosensitive Drum

Scratches on the surface of the photosensitive drum and occurrence of the adhesion of the residual toner and the effect on the printed-out images were evaluated by eye observation.

AA: excellent (no occurrence)
A: good (few scratches observed but no effect on images)
B: practically usable (adhesion and scratches observed but scarce effect on images)
C: impossible for use (much adhesion observed and vertical stripe-like image defect observed)

3. Matching with Fixing Apparatus

The fixing film surface was observed and the surface property and the adhesion of the residual toner were comprehensively averaged to evaluate the durability.

(1) Surface Property

The occurrence of the scratches and cuts in the surface of the fixing film was observed with eye observation and evaluated on completion of the printing-out test.

AA: excellent (no occurrence)
A: good (scarce occurrence)
B: practically usable
C: impossible for use (2) Adhesion of Residual Toner The adhesion of the residual toner on the surface of the fixing film was observed with eye observation and evaluated on completion of the printing-out test.

AA: excellent (no occurrence)
A: good (scarce occurrence)
B: practically usable
C: impossible for use

TABLE 20

Result of Printed-Out Image Evaluation and Matching with Image Formation Apparatus

| | | Printed-out image evaluation | | | | | Matching with each apparatus | | Fixing apparatus | |
| | | Changes in image density during endurance | | | | Image fogging | Developing sleeve | Photosensitive drum | Toner | |
| Example | Toner | Initial | 1,000 copies | 10,000 copies | 30,000 copies | 10,000 copies | | | Surface property | adhesion |
|---|---|---|---|---|---|---|---|---|---|---|
| 57 | Blue 1 | AA | AA | AA | AA | AA | AA | AA | AA | AA |
| 58 | Yellow 1 | AA | AA | AA | AA | AA | AA | AA | AA | AA |
| 59 | Black 1 | AA | AA | AA | AA | AA | AA | AA | AA | AA |
| Comparative Example 13 | Blue 4 | B | C | C | C | C | C | C | C | C |

TABLE 20-continued

Result of Printed-Out Image Evaluation and Matching with Image Formation Apparatus

| | | Printed-out image evaluation | | | | Matching with each apparatus | | | |
| | | Changes in image density during endurance | | | Image fogging | Develop- | Photosen- | Fixing apparatus | Toner |
| Example | Toner | Initial | 1,000 copies | 10,000 copies | 30,000 copies | 10,000 copies | ing sleeve | sitive drum | Surface property | adhesion |
|---|---|---|---|---|---|---|---|---|---|---|
| 14 | Yellow 4 | B | C | C | C | C | C | C | C | C |
| 15 | Black 4 | A | B | C | C | C | C | C | C | C |

EXAMPLE 60

Printing-out was carried out in a continuous mode (that is, a mode in which toner consumption was promoted without taking pause of the developing apparatus) while properly supplementing the blue toner (1) of Example 21 in the same manner as Example 47 except that the toner reuse mechanism of the image forming apparatus in FIG. 3 was taken out and the printing-out speed was changed to be 16 sheets (A4 size)/min. The obtained printed-out image evaluation and matching with the image forming apparatus were carried out in the same items as those evaluated for Example 47 to Example 59 and the Comparative Example 13 and Comparative Example 15. As a result, excellent results were obtained in any item.

The present invention has been described in detail with respect to preferred embodiments, and it will now be that changed and modifications may be made without departing from the invention in its boarder aspects, and it is the invention, therefore, in the appended claims to cover all such changes and modifications as fall within the true spirit of the invention.

What is claimed is:

1. A polyhydroxyalkanoate comprising units having the following chemical formulas (1) and (2) and at least one selected from four units having the following chemical formulas (3), (4), (5) and (6), in a molecule;

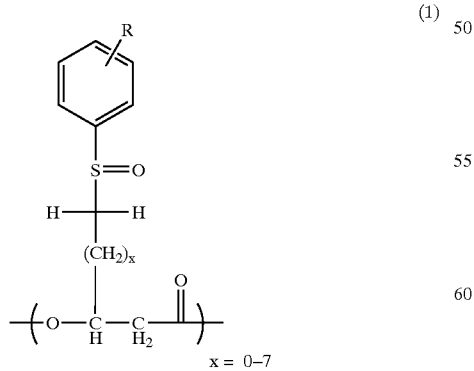

(1)

wherein R is a substituent optionally selected from H, a halogen atom, CN, $NO_2$, COOR', $SO_2R''$, $CH_3$, $C_2H_5$, $CH_3CH_2CH_2$, $(CH_3)_2CH$ and $(CH_3)_3C$ (R' is H, Na, K, $CH_3$ or $C_2H_5$; and R" is OH, ONa, OK, a halogen atom, $OCH_3$ or $OC_2H_5$); and x is at least one optional integer value within the range shown in the formula;

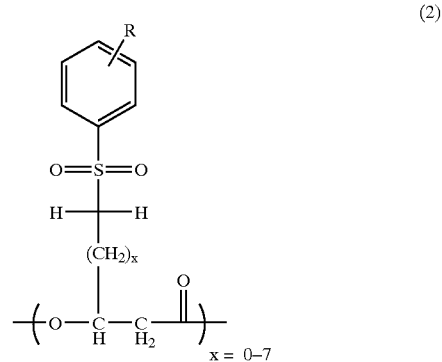

(2)

wherein R is a substituent optionally selected from H, a halogen atom, CN, $NO_2$, COOR', $SO_2R''$, $CH_3$, $C_2H_5$, $CH_3CH_2CH_2$, $(CH_3)_2CH$ and $(CH_3)_3C$ (R' is H, Na, K, $CH_3$ or $C_2H_5$; and R" is OH, ONa, OK, a halogen atom, $OCH_3$ or $OC_2H_5$); and x is at least one optional integer value within the range shown in the formula;

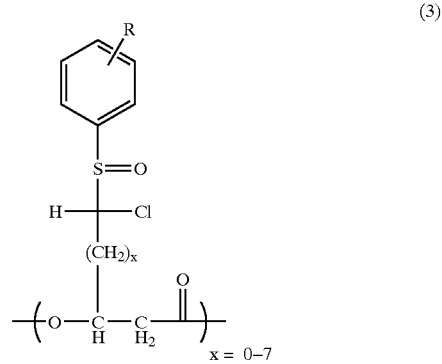

(3)

wherein R is a substituent optionally selected from H, a halogen atom, CN, $NO_2$, COOR', $SO_2R''$, $CH_3$, $C_2H_5$, $CH_3CH_2CH_2$, $(CH_3)_2CH$ and $(CH_3)_3C$ (R' is H, Na, K, $CH_3$ or $C_2H_5$; and R" is OH, ONa, OK, a halogen atom, $OCH_3$ or $OC_2H_5$); and x is at least one optional integer value within the range shown in the formula;

(4)

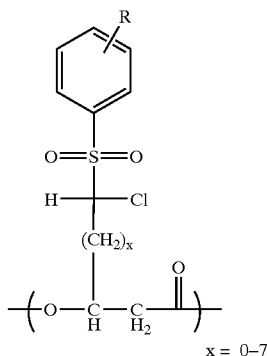

wherein R is a substituent optionally selected from H, a halogen atom, CN, $NO_2$, COOR', $SO_2R''$, $CH_3$, $C_2H_5$, $CH_3CH_2CH_2$, $(CH_3)_2CH$ and $(CH_3)_3C$ (R' is H, Na, K, $CH_3$ or $C_2H_5$; and R'' is OH, ONa, OK, a halogen atom, $OCH_3$ or $OC_2H_5$); and x is at least one optional integer value within the range shown in the formula;

(5)

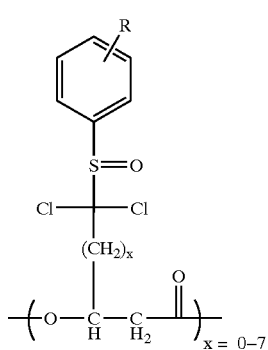

wherein R is a substituent optionally selected from H, a halogen atom, CN, $NO_2$, COOR', $SO_2R''$, $CH_3$, $C_2H_5$, $CH_3CH_2CH_2$, $(CH_3)_2CH$ and $(CH_3)_3C$ (R' is H, Na, K, $CH_3$ or $C_2H_5$; and R'' is OH, ONa, OK, a halogen atom, $OCH_3$ or $OC_2H_5$); and x is at least one optional integer value within the range shown in the formula;

(6)

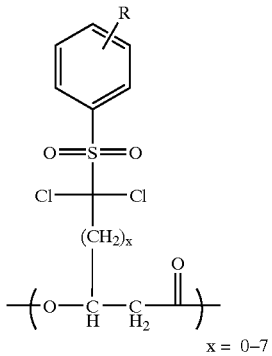

wherein R is a substituent optionally selected from H, a halogen atom, CN, $NO_2$, COOR', $SO_2R''$, $CH_3$, $C_2H_5$, $CH_3CH_2CH_2$, $(CH_3)_2CH$ and $(CH_3)_3C$ (R' is H, Na, K, $CH_3$ or $C_2H_5$; and R'' is OH, ONa, OK, a halogen atom, $OCH_3$ or $OC_2H_5$); and x is at least one optional integer value within the range shown in the formula.

2. The polyhydroxyalkanoate according to claim 1, wherein the polyhydroxyalkanoate further contains at least one of units having the following chemical formulas (7) and (8) besides the units having the chemical formulas (1), (2), (3), (4), (5) and (6);

(7)

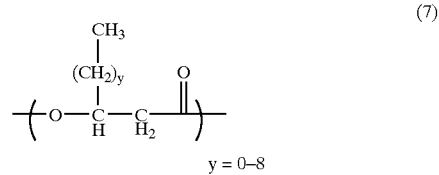

$y = 0-8$ (8)

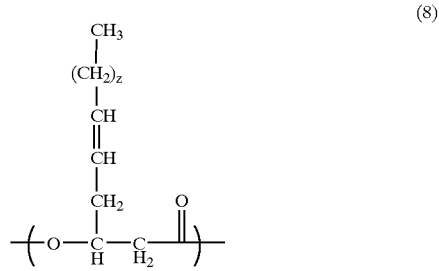

$z = 3, 5$ wherein y and z independently are at least one optional integer value within the range shown in the chemical formula, independently of the units having the chemical formulas (1), (2), (3), (4), (5) and (6).

3. The polyhydroxyalkanoate according to claim 1, wherein a number average molecular weight of the polyhydroxyalkanoate is in a range from 1,000 to 500,000.

4. A production method of polyhydroxyalkanoate according to claim 1, comprising:
a step 1 of culturing a microorganism in a culture medium containing at least one kind of compounds having the following chemical formula (27) and compounds having the following chemical formula (28):

(27)

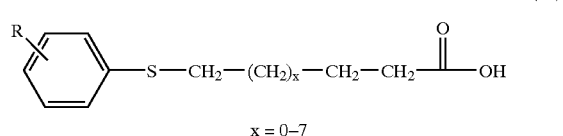

$x = 0-7$ wherein R is a substituent optionally selected from H, a halogen atom, CN, $NO_2$, COOR', $SO_2R''$, $CH_3$, $C_2H_5$, $CH_3CH_2CH_2$, $(CH_3)_2CH$ and $(CH_3)_3C$ (R' is H, Na, K, $CH_3$ or $C_2H_5$; and R'' is OH, ONa, OK, a halogen atom, $OCH_3$, or $OC_2H_5$); and x is at least one optional integer value within the range shown in the formula; and (28)

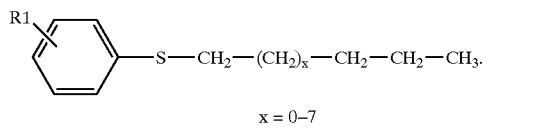

$x = 0-7$ wherein R1 denotes a substituent on an aromatic ring and is optionally selected from H, a halogen atom, CN, $NO_2$, $CH_3$, $C_2H_5$, $CH_3CH_2CH_2$, $(CH_3)_2CH$ and $(CH_3)_3C$; and x is at least one optional integer value within the range shown in the formula; and a step 2 of treating the polyhydroxyalkanoate produced by the cultured microorganism with sodium hypochlorite.

5. The production method according to claim 4, wherein a step of separating the polyhydroxyalkanoate from a cell of the cultured microorganism is provided between the step 1 and the step 2.

6. The production method according to claim 5, wherein the step of separating the polyhydroxyalkanoate from the cultured microorganism cell comprises a step of extracting the polyhydroxyalkanoate from the microorganism cell with a solvent capable of making the polyhydroxyalkanoate soluble.

7. The production method according to claim 4, wherein the culture medium employed in the step 1 contains polypeptone.

8. The production method according to claim 4, wherein the culture medium employed in the step 1 contains yeast extract.

9. The production method according to claim 4, wherein the culture medium employed in the step 1 contains saccharide.

10. The production method according to claim 9, wherein the saccharide contained in the culture medium is one or more compounds selected from glyceraldehyde, erythrose, arabinose, xylose, glucose, galactose, mannose, fructose, glycerol, erythritol, xylitol, gluconic acid, glucuronic acid, galacturonic acid, maltose, sucrose, and lactose.

11. The production method according to claim 4, wherein the culture medium employed in the step 1 contains an organic acid or its salt.

12. The production method according to claim 11, wherein the organic acid or its salt contained in the culture medium is one or more compounds selected from pyruvic acid, malic acid, lactic acid, citric acid, succinic acid and their salts.

13. The production method according to claim 4, wherein the culture medium employed in the step 1 contains amino acid or its salt.

14. The production method according to claim 13, wherein the amino acid or its salt contained in the culture medium are one or more compounds selected from glutamic acid, aspartic acid and their salts.

15. The production method according to claim 4, wherein the culture medium employed in the step 1 contains a straight chain alkanoic acid of 4 to 12 carbons or its salt.

16. The production method according to claim 4, further comprising a step of culturing the microorganism in a culture medium containing dicyclopropylketone in the step 1.

17. The production method according to claim 4, wherein the microorganism is a microorganism having alkanemonooxygenase.

18. The production method according to claim 4, wherein the microorganism culture in the step 1 comprises:

a step 1-1 of culturing the microorganism in a culture medium containing polypeptone and at least one kind of compounds having the following chemical formula (27), and then, a step 1-2 of culturing the microorganism cultured in the step 1-1, in a culture medium containing an organic acid or its salt, and at least one kind of compounds having the chemical formula (27):

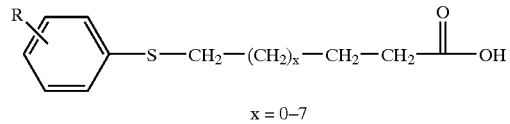

wherein R is a substituent optionally selected from H, a halogen atom, CN, $NO_2$, COOR', $SO_2R''$, $CH_3$, $C_2H_5$, $CH_3CH_2CH_2$, $(CH_3)_2CH$ and $(CH_3)_3C$ (R' is H, Na, K, $CH_3$ or $C_2H_5$; and R" is OH, ONa, OK, a halogen atom, $OCH_3$ or $OC_2H_5$); and x is at least one optional integer value within the range shown in the formula.

19. The production method according to claim 4, wherein the microorganism culture in the step 1 comprises:

a step 1-3 of culturing the microorganism in a culture medium containing saccharide and at least one kind of compounds having the following chemical formula (27), and then, a step 1-4 of culturing the microorganism cultured in the step 1-3, in a culture medium containing saccharide and at least one kind of compounds having the chemical formula (27):

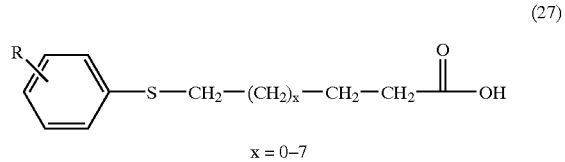

wherein R is a substituent optionally selected from H, a halogen atom, CN, $NO_2$, COOR', $SO_2R''$, $CH_3$, $C_2H_5$, $CH_3CH_2CH_2$, $(CH_3)_2CH$ and $(CH_3)_3C$ (R' is H, Na, K, $CH_3$ or $C_2H_5$; and R" is OH, ONa, OK, a halogen atom, $OCH_3$ or $OC_2H_5$); and x is at least one optional integer value within the range shown in the formula.

20. The production method according to claim 4, wherein the microorganism belongs to *Pseudomonas* species.

21. The production method according to claim 20, wherein the microorganism is one or more strains selected from *Pseudomonas cichorii* YN2 strain (FERM BP-7375), *Pseudomonas cichorii* H45 strain (FERM BP-7374), and *Pseudomonas jessenii* P161 strain (FERM BP-7376).

22. In a charge control agent composition for controlling an electrostatic charging state of a powder particle, the improvement which comprises as a charge control agent, a polyhydroxyalkanoate including units having the following chemical formulas (1) and (2) and at least one selected from four types of units having the following chemical formulas (3), (4), (5) and (6):

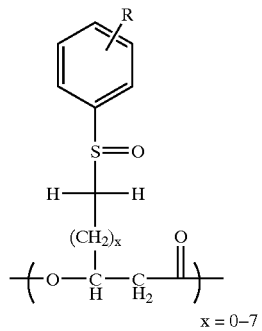

(1)

x = 0–7 wherein R is a substituent optionally selected from H, a halogen atom, CN, $NO_2$, COOR', $SO_2R''$, $CH_3$, $C_2H_5$, $CH_3CH_2CH_2$, $(CH_3)_2CH$ and $(CH_3)_3C$ (R' is H, Na, K, $CH_3$ or $C_2H_5$; and R'' is OH, ONa, OK, a halogen atom, $OCH_3$ or $OC_2H_5$); and x is at least one optional integer value within the range shown in the formula;

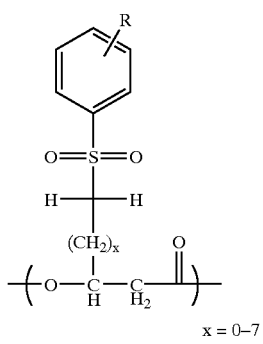

(2)

x = 0–7 wherein R is a substituent optionally selected from H, a halogen atom, CN, $NO_2$, COOR', $SO_2R''$, $CH_3$, $C_2H_5$, $CH_3CH_2CH_2$, $(CH_3)_2CH$ and $(CH_3)_3C$ (R' is H, Na, K, $CH_3$ or $C_2H_5$; and R'' is OH, ONa, OK, a halogen atom, $OCH_3$ or $OC_2H_5$); and x is at least one optional integer value within the range shown in the formula;

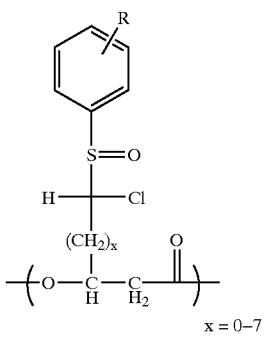

(3)

x = 0–7 wherein R is a substituent optionally selected from H, a halogen atom, CN, $NO_2$, COOR', $SO_2R''$, $CH_3$, $C_2H_5$, $CH_3CH_2CH_2$, $(CH_3)_2CH$ and $(CH_3)_3C$ (R' is H, Na, K, $CH_3$ or $C_2H_5$; and R'' is OH, ONa, OK, a halogen atom, $OCH_3$ or $OC_2H_5$); and x is at least one optional integer value within the range shown in the formula;

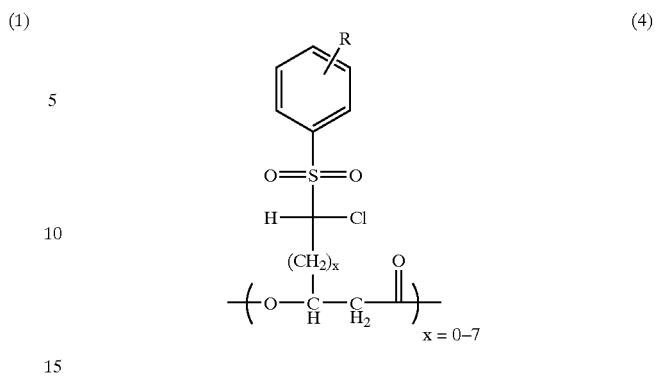

(4)

x = 0–7 wherein R is a substituent optionally selected from H, a halogen atom, CN, $NO_2$, COOR', $SO_2R''$, $CH_3$, $C_2H_5$, $CH_3CH_2CH_2$, $(CH_3)_2CH$ and $(CH_3)_3C$ (R' is H, Na, K, $CH_3$ or $C_2H_5$; and R'' is OH, ONa, OK, a halogen atom, $OCH_3$ or $OC_2H_5$); and x is at least one optional integer value within the range shown in the formula;

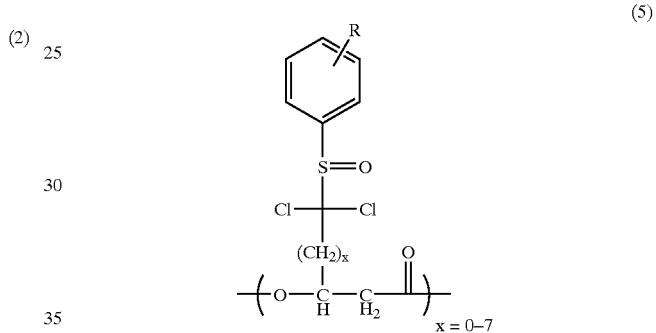

(5)

x = 0–7 wherein R is a substituent optionally selected from H, a halogen atom, CN, $NO_2$, COOR', $SO_2R''$, $CH_3$, $C_2H_5$, $CH_3CH_2CH_2$, $(CH_3)_2CH$ and $(CH_3)_3C$ (R' is H, Na, K, $CH_3$ or $C_2H_5$; and R'' is OH, ONa, OK, a halogen atom, $OCH_3$ or $OC_2H_5$); and x is at least one optional integer value within the range shown in the formula; and

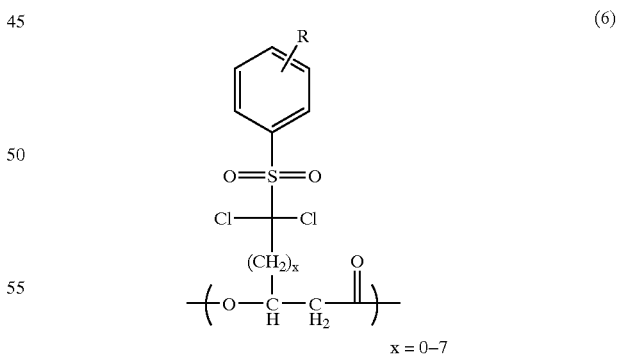

(6)

x = 0–7 wherein R is a substituent optionally selected from H, a halogen atom, CN, $NO_2$, COOR', $SO_2R''$, $CH_3$, $C_2H_5$, $CH_3CH_2CH_2$, $(CH_3)_2CH$ and $(CH_3)_3C$ (R' is H, Na, K, $CH_3$ or $C_2H_5$; and R'' is OH, ONa, OK, a halogen atom, $OCH_3$ or $OC_2H_5$); and x is at least one optional integer value within the range shown in the formula.

23. The charge control agent composition according to claim 22, further comprising at least one of units having the following chemical formulas (7) and (8) besides the units having the chemical formulas (1), (2), (3), (4), (5) and (6);

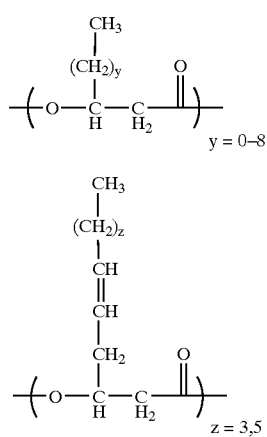

wherein y and z independently are at least one optional integer value within the range shown in the general formula, independently of the units having the chemical formulas (1), (2), (3), (4), (5) and (6).

24. The charge control agent composition according to claim 22, wherein the powder particle is an electrostatic latent image developing toner.

25. The charge control agent composition according to claim 22, wherein the polyhydroxyalkanoate has a number average molecular weight in a range from 1,000 to 500,000.

26. In a toner binder composition, including a binder and a charge control agent, for use in an electrostatic latent image developing toner, the improvement which comprises the charge control agent according to claim 22.

27. An electrostatic latent image developing toner containing at least binder resin, a coloring agent, and the charge control agent according to claim 22.

28. An image forming method comprising a step of charging an electrostatic latent image carrier by applying voltage to a charging member from the outside, a step of forming an electrostatic latent image on the charged electrostatic latent image carrier, a development step of developing the electrostatic latent image by an electrostatic latent image developing toner to form a toner image on the electrostatic latent image carrier, a transfer step of transferring the toner image on the electrostatic latent image carrier to a recording material, and a fixation step of fixing the toner image on the recording material by heating, wherein the electrostatic latent image developing toner containing at least a binder resin, a coloring agent and the controlling agent according to claim 22 is used.

29. The image forming method according to claim 28, wherein the method comprises a step of charging an electrostatic latent image carrier by applying voltage to a charging member from the outside, a step of forming an electrostatic latent image on the charged electrostatic latent image carrier, a development step of developing the electrostatic latent image by an electrostatic latent image developing toner to form a toner image on the electrostatic latent image carrier, a first transfer step of transferring the toner image on the electrostatic latent image carrier to an intermediate transfer member, a second transfer step of transferring the toner image on the intermediate transfer member to a recording material, and a fixation step of fixing the toner image on the recording material by heating, wherein the electrostatic latent image developing toner containing at least a binder resin, a coloring agent and the controlling agent according to claim 22 is used.

30. An image forming apparatus for forming an image on a recording material by using the electrostatic latent image developing toner according to claim 27.

31. The image forming apparatus according to claim 30, comprising: means for charging an electrostatic latent image carrier by applying voltage to a charging member from the outside, means for forming an electrostatic latent image on the charged electrostatic latent image carrier, development means for developing the electrostatic latent image by the electrostatic latent image developing toner to form a toner image on the electrostatic latent image carrier, transfer means for transferring the toner image on the electrostatic latent image carrier to a recording material, and fixation means for fixing the toner image on the recording material by heating, wherein the electrostatic latent image developing toner according to claim 27 is used.

32. An image forming apparatus according to claim 31, comprising: means for charging an electrostatic latent image carrier by applying voltage to a charging member from the outside, means for forming an electrostatic latent image on the charged electrostatic latent image carrier, development means for developing the electrostatic latent image by the electrostatic latent image developing toner to form a toner image on the electrostatic latent image carrier, first transfer means of transferring the toner image on the electrostatic latent image carrier to an intermediate transfer member, second transfer means of transferring the toner image on the intermediate transfer member to a recording material, and fixation means of fixing the toner image on the recording material by heating, wherein the electrostatic latent image developing toner according to claim 22 is used.

* * * * *

UNITED STATES PATENT AND TRADEMARK OFFICE
CERTIFICATE OF CORRECTION

PATENT NO.     : 6,908,720 B2
DATED          : June 21, 2005
INVENTOR(S)    : Takashi Kenmoku et al.

It is certified that error appears in the above-identified patent and that said Letters Patent is hereby corrected as shown below:

Title page,
Item [56], References Cited, FOREIGN PATENT DOCUMENTS, insert:
-- EP    1 245 682    2/2002 --.
OTHER PUBLICATIONS, insert:
-- Steinbüchel, et al., "Diversity of bacterial polyhydroxyalkanoic acids", FEMS Microbiology Ltrs., vol. 128, pp. 219-228 (1995). --.

Column 1,
Line 44, "many" should read -- of many --.

Column 2,
Line 47, "11-pheoxyundecanoic" should read -- 11-phenoxyundecanoic --.

Column 4,
Line 66, "polyhyroxybutyric" should read -- polyhydroxybutyric --.

Column 12,
Line 64, "contains" should read -- contain --.

Column 13,
Line 51, Formula (28), the portion of the formula reading "R" should read -- R1 --.

Column 14,
Line 50, "provide" should read -- be provided --.

Column 18,
Line 66, "forming" should read -- of forming --.

Column 19,
Line 7, "that" should be deleted; and
Line 11, "provide" should read -- provides --.

Column 20,
Line 61, "details." should read -- detail. --.

Column 21,
Line 20, "details" should read -- detail --; and
Line 26, "details." should read -- detail. --.

UNITED STATES PATENT AND TRADEMARK OFFICE
CERTIFICATE OF CORRECTION

PATENT NO. : 6,908,720 B2
DATED : June 21, 2005
INVENTOR(S) : Takashi Kenmoku et al.

It is certified that error appears in the above-identified patent and that said Letters Patent is hereby corrected as shown below:

Column 26,
Line 30, "*Psudomonas*" should read -- *Pseudomonas* --;
Line 31, "*Psudomonas cichorii*" should read -- *Pseudomonas cichorii* --;
Line 52, "may be" should read -- for --;
Line 53, "an use" should read -- to use an --; and
Line 59, "based" should read -- based on --.

Column 27,
Line 4, "owing to" should read -- because --;
Line 21, "not be" should read -- not to be --;
Line 29, "induce" should read -- induces --; and
Line 59, "is a the" should read -- is at the --.

Column 28,
Line 2, "add" should read -- added --.

Column 33,
Line 42, "formulas and" should read -- and --; and "kind" should read -- kinds of --.

Column 35,
Line 20, "$SO_2R$"" should read -- $SO_2R$", --.

Column 36,
Line 61, "comprises" should read -- comprise --.

Column 38,
Line 20, "preferably" should read -- preferable --.

Column 39,
Line 47, "order" should read -- order to --.

Column 40,
Line 10, "tone binder" should read -- toner binder --.

Column 42,
Line 57, "Watching" should read -- Watchung --.

Column 43,
Line 33, "may widely" should read -- may be widely --; and
Line 41, "In the" should read -- The --.

UNITED STATES PATENT AND TRADEMARK OFFICE
CERTIFICATE OF CORRECTION

PATENT NO. : 6,908,720 B2
DATED : June 21, 2005
INVENTOR(S) : Takashi Kenmoku et al.

It is certified that error appears in the above-identified patent and that said Letters Patent is hereby corrected as shown below:

Column 44,
Line 15, "material" should read -- materials --.

Column 45,
Line 12, "treatment agent" should read -- treatment agents --.

Column 68,
Lines 2, 3, 65 and 66, "humidify" should read -- humidity --; and
Line 43, "10" should be deleted.

Column 70,
Lines 34 and 35, "humidify" should read -- humidity --.

Column 72,
Lines 43 and 44, "humidify" should read -- humidity --.

Column 74,
Lines 30 and 31, "humidify" should read -- humidity --.

Column 76,
Lines 17 and 18, "humidify" should read -- humidity --.

Column 78,
Lines 7 and 8, "humidify" should read -- humidity --;
Line 24, "base" should read -- based --;
Line 28, "while" should read -- white --; and
Line 41, "base" should read -- based --.

Column 79,
Line 14, "surface" should read -- surface of the --.

Column 81,
Line 8, "unis" should read -- units --;
Lines 16 and 33, "base" should read -- based --; and
Line 20, "while" should read -- white --.

Column 83,
Line 37, "changed" should read -- changes --; and
Line 39, "invention," should read -- intention, --.

UNITED STATES PATENT AND TRADEMARK OFFICE
CERTIFICATE OF CORRECTION

PATENT NO.    : 6,908,720 B2
DATED         : June 21, 2005
INVENTOR(S)   : Takashi Kenmoku et al.

It is certified that error appears in the above-identified patent and that said Letters Patent is hereby corrected as shown below:

<u>Column 92,</u>
Line 48, "claim 22" should read -- claim 27 --.

Signed and Sealed this

Twenty-eighth Day of March, 2006

JON W. DUDAS
*Director of the United States Patent and Trademark Office*